US011174315B2

(12) United States Patent
Vasselli et al.

(10) Patent No.: US 11,174,315 B2
(45) Date of Patent: Nov. 16, 2021

(54) COMBINATION THERAPY FOR THE TREATMENT OF CANCER

(71) Applicant: MacroGenics, Inc., Rockville, MD (US)

(72) Inventors: James Vasselli, Rockville, MD (US); Jon Marc Wigginton, Rockville, MD (US); Ezio Bonvini, Potomac, MD (US); Scott Koenig, Rockville, MD (US)

(73) Assignee: MacroGenics, Inc., Rockville, MD (US)

( * ) Notice: Subject to any disclaimer, the term of this patent is extended or adjusted under 35 U.S.C. 154(b) by 453 days.

(21) Appl. No.: 15/765,697

(22) PCT Filed: Oct. 6, 2016

(86) PCT No.: PCT/US2016/055750
§ 371 (c)(1),
(2) Date: Apr. 3, 2018

(87) PCT Pub. No.: WO2017/062619
PCT Pub. Date: Apr. 13, 2017

(65) Prior Publication Data

US 2019/0389952 A1 Dec. 26, 2019

Related U.S. Application Data

(60) Provisional application No. 62/239,020, filed on Oct. 8, 2015.

(51) Int. Cl.

| | |
|---|---|
| ***C07K 16/28*** | (2006.01) |
| ***A61P 35/00*** | (2006.01) |
| ***A61K 45/06*** | (2006.01) |
| *A61K 39/00* | (2006.01) |

(52) U.S. Cl.
CPC .......... *C07K 16/2827* (2013.01); *A61K 45/06* (2013.01); *A61P 35/00* (2018.01); *C07K 16/2818* (2013.01); *A61K 2039/507* (2013.01); *A61K 2039/545* (2013.01); *C07K 2317/24* (2013.01); *C07K 2317/524* (2013.01); *C07K 2317/526* (2013.01); *C07K 2317/565* (2013.01); *C07K 2317/72* (2013.01); *C07K 2317/732* (2013.01)

(58) Field of Classification Search
None
See application file for complete search history.

(56) References Cited

U.S. PATENT DOCUMENTS

| | | | |
|---|---|---|---|
| 3,842,067 | A | 10/1974 | Sarantakis |
| 3,862,925 | A | 1/1975 | Sarantakis et al. |
| 3,972,859 | A | 8/1976 | Souter |
| 4,105,603 | A | 8/1978 | Vale, Jr. et al. |
| 4,816,567 | A | 3/1989 | Cabilly et al. |
| 4,880,078 | A | 11/1989 | Inoue et al. |
| 5,290,540 | A | 3/1994 | Prince et al. |
| 5,565,332 | A | 10/1996 | Hoogenboom et al. |
| 5,580,717 | A | 12/1996 | Dower et al. |
| 5,733,743 | A | 3/1998 | Johnson et al. |
| 5,807,715 | A | 9/1998 | Morrison et al. |
| 5,855,913 | A | 1/1999 | Hanes et al. |
| 5,866,692 | A | 2/1999 | Shitara et al. |
| 5,874,064 | A | 2/1999 | Edwards et al. |
| 5,934,272 | A | 8/1999 | Lloyd et al. |
| 5,952,136 | A | 9/1999 | Daems et al. |
| 5,985,309 | A | 11/1999 | Edwards et al. |
| 5,985,320 | A | 11/1999 | Edwards et al. |
| 5,997,867 | A | 12/1999 | Waldmann et al. |
| 6,019,968 | A | 2/2000 | Platz et al. |
| 6,054,297 | A | 4/2000 | Carter et al. |
| 6,171,586 | B1 | 1/2001 | Lam et al. |
| 6,180,377 | B1 | 1/2001 | Morgan et al. |
| 6,265,150 | B1 | 7/2001 | Terstappen et al. |
| 6,331,415 | B1 | 12/2001 | Cabilly et al. |
| 6,551,592 | B2 | 4/2003 | Lindhofer et al. |
| 6,803,192 | B1 | 10/2004 | Chen |

(Continued)

FOREIGN PATENT DOCUMENTS

| | | |
|---|---|---|
| CA | 2611861 | 12/2006 |
| CA | 2840482 | 1/2013 |

(Continued)

OTHER PUBLICATIONS

Tame (J. Comput. Aided Mol. Des. Mar. 1999; 13 (2): 99-108).*

(Continued)

*Primary Examiner* — Brad Duffy

(74) *Attorney, Agent, or Firm* — William C. Schrot; Jeffrey I. Auerbach; AuerbachSchrot LLC

(57) ABSTRACT

The present invention is directed to a combination therapy involving the administration of a first molecule that specifically binds to human B7-H3 and a second molecule that specifically binds to human PD-1 to a subject for the treatment of cancer and/or inflammation. The invention also concerns pharmaceutical compositions that comprise a first molecule that specifically binds to human B7-H3 and a second molecule that specifically binds to human PD-1 that are capable of mediating, and more preferably enhancing, the activation of the immune system against cancer cells that are associated with any of a variety of human cancers. The invention also relates to the use of such pharmaceutical compositions to treat cancer and other diseases in recipient subjects.

39 Claims, No Drawings

Specification includes a Sequence Listing.

(56) References Cited

U.S. PATENT DOCUMENTS

| | | | |
|---|---|---|---|
| 6,808,710 | B1 | 10/2004 | Wood et al. |
| 6,891,030 | B2 | 5/2005 | Chen |
| 6,994,853 | B1 | 2/2006 | Lindhofer et al. |
| 7,083,784 | B2 | 8/2006 | Dall'Acqua et al. |
| 7,101,550 | B2 | 9/2006 | Wood et al. |
| 7,217,797 | B2 | 5/2007 | Hinton et al. |
| 7,279,567 | B2 | 10/2007 | Mikesell et al. |
| 7,358,354 | B2 | 4/2008 | Mikesell et al. |
| 7,368,554 | B2 | 5/2008 | Mikesell et al. |
| 7,488,802 | B2 | 2/2009 | Collins et al. |
| 7,521,051 | B2 | 4/2009 | Collins et al. |
| 7,527,969 | B2 | 5/2009 | Mather et al. |
| 7,563,869 | B2 | 7/2009 | Honjo et al. |
| 7,595,048 | B2 | 9/2009 | Honjo et al. |
| 7,635,757 | B2 | 12/2009 | Freeman et al. |
| 7,638,492 | B2 | 12/2009 | Wood et al. |
| 7,666,424 | B2 | 2/2010 | Cheung et al. |
| 7,695,936 | B2 | 4/2010 | Carter et al. |
| 7,718,774 | B2 | 5/2010 | Mather et al. |
| 7,722,868 | B2 | 5/2010 | Freeman et al. |
| 7,732,131 | B2 | 6/2010 | Moretta et al. |
| 7,737,258 | B2 | 6/2010 | Cheung |
| 7,740,845 | B2 | 6/2010 | Cheung |
| 7,794,710 | B2 | 9/2010 | Chen et al. |
| 7,847,081 | B2 | 12/2010 | Chen |
| 7,943,743 | B2 | 5/2011 | Korman et al. |
| 8,008,449 | B2 | 8/2011 | Korman et al. |
| 8,088,376 | B2 | 1/2012 | Chamberlain et al. |
| 8,088,905 | B2 | 1/2012 | Collins et al. |
| 8,129,347 | B2 | 3/2012 | Chen |
| 8,148,154 | B2 | 4/2012 | Cheung et al. |
| 8,216,570 | B2 | 7/2012 | Mather et al. |
| 8,277,806 | B2 | 10/2012 | Lindhofer |
| 8,354,509 | B2 | 1/2013 | Carven et al. |
| 8,414,892 | B2 | 4/2013 | Cheung |
| 8,501,471 | B2 | 8/2013 | Cheung |
| 8,552,154 | B2 | 10/2013 | Freeman et al. |
| 8,609,089 | B2 | 12/2013 | Langermann et al. |
| 8,709,416 | B2 | 4/2014 | Langermann et al. |
| 8,779,098 | B2 | 7/2014 | Mather et al. |
| 8,779,105 | B2 | 7/2014 | Korman et al. |
| 8,802,091 | B2 | 8/2014 | Johnson et al. |
| 8,900,587 | B2 | 12/2014 | Carven et al. |
| 9,062,110 | B2 | 6/2015 | Cheung |
| 9,062,112 | B2 | 6/2015 | Chen |
| 9,084,776 | B2 | 7/2015 | Korman et al. |
| 9,205,148 | B2 | 12/2015 | Langermann et al. |
| 9,371,395 | B2 | 6/2016 | Takahashi et al. |
| 2002/0147311 | A1 | 10/2002 | Gilles et al. |
| 2002/0168762 | A1 | 11/2002 | Chen |
| 2003/0103963 | A1 | 6/2003 | Cheung |
| 2004/0241745 | A1 | 12/2004 | Honjo et al. |
| 2005/0059051 | A1 | 3/2005 | Chen |
| 2005/0202536 | A1 | 9/2005 | Chen |
| 2007/0148164 | A1 | 6/2007 | Farrington et al. |
| 2007/0166281 | A1 | 7/2007 | Kosak |
| 2007/0196363 | A1 | 8/2007 | Arathoon et al. |
| 2007/0202100 | A1 | 8/2007 | Wood et al. |
| 2008/0057054 | A1 | 3/2008 | Annaert et al. |
| 2008/0081346 | A1 | 4/2008 | Moretta et al. |
| 2008/0116219 | A1 | 5/2008 | Lawrence |
| 2008/0311117 | A1 | 12/2008 | Collins et al. |
| 2009/0018315 | A1 | 1/2009 | Chen |
| 2009/0022747 | A1 | 1/2009 | Chen |
| 2009/0055944 | A1 | 2/2009 | Korman et al. |
| 2009/0087416 | A1 | 4/2009 | Chen |
| 2009/0110667 | A1 | 4/2009 | Mozaffarian et al. |
| 2009/0217401 | A1 | 8/2009 | Korman et al. |
| 2009/0274666 | A1 | 11/2009 | Chen |
| 2009/0313687 | A1 | 12/2009 | Popp et al. |
| 2010/0028330 | A1 | 2/2010 | Collins et al. |
| 2010/0040614 | A1 | 2/2010 | Ahmed et al. |
| 2010/0143245 | A1 | 6/2010 | Cheung |
| 2010/0291112 | A1 | 11/2010 | Kellner et al. |
| 2012/0114648 | A1 | 5/2012 | Langermann et al. |
| 2012/0114649 | A1 | 5/2012 | Langermann et al. |
| 2012/0294796 | A1 | 11/2012 | Johnson et al. |
| 2013/0017199 | A1 | 1/2013 | Langermann |
| 2013/0078234 | A1 | 3/2013 | Takahashi et al. |
| 2013/0230514 | A1 | 9/2013 | Langermann et al. |
| 2014/0044738 | A1 | 2/2014 | Langermann et al. |
| 2014/0179664 | A1 | 6/2014 | Freeman et al. |
| 2014/0341902 | A1 | 11/2014 | Maecker et al. |
| 2014/0356363 | A1 | 12/2014 | Zhou et al. |
| 2015/0190506 | A1* | 7/2015 | Cheung .............. C07K 16/2878 424/134.1 |
| 2015/0203579 | A1 | 7/2015 | Papadopoulos et al. |
| 2018/0298100 | A1* | 10/2018 | Wigginton ............. C07K 16/32 |

FOREIGN PATENT DOCUMENTS

| | | |
|---|---|---|
| EP | 0519596 | 12/1992 |
| EP | 1292619 | 3/2003 |
| WO | WO 1991/003493 | 3/1991 |
| WO | WO 1992/019244 | 11/1992 |
| WO | WO 1992/022583 | 12/1992 |
| WO | WO 1997/032572 | 9/1997 |
| WO | WO 1997/044013 | 11/1997 |
| WO | WO 1998/002463 | 1/1998 |
| WO | WO 1998/003670 | 1/1998 |
| WO | WO 1998/006749 | 2/1998 |
| WO | WO 1998/023289 | 6/1998 |
| WO | WO 1998/031346 | 7/1998 |
| WO | WO 1998/050431 | 11/1998 |
| WO | WO 1999/042597 | 8/1999 |
| WO | WO 1999/066903 | 12/1999 |
| WO | WO 2000/018806 | 6/2000 |
| WO | WO 2001/014557 | 3/2001 |
| WO | WO 2001/039722 | 6/2001 |
| WO | WO 2001/094413 | 12/2001 |
| WO | WO 2002/010187 | 2/2002 |
| WO | WO 2002/020039 | 3/2002 |
| WO | WO 2002/032375 | 4/2002 |
| WO | WO 2002/086083 | 10/2002 |
| WO | WO 2003/099196 | 12/2003 |
| WO | WO 2004/0013 81 | 12/2003 |
| WO | WO 2004/004771 | 1/2004 |
| WO | WO 2004/056875 | 7/2004 |
| WO | WO 2004/063351 | 7/2004 |
| WO | WO 2004/072286 | 8/2004 |
| WO | WO 2004/093894 | 11/2004 |
| WO | WO 2005/070966 | 8/2005 |
| WO | WO 2006/016276 | 2/2006 |
| WO | WO 2006/072152 | 7/2006 |
| WO | WO 2006/088494 | 8/2006 |
| WO | WO 2006/107617 | 10/2006 |
| WO | WO 2006/107786 | 10/2006 |
| WO | WO 2006/113665 | 10/2006 |
| WO | WO 2006/121168 | 11/2006 |
| WO | WO 2007/005874 | 1/2007 |
| WO | WO 2007/021841 | 2/2007 |
| WO | WO 2007/024249 | 3/2007 |
| WO | WO 2007/046893 | 4/2007 |
| WO | WO 2007/075270 | 7/2007 |
| WO | WO 2007/106707 | 9/2007 |
| WO | WO 2007/110205 | 10/2007 |
| WO | WO 2007/146968 | 12/2007 |
| WO | WO 2008/003103 | 1/2008 |
| WO | WO 2008/003116 | 1/2008 |
| WO | WO 2008/027236 | 3/2008 |
| WO | WO 2008/066691 | 6/2008 |
| WO | WO 2008/083174 | 7/2008 |
| WO | WO 2008/116219 | 9/2008 |
| WO | WO 2008/140603 | 11/2008 |
| WO | WO 2008/145142 | 12/2008 |
| WO | WO 2008/156712 | 12/2008 |
| WO | WO 2009/014708 | 1/2009 |
| WO | WO 2009/018386 | 2/2009 |
| WO | WO 2009/058492 | 5/2009 |
| WO | WO 2009/073533 | 6/2009 |
| WO | WO 2009/132876 | 11/2009 |
| WO | WO 2010/028795 | 3/2010 |
| WO | WO 2010/028796 | 3/2010 |
| WO | WO 2010/028797 | 3/2010 |

(56) References Cited

FOREIGN PATENT DOCUMENTS

| | | |
|---|---|---|
| WO | WO 2010/033279 | 3/2010 |
| WO | WO 2010/036959 | 4/2010 |
| WO | WO 2010/108127 | 9/2010 |
| WO | WO 2010/136172 | 12/2010 |
| WO | WO 2011/086091 | 7/2011 |
| WO | WO 2011/109400 | 9/2011 |
| WO | WO 2011/133886 | 10/2011 |
| WO | WO 2011/143545 | 11/2011 |
| WO | WO 2012/009544 | 1/2012 |
| WO | WO 2012/058768 | 5/2012 |
| WO | WO 2012/135408 | 10/2012 |
| WO | WO 2012/145493 | 10/2012 |
| WO | WO 2012/145549 | 10/2012 |
| WO | WO 2012/147713 | 11/2012 |
| WO | WO 2012/156430 | 11/2012 |
| WO | WO 2012/162583 | 11/2012 |
| WO | WO 2013/003652 | 1/2013 |
| WO | WO 2013/006544 | 1/2013 |
| WO | WO 2013/006867 | 1/2013 |
| WO | WO 2013/014668 | 1/2013 |
| WO | WO 2013/070565 | 5/2013 |
| WO | WO 2013/119903 | 8/2013 |
| WO | WO 2013/163427 | 10/2013 |
| WO | WO 2013/174873 | 11/2013 |
| WO | WO 2014/022540 | 2/2014 |
| WO | WO 2014/179664 | 11/2014 |
| WO | WO 2014/194302 | 12/2014 |
| WO | WO 2015/069770 | 5/2015 |
| WO | WO 2015/095404 | 6/2015 |
| WO | WO 2015/112800 | 7/2015 |

OTHER PUBLICATIONS

Dixon (Proteins. 1997; Suppl 1: 198-204).*
Lensink et al. (Proteins. 2007; 69: 704-718).*
Lloyd et al (Protein Engineering, Design & Selection, 22:159-168, 2009).*
Edwards et al (J Mol Biol, 14;334(1):103-118, 2003).*
Momtaz et al (PPM, 7:357-365, 2014).*
Stagg et al (PNAS, 108(17):7142-7147, 2011).*
Barach, YS., et al., (2011) "*T cell Coinhibition in Prostate Cancer: New Immune Evasion Pathways and Emerging Therapeutics*", Trends Mol. Med. Jan: 17(1): 47-55 (Author Manuscript).
Homet Moreno, B., et al., (2015) *Anti-PD-1 Therapy in Melanoma*, Semin. Oncol. Jun: 42(3): 466-473.
Mueller, M.T., et al. (2009) "*Combined Targeted Treatment to Eliminate Tumorigenic Cancer Stem Cells in Human Pancreatic Cancer*", Gastroenterology Sep: 137(3):1102-1113.
Agata, T. et al. (1996) "*Expression of the PD-1 Antigen on The Surface of Stimulated Mouse T and B Lymphocytes*," Int. Immunol. 8(5):765-772.
Atwell et al. (1997) "*Stable Heterodimers from Remodeling the Domain Interface of A Homodimer Using A Phage Display Library*," J. Mol. Biol. 270: 26-35.
Baughman, J. et al. (2015) "*A Phase I, Open-Label, Dose Escalation Study OfMGA271 in Combination With Pembrolizumab in Patients With B7-H3-Expressing Melanoma, Squamous Cell Cancer of the Head and Neck, or Squamous Cell Non-Small Cell Lung Cancer*." 30th Annual Meeting and Associated Programs of the Society for Immunotherapy of Cancer (SITC 2015) 3(2):1-2.
Berger, R. et al. (2008) "*Phase I Safety and Pharmacokinetic Study of CT-011, A Humanized Antibody Interacting With PD-1, in Patients with Advanced Hematologic Malignancies*," Clin. Cancer Res. 14(10):3044-3051.
Blank, C. et al. (2006) "*Contribution of the PD-L1/PD-1 Pathway to T-Cell Exhaustion: An Update on Implications for Chronic Infections and Tumor Evasion*" Cancer Immunol Immunotherapy 56:739-745.
Boorjian, S.A., et al. (2008) "*T Cell Coregulatory Molecule Expression in Urothelial Cell Carcinoma: Clinicopathologic Correlations and Association with Survival*," Clin Cancer Res 14:4800-4807.
Brown et al. (1987) "*Tumor-Specific Genetically Engineered Murine/Human Chimeric Monoclonal Antibody*," Cancer Res. 47:3577-3583.
Brown, J. A. et al. (2003) "*Blockade of Programmed Death-1 Ligands on Dendritic Cells Enhances T-Cell Activation and Cytokine Production*," J. Immunol. 170:1257-1266.
Carter, L. et al. (2002) "*PD-1:PD-L Inhibitory Pathway Affects Both CD4(+) and CD8(+) T-cells and is Overcome by IL-2*," Eur. J. Immunol. 32(3):634-643.
Carter, P. et al. (1992) "*Humanization of an Anti-p185her2 Antibody for Human Cancer Therapy*," Proc. Natl. Acad. Sci. (U.S.A.) 89:4285-4289.
Cartron, G. et al. (2002) "*Therapeutic Activity of Humanized Anti-CD20 Monoclonal Antibody and Polymorphism in IgG Fc Receptor FcgammaRIIIa Gene*" Blood 99:754-758.
CAS 1036730-42-3 *Pidilizumab* ChemID Plus (Abstract).
CAS 1374853-91-4 *Nivolumab* ChemID Plus (Abstract).
CAS 946414-94-4 *Pembrolizumab* ChemID Plus (Abstract).
Castriconi et al. (2004) "*Identification of 4Ig-B7-H3 as A Neuroblastoma-Associated Molecule That Exerts a Protective Role from an NK Cell-Mediated Lysis*," Proc. Natl. Acad. Sci. (U.S.A.) 101(34):12640-12645.
Chan, C.E. et al. (2009) "*The Use of Antibodies in the Treatment of Infectious Diseases*," Singapore Med. J. 50(7):663-666.
Chapoval, A. et al. (2001) "*B7-H3: A Costimulatory Molecule for T Cell Activation and IFN-γ Production*," Nature Immunol. 2:269-274.
Chavin, G., et al. (2009) "*Expression of Immunosuppressive B7-H3 ligand by hormone-treated prostate cancer tumors and metastases*," Clin Cancer Res 15:2174-80.
Chen, Y. et al. (2005) "*Expression of B7-H1 in Inflammatory Renal Tubular Epithelial Cells*," Nephron. Exp. Nephrol. 102:e81-e92.
Clinical Trials NCT 02475213, Sep. 22, 2015, "*Safety Study of MGA271 in Combination with Pembrolizumab in Refractory Cancer*".
Co, M. S. et al. (1991) "*Humanized Antibodies for Antiviral Therapy*," Proc. Natl. Acad. Sci. (U.S.A.) 88:2869-2873.
Co, M.S. et al. (1992) "*Chimeric and Humanized Antibodies with Specificity for the CD33 Antigen*," J. Immunol. 148:1149-1154.
Collins, M. et al. (2005) "*The B7 Family of Immune-Regulatory Ligands*," Genome Biol. 6:223.1-223.7.
Crispen, P.L., et al. (2008) "*Tumor cell and tumor vasculature expression of B7-H3 predict survival in clear cell renal cell Carcinoma*," Clin Cancer Res 14:5150-7.
Daugherty et al. (1991) "*Polymerase Chain Reaction Facilitates the Cloning, CDR-Grafting, and Rapid Expression of a Murine Monoclonal Antibody Directed Against the CD18 Component of Leukocyte Integrins*," Nucl. Acids Res. 19:2471-2476.
de Haij, S. et al. (2005) "*Renal Tubular Epithelial Cells Modulate T-Cell Responses via ICOS-L and B7-H1*" Kidney Int. 68:2091-2102.
Dondelinger, M. et al. (2018) "*Understanding the Significance and Implications of Antibody Numbering and Antigen-Binding Surface/Residue Definition*." Front. Immunol. 9:Article 2278 (pp. 1-15).
Dong, H. (2003) "*B7-H1 Pathway and Its Role in the Evasion of Tumor Immunity*," J. Mol. Med. 81:281-287.
Flies, D.B. et al. (2007) "*The New B7s: Playing a Pivotal Role in Tumor Immunity*," J. Immunother. 30(3):251-260.
Freeman, G.J. et al. (2000) "*Engagement of the PD-1 Immunoinhibitory Receptor by a Novel B7 Family Member Leads to Negative Regulation of Lymphocyte Activation*," J. Exp. Med. 192:1-9.
Fukushima, A. et al. (2007) "*B7-H3 Regulates the Development of Experimental Allergic Conjunctivitis in Mice*," Immunol. Lett. 113:52-57.
Ganesan, A. (2006) "*Solid-Phase Synthesis in The Twenty-First Century*," Mini Rev. Med. Chem. 6(1):3-10.
Gorman, S. D. et al. (1991) "*Reshaping a Therapeutic CD4 Antibody*," Proc. Natl. Acad. Sci. (U.S.A.) 88:4181-4185.
Gregorio, A., et al. (2008) "*Small round blue cell tumours: diagnostic and prognostic usefulness of the expression of B7-H3 surface molecule*," Histopathology 53:73-80.

(56) References Cited

OTHER PUBLICATIONS

Hashiguchi, M. et al. (2008) "*Triggering Receptor Expressed on Myeloid Cell-Like Transcript 2 (TLT-2) is a Counter-Receptor for B7-H3 and Enhances T Cell Responses*," Proc. Natl. Acad. Sci. (U.S.A.) 105(30):10495-10500.
Hofmeyer, K. et al. (2008) "*The Contrasting Role of B7-H3*," Proc. Natl. Acad. Sci. (U.S.A.) 105(30):10277-10278.
Houghten, R.A. (1985) "*General Method for the Rapid Solid-Phase Synthesis of Large Numbers of Peptides: Specificity of Antigen-Antibody Interaction at the Level of Individual Amino Acids*," Proc. Natl. Acad. Sci. (U.S.A.) 82(15):5131-5135.
Ishida, Y. et al. (1992) "*Induced Expression of PD-1, A Novel Member of the Immunoglobulin Gene Superfamily, Upon Programmed Cell Death*," EMBO J. 11:3887-3895.
Jennings, V.M. (1995) "*Review of Selected Adjuvants Used in Antibody Production*," ILAR J. 37(3):119-125.
Jones et al. (1986) "*Replacing the Complementarity-Determining Regions in a Human Antibody With Those From a Mouse*," Nature 321:522-525.
Kabat, E.A. et al. (1971) "*Attempts to Locate Residues in Complementarity-Determining Regions of Antibody Combining Sites That Make Contact With Antigen*," Proc. Natl. Acad. Sci. (U.S.A.) 73(2):617-619.
Katayama, A., et al. (2011) "*Expression of B7-H3 in hypopharyngeal squamous cell carcinoma as a predictive indicator for tumor metastasis and prognosis*," Int J Oncol 38:1219-1226.
Kettleborough, C. A. et al. (1991) "*Humanization of a Mouse Monoclonal Antibody by CDR-Grafting: The Importance of Framework Residues on Loop Conformation*," Protein Engineering 4:773-3783.
Khawli, L.A. et al. (2008) "Cytokine, Chemokine, and Co-Stimulatory Fusion Proteins for the Immunotherapy of Solid Tumors," Exper. Pharmacol. 181:291-328.
King, R.G. et al. (2006) "*Trem-Like Transcript 2 is Expressed on Cells of The Myeloid/Granuloid and B Lymphoid Lineage and is Up-Regulated in Response to Inflammation*," J. Immunol. 176:6012-6021.
Kleponis et al. (2015) "*Fueling the Engine and Releasing the Break: Combinational Therapy of Cancer Vaccines and Immune Checkpoint Inhibitors*," Cancer Biol Med 12:201-208.
Klesney-Tait, J. et al. (2006) "*The TREM Receptor Family and Signal Integration*," Nat. Immunol. 7:1266-1273.
Kohler, G. et al. (1975) "*Continuous Cultures of Fused Cells Secreting Antibody of Predefined Specificity*," Nature 256:495-497.
Latchman, Y. et al. (2001) "*PD-L2 is a Second Ligand for PD-1 and Inhibits T-Cell Activation*," Nat. Immunol 2:261-268.
Lefranc, G. et al., (1979) "Gm, Am and Km Immunoglobulin Allotypes of Two Populations in Tunisia" Hum. Genet. 50, 199-211.
Linsley, P.S. et al. (2009) "*The Clinical Utility of Inhibiting CD28-Mediated Co-Stimulation*," Immunolog. Rev. 229:307-321.
Lobuglio et al. (1989) "*Mouse/Human Chimeric Monoclonal Antibody in Man: Kinetics and Immune Response*," Proc. Natl. Acad. Sci. (U.S.A.) 86:4220-4224.
Loke, P. et al. (2004) "*Emerging Mechanisms of Immune Regulation: The Extended B7 Family and Regulatory T Cells*." Arthritis Res. Ther. 6:208-214.
Lonberg, N. et al. (1995) "*Human Antibodies from Transgenic Mice*," Int. Rev. Immunol 13:65-93.
Loo, D. (2012) et al. "*Development of an FC-enhanced anti B7-H3 monoclonal antibody with potent antitumor activity*," Clinical Cancer Res. vol. 18 (14) 3834-3845.
Lu et al., (2008) "*The Effect of a Point Mutation on the Stability of Igg4 as Monitored by Analytical Ultracentrifugation*," J. Pharm. Sci. 97:960-969.
Maeda, H. et al. (1991) "*Construction of Reshaped Human Antibodies With HIV-Neutralizing Activity*," Human Antibodies Hybridoma 2:124-134.
Martin, C.R. (2010) "*Protein Sequence and Structure Analysis of Antibody Variable Domains*," In: Antibody Engineering vol. 2 (Kontermann, R. and Dübel, S. (eds.), Springer-Verlag Berlin Heidelberg, Chapter 3 (pp. 33-51).
Martin-Orozco, N. et al. (2007) "Inhibitory Costimulation and Anti-Tumor Immunity," Semin. Cancer Biol. 17(4):288-298.
Marvin et al. (2005) "*Recombinant Approaches to IgG-Like Bispecific Antibodies*," Acta Pharmacol. Sin. 26:649-658.
Mazanet, M.M. et al. (2002) "*B7-H1 is Expressed by Human Endothelial Cells and Suppresses T-Cell Cytokine Synthesis*," J. Immunol. 169:3581-3588.
Merrifield, B. (1986) "*Solid Phase Synthesis*," Science 232(4748):341-347.
Modak, S. et al. (1999) "*Disialoganglioside GD2 and Antigen 8H9: Potential Targets for Antibody-Based Immunotherapy Against Desmoplastic Small Round Cell Tumor (DSRCT) and Rhabdomyosarcoma (RMS)*," Proceedings of the American Association for Cancer Research Annual Meeting, (40):474.
Modak, S. et al. (2000) "*Radioimmunotargeting to Human Rhabdomyosarcoma Using Monoclonal Antibody 8H9*," Proc. Am. Assoc. Cancer Res.(41):724.
Modak, S. et al. (2001) "*Monoclonal Antibody 8H9 Targets a Novel Cell Surface Antigen Expressed by a Wide Spectrum of Human Solid Tumors*," Cancer Res. 61(10):4048-4054.
Nishimura, H. et al. (2000) "*Facilitation of Beta Selection and Modification of Positive Selection in the Thymus of PD-1-Deficient Mice*," J. Exp. Med. 191:891-898.
Peeters et al. (2001) "*Production of Antibodies and Antibody Fragments in Plants*," Vaccine 19:2756.
Peters, P et al., (2012) "*Engineering an Improved IgG4 Molecule with Reduced Disulfide Bond Heterogeneity and Increased Fab Domain Thermal Stability*," J. Biol. Chem., 287:24525-24533.
Petroff, M.G. et al. (2002) "*B7 Family Molecules: Novel Immunomodulators at the Maternal-Fetal Interface*," Placenta 23:S95-S101.
Pollock et al. (1999) "*Transgenic Milk as a Method for the Production of Recombinant Antibodies*," J. Immunol Methods 231:147-157.
Prasad, D.V. et al. (2004) "*Murine B7-H3 is a Negative Regulator of T Cells*," J. Immunol. 173:2500-2506.
Ridgway et al. (1996) "'*Knobs-Into-Holes' Engineering of Antibody CH3 Domains for Heavy Chain Heterodimerization*," Protein Engr. 9:617-621.
Riechmann, L. et al. (1988) "*Reshaping Human Antibodies for Therapy*," Nature 332:323-327.
Sato, K. et al. (1993) "*Reshaping a Human Antibody to Inhibit the Interleukin 6-dependent Tumor Cell Growth*", Cancer Res 53:851-856.
Sharpe, A.H. et al. (2002) "*The B7-CD28 Superfamily*," Nature Rev. Immunol. 2:116-126.
Shaw et al. (1987) "*Characterization of a Mouse/Human Chimeric Monoclonal Antibody (17-1A) to a Colon Cancer Tumor-Associated Antigen*," J. Immunol. 138:4534-4538.
Steinberger, P. et al. (2004) "*Molecular Characterization of Human 4Ig-B7-H3, a Member of the B7 Family with Four Ig-Like Domains*," J. Immunol. 172(4): 2352-2359.
Subudhi, S.K. et al. (2005) "*The Balance of Immune Responses: Costimulation verse Coinhibition*," J. Mol. Med. 83:193-202.
Sun, J., et al. (2010) "*Clinical Significance and Regulation of the Costimulatory Molecule B7-H3 in Human Colorectal Carcinoma*," Cancer Immunol Immunotherapy 59(8):1163-1171.
Sun, M. et al. (2002) "*Characterization of Mouse and Human B7-H3 Genes*," J. Immunol. 168:6294-6297.
Sun, Y., et al. (2006) "*B7-H3 and B7-H4 expression in non-small-cell lung cancer*," Lung Cancer 53:143-151.
Tekle, C., et al. (2012) "*B7-H3 contributes to the metastatic capacity of melanoma cells by modulation of known metastasis-associated genes*," Int J Cancer 130:2282-2290.
Tempest, P.R. et al. (1991) "*Reshaping a Human Monoclonal Antibody to Inhibit Human Respiratory Syncytial Virus Infection in vivo*," Bio/Technology 9:266-271.
Teplyakov, A. et al. (2014) "*Canonical Structures of Short CDR-L3 in Antibodies*," Proteins 82:1668-1673.

(56) References Cited

OTHER PUBLICATIONS

Verhoeyen, M. et al. (1988) "*Reshaping Human Antibodies: Grafting an Antilysozyme Activity*," Science 239:1534-1536.
Wang, L., et al. (2013) "*B7-H3 Mediated Tumor Immunology: Friend or Foe*?," Int. J. Cancer. 134:2764-2771.
Weng, W.K. et al. (2003) "*Two Immunoglobulin G Fragment C Receptor Polymorphisms Independently Predict Response to Rituximab in Patients with Follicular Lymphoma*," J Clin Oncol. 21(21):3940-3947.
Winter et al. (1991) "*Man-made Antibodies*," Nature 349:293-299.
Winter, G. et al. (1994) "*Making Antibodies by Phage Display Technology*," Annu. Rev. Immunol. 12.433-455.
Wu et al. (1987) "*Receptor-Mediated in Vitro Gene Transformation by a Soluble DNA Carrier System*," J. Biol. Chem. 262:4429-4432.
Wu, C.P., et al. (2006) "*Relationship between costimulatory molecule B7-H3 expression and gastric carcinoma histology and prognosis*," World J Gastroenterol 12:457-459.
Wu, T.T. et al. (1975) "*Similarities Among Hypervariable Segments of Immunoglobulin Chains*," Proc. Natl. Acad. Sci. (U.S.A.) 72(12):5107-5110.
Xie et al. (2005) "*A New Format of Bi-specific Antibody: Highly Efficient Heterodimerization, Expression and Tumor Cell Lysis*," J. Immunol. Methods 296:95-101.
Xu, H. et al. (2009) "*MicroRNA miR-29 Modulates Expression of Immunoinhibitory Molecule B7-H3: Potential Implications for Immune Based Therapy of Human Solid Tumors*," Cancer Res. 69(15):5275-6281.
Yamazaki, T. et al. (2002) "*Expression of Programmed Death 1 Ligands by Murine T-Cells and APC*," J. Immunol. 169:5538-5545.
Yi. K.H. et al. (2009) "*Fine Tuning the Immune Response Through B7-H3 and B7-H4*," Immunol. Rev. 229:145-151.
Zang, X. et al. (2003) "*B7x: A Widely Expressed B7 Family Member That Inhibits T Cell Activation*," Proc. Natl. Acad. Sci. (U.S.A.) 100:10388-10392.
Zang, X. et al. (2007) "*The B7 Family and Cancer Therapy: Costimulation and Coinhibition*," Clin Cancer Res. 13:5271-5279.
Zang, X., et al. (2007) "*B7-H3 and B7x are Highly Expressed in Human Prostate Cancer and associated with Disease Spread and Poor Outcome*", Proc Natl Acad Sci USA 104:19458-19463.
Zang, X., et al. (2010) "*Tumor Associated Endothelial Expression of B7-H3 {redicts Survival in Ovarian Carcinomas*," Mod Pathol Aug. 23(8):1104-1112.
Anonymous (2014) "*B7-H3 and PD-1: Are All Checkpoint Inhibitors Created Equal*?" Seeking Alpha, (https://seekingalpha.com/article/2755545-b7-h3-and-pdminus-1-are-all-checkpoint-inhibitors-created-equal) web article printout; pp. 1-10.
Clinical Trials: NCT02475213 [online], ClinicalTrials.gov Archive. Sep. 22, 2015, pp. 1-4.
International Search Report PCT/US2016/055750 (WO 2017/062619) (dated 2017) (5 pages).
Written Opinion of the International Searching Authority PCT/US2016/055750 (WO 2017/062619) (dated 2017) (6 pages).
Mexican Application No. MX/a/2018/004177 Office Action dated Jul. 21, 2021.

* cited by examiner

COMBINATION THERAPY FOR THE TREATMENT OF CANCER

CROSS-REFERENCE TO RELATED APPLICATIONS

This application is a § 371 National Stage Application of PCT/US2016/055750 (filed Oct. 6, 2016), which application claims priority to U.S. Patent Application Serial No. 62/239,020 (filed Oct. 8, 2015), each of which applications is herein incorporated by reference in its entirety.

REFERENCE TO SEQUENCE LISTING

This application includes one or more Sequence Listings pursuant to 37 C.F.R. 1.821 et seq., which are disclosed in computer-readable media (file name: 1301_129PCT_ST25.txt, created on Sep. 24, 2016, and having a size of 89,867 bytes), which file is herein incorporated by reference in its entirety.

FIELD OF THE INVENTION

The present invention is directed to a combination therapy involving the administration of a first molecule that specifically binds to human B7-H3 and a second molecule that that specifically binds to human PD-1 to a subject for the treatment of cancer and/or inflammation. The invention also concerns pharmaceutical compositions that comprise a first molecule that specifically binds to human B7-H3 and a second molecule that specifically binds to human PD-1 that are capable of mediating, and more preferably enhancing, the activation of the immune system against cancer cells that are associated with any of a variety of human cancers. The invention also relates to the use of such pharmaceutical compositions to treat cancer and other diseases in recipient subjects.

BACKGROUND OF THE INVENTION

The growth and metastasis of tumors depends to a large extent on their capacity to evade host immune surveillance and overcome host defenses. Most tumors express antigens that can be recognized to a variable extent by the host immune system, but in many cases, an inadequate immune response is elicited because of the ineffective activation of effector T cells (Khawli, L. A. et al. (2008) "*Cytokine. Chemokine, and Co-Stimulatory Fusion Proteins for the Immunotherapy of Solid Tumors*," Exper. Pharmacol. 181: 291-328).

A. B7 Superfamily and B7-H3

B7 family members are immunoglobulin superfamily members with an immunoglobulin-V-like and an immunoglobulin-C-like domain (e.g., IgV-IgC) (Sharpe, A. H. et al. (2002) "*The B7-CD28 Superfamily*," Nature Rev. Immunol. 2:116-126). The IgV and IgC domains of B7-family members are each encoded by single exons, with additional exons encoding leader sequences, transmembrane and cytoplasmic domains. The cytoplasmic domains are short, ranging in length from 19 to 62 amino acid residues and can be encoded by multiple exons (Collins, M. et al. (2005) "*The B7 Family Of Immune-Regulatory Ligands*," Genome Biol. 6:223.1-223.7). Members of the B7 family are predicted to form back-to-back, non-covalent homodimers at the cell surface, and such dimers have been found with respect to B7-1 (CD80) and B7-2 (CD86). B7-1 (CD80) and B7-2 (CD86) exhibit dual specificity for the stimulatory CD28 receptor and the inhibitory CTLA-4 (CD152) receptor (Sharpe, A. H. et al. (2002) "*The B7-CD28 Superfamily*," Nature Rev. Immunol. 2:116-126).

B7-H3 is unique in that the major human form contains two extracellular tandem IgV-IgC domains (i.e., IgV-IgC-IgV-IgC) (Collins, M. et al. (2005) "*The B7 Family Of Immune-Regulatory Ligands*," Genome Biol. 6:223.1-223.7). Although initially thought to comprise only 2 Ig domains (IgV-IgC) (Chapoval, A. et al. (2001) "B7-H3*; A Costimulatory Molecule For T Cell Activation and IFN-γ Production*," Nature Immunol. 2:269-274; Sun, M. et al. (2002) "*Characterization of Mouse and Human B7-H3 Genes*," J. Immunol. 168:6294-6297) a four immunoglobulin extracellular domain variant ("4Ig-B7-H3") has been identified and found to be the more common human form of the protein (Sharpe, A. H. et al. (2002) "*The B7-CD28 Superfamily*," Nature Rev. Immunol. 2:116-126). However, the natural murine form (2Ig) and the human 4Ig form exhibit similar function (Hofmeyer, K. et al. (2008) "*The Contrasting Role Of B7-H3*," Proc. Natl. Acad. Sci. (U.S.A.) 105(30): 10277-10278). The 4Ig-B7-H3 molecule inhibits the natural killer cell-mediated lysis of cancer cells (Castriconi, R. et al. "*Identification Of 4Ig-B7-H3 As A Neuroblastoma-Associated Molecule That Exerts A Protective Role From An NK Cell-Mediated Lysis*," Proc. Natl. Acad. Sci. (U.S.A.) 101(34): 12640-12645). The human B7-H3 (2Ig form) has been found to promote T-cell activation and IFN-γ production by binding to a putative receptor on activated T cells (Chapoval, A. et al. (2001) "B7-H3*: A Costimulatory Molecule For T Cell Activation and IFN-γ Production*," Nature Immunol. 2:269-274; Xu, H. et al. (2009) "*MicroRNA miR-29 Modulates Expression of Immunoinhibitory Molecule B7-H3: Potential Implications for Immune Based Therapy of Human Solid Tumors*," Cancer Res. 69(15):5275-6281). Both B7-H4 and B7-H1 are potent inhibitors of immune function when expressed on tumor cells (Flies, D. B. et al. (2007) "*The New B7s: Playing a Pivotal Role in Tumor Immunity*," J. Immunother. 30(3): 251-260).

The mode of action of B7-H3 is complex, as the protein mediates both T cell costimulation and co-inhibition (Hofmeyer, K. et al. (2008) "*The Contrasting Role Of B7-H3*," Proc. Natl. Acad. Sci. (U.S.A.) 105(30):10277-10278; Martin-Orozco, N. et al. (2007) "*Inhibitory Costimulation And Anti-Tumor Immunity*," Semin. Cancer Biol. 17(4):288-298; Subudhi, S. K. et al. (2005) "*The Balance Of Immune Responses: Costimulation Verse Coinhibition*," J. Mol. Med. 83:193-202). B7-H3 binds to (TREM)-like transcript 2 (TLT-2) and co-stimulates T cell activation, but also binds to as yet unidentified receptor(s) to mediate co-inhibition of T cells. In addition, B7-H3, through interactions with unknown receptor(s) is an inhibitor for natural killer cells and osteoblastic cells (Hofmeyer, K. et al. (2008) "*The Contrasting Role Of B7-H3*," Proc. Natl. Acad. Sci. (U.S.A.) 105(30):10277-10278). The inhibition may operate through interactions with members of the major signaling pathways through which T cell receptor (TCR) regulates gene transcription (e.g., NFTA, NF-κB, or AP-1 factors).

B7-H3 co-stimulates CD4+ and CD8+ T-cell proliferation. B7-H3 also stimulates IFN-γ production and CD8+ lytic activity (Chapoval, A. et al. (2001) "*B7-H3: A Costimulatory Molecule For T Cell Activation and IFN-γ Production*," Nature Immunol. 2:269-274; Sharpe, A. H. et al. (2002) "*The B7-CD28 Superfamily*," Nature Rev. Immunol. 2:116-126). However, the protein also possibly acts through NFAT (nuclear factor for activated T cells), NF-κB (nuclear factor kappa B), and AP-1 (Activator Protein-1) factors to inhibit T-cell activation (Yi. K. H. et al. (2009) "*Fine Tuning The Immune Response Through B7-H3 And B7-H4*," Immunol. Rev. 229:145-151). B7-H3 is also believed to inhibit Th1, Th2, or Th17 in vivo (Prasad, D. V. et al. (2004) "*Murine B7-H3 Is A Negative Regulator Of T Cells*," J. Immunol. 173:2500-2506; Fukushima, A. et al. (2007) "*B7-H3 Regulates The Development Of Experimental Allergic Conjunctivitis In Mice*," Immunol. Lett. 113:52-57; Yi. K. H. et al. (2009) "*Fine Tuning The Immune Response Through B7-H3 And B7-H4*," Immunol. Rev. 229:145-151). Several independent studies have shown that human malignant tumor cells exhibit a marked increase in expression of B7-H3 protein and that this increased expression was associated with increased disease severity (Zang, X. et al. (2007) "*The B7 Family And Cancer Therapy: Costimulation And Coinhibition*," Clin. Cancer Res. 13:5271-5279), suggesting that B7-H3 is exploited by tumors as an immune evasion pathway (Hofmeyer, K. et al. (2008) "*The Contrasting Role Of B7-H3*," Proc. Natl. Acad. Sci. (U.S.A.) 105(30): 10277-10278).

Molecules that block the ability of a B7 molecule to bind to a T-cell receptor (e.g., CD28) inhibit the immune system and have been proposed as treatments for autoimmune disease (Linsley, P. S. et al. (2009) "*The Clinical Utility Of Inhibiting CD28-Mediated Co-Stimulation*," Immunolog. Rev. 229:307-321). Neuroblastoma cells expressing 4Ig-B7-H3 treated with anti-4Ig-B7-H3 antibodies were more susceptible to NK cells. However, it is unclear whether this activity can be attributed to only antibodies against the 4Ig-B7-H3 form because all reported antibodies raised against the 4Ig-B7-H3 also bound the two Ig-like form of B7H3 (Steinberger, P. et al. (2004) "*Molecular Characterization of Human 4Ig-B7-H3, a Member of the B7 Family with Four Ig-Like Domains*," J. Immunol. 172(4): 2352-2359 and Castriconi et al. (2004) "*Identification Of 4Ig-B7-H3 As A Neuroblastoma-Associated Molecule That Exerts A Protective Role From An NK Cell-Mediated Lysis*," Proc. Natl. Acad. Sci. (U.S.A.) 101(34): 12640-12645).

B7-H3 is not expressed on resting B or T cells, monocytes, or dendritic cells, but it is induced on dendritic cells by IFN-γ and on monocytes by GM-CSF (Sharpe, A. H. et al. (2002) "*The B7-CD28 Superfamily*," Nature Rev. Immunol. 2:116-126). The receptor(s) that bind B7-H3 have not been fully characterized. Early work suggested one such receptor would need to be rapidly and transiently up-regulated on T cells after activation (Loke, P. et al. (2004) "*Emerging Mechanisms Of Immune Regulation: The Extended B7 Family And Regulatory T Cells*." Arthritis Res. Ther. 6:208-214). Recently, the (TREM)-like transcript 2 (TLT-2, or TREML2) receptor (King, R. G. et al. (2006) "*Trem-Like Transcript 2 Is Expressed On Cells Of The Myeloid/Granuloid And B Lymphoid Lineage And Is Up-Regulated In Response To Inflammation*," J. Immunol. 176: 6012-6021; Klesney-Tait, J. et al. (2006) "*The TREM Receptor Family And Signal Integration*," Nat. Immunol. 7:1266-1273; Yi. K. H. et al. (2009) "Fine *Tuning The Immune Response Through B7-H3 And B7-H4*," Immunol. Rev. 229:145-151), which is expressed on myeloid cells has been shown to be capable of binding B7-H3, and of thereby co-stimulating the activation of CD8+ T cells in particular (Zang, X. et al. (2003) "*B7x: A Widely Expressed B7 Family Member That Inhibits T Cell Activation*," Proc. Natl. Acad. Sci. (U.S.A.) 100:10388-10392; Hashiguchi, M. et al. (2008) "*Triggering Receptor Expressed On Myeloid Cell-Like Transcript 2 (TLT-2) Is A Counter-Receptor For B7-H3 And Enhances TCell Responses*," Proc. Natl. Acad. Sci. (U.S.A.) 105(30): 10495-10500; Hofmeyer, K. et al. (2008) "*The Contrasting Role Of B7-H3*," Proc. Natl. Acad. Sci. (U.S.A.) 105(30): 10277-10278).

In addition to its expression on neuroblastoma cells, human B7-H3 is overexpressed in a wide range of cancers and cultured cancer stem-like cells. In particular, B7-H3 is broadly overexpressed on many malignant neoplasms including: SCCHN, where the level is directly proportional to the development of distal metastases and decreased survival (Katayama, A., et al. (2011) "*Expression of B7-H3 in hypopharyngeal squamous cell carcinoma as a predictive indicator for tumor metastasis and prognosis*," Int J Oncol 38:1219-26); bladder cancer (Boorjian, S. A., et al. (2008) "*T Cell Coregulatory Molecule Expression in Urothelial Cell Carcinoma: Clinicopathologic Correlations and Association with Survival*," Clin Cancer Res 14:4800-7); prostate cancer, where expression of B7-H3 is associated with metastatic behavior and poor outcome (Chavin, G., et al. (2009) "*Expression of immunosuppresive B7-H3 ligand by hormone-treated prostate cancer tumors and metastases* '," Clin Cancer Res 15:2174-80; Zang, X., et al. (2007) "*B7-H3 and B7x are highly expressed in human prostate cancer and associated with disease spread and poor outcome*," Proc Natl Acad Sci USA 104:19458-63); renal cell carcinoma, where B7-H3 is broadly expressed in tumor vasculature (Crispen, P. L., et al. (2008) "*Tumor cell and tumor vasculature expression of B7-H3 predict survival in clear cell renal cell Carcinoma*," Clin Cancer Res 14:5150-7); ovarian cancer (Zang, X., et al. (2010) "*Tumor associated endothelial expression of B7-H3 predicts survival in ovarian carcinomas*," Mod Pathol 2010 May 21); colorectal cancer (Sun, J., et al. (2010) "*Clinical significance and regulation of the costimulatory molecule B7-H3 in human colorectal carcinoma*," Cancer Immunol Immunother, March 24); gastric cancer (Wu, C. P., et al. (2006) "*Relationship between costimulatory molecule B7-H3 expression and gastric carcinoma histology and prognosis*," World J Gastroenterol 12:457-9); non-small cell lung cancer, where higher levels on the primary tumor are associated with a higher likelihood of metastatic disease (Sun, Y., et al. (2006) "*B7-H3 and B7-H4 expression in non-small-cell lung cancer*," Lung Cancer 53:143-51); glioblastoma (Modak, S., et al. (2001) "*Monoclonal antibody 8H9 targets a novel cell surface antigen expressed by a wide spectrum of human solid tumors*," Cancer Res 61:4048-54); melanoma, where higher levels are associated with higher tumor stage and shorter survival (Tekle, C., et al. (2012) "*B7-H3 contributes to the metastatic capacity of melanoma cells by modulation of known metastasis-associated genes*," Int J Cancer 130:2282-90; Wang, L., et al. (2013) "*B7-H3 mediated tumor immunology: Friend or foe*?," Int J Cancer September 7); and certain small round blue cell tumors of childhood including neuroblastoma and rhabdomyosarcoma (Gregorio, A., et al. (2008) "*Small round blue cell tumours: diagnostic and prognostic usefulness of the expression of B7-H3 surface molecule*," Histopathology 53:73-80).

B. PD-1

Programmed Death-1 ("PD-1") is an approximately 31 kD type I membrane protein member of the extended CD28/CTLA4 family of T-cell regulators that broadly negatively regulates immune responses (Ishida, Y. et al. (1992) "*Induced Expression Of PD-1. A Novel Member Of The Immunoglobulin Gene Superfamily. Upon Programmed Cell Death*," EMBO J. 11:3887-3895; United States Patent Application Publication No. 2007/0202100; 2008/0311117; 2009/00110667; U.S. Pat. Nos. 6,808,710; 7,101,550; 7,488,802; 7,635,757; 7,722,868; PCT Publication No. WO 01/14557).

PD-1 is expressed on activated T-cells, B-cells, and monocytes (Agata, Y. et al. (1996) "*Expression Of The PD-1 Antigen On The Surface Of Stimulated Mouse T And B Lymphocytes*," Int. Immunol. 8(5):765-772; Yamazaki, T. et al. (2002) "*Expression Of Programmed Death 1 Ligands By Murine T-Cells And APC*," J. Immunol. 169:5538-5545) and at low levels in natural killer (NK) T-cells (Nishimura, H. et al. (2000) "*Facilitation Of Beta Selection And Modification Of Positive Selection In The Thymus Of PD-I-Deficient Mice*," J. Exp. Med. 191:891-898; Martin-Orozco, N. et al. (2007) "*Inhibitory Costimulation And Anti-Tumor Immunity*," Semin. Cancer Biol. 17(4):288-298).

The extracellular region of PD-1 consists of a single immunoglobulin (Ig)V domain with 23% identity to the equivalent domain in CTLA4 (Martin-Orozco, N. et al. (2007) "*Inhibitory Costimulation And Anti-Tumor Immunity*." Semin. Cancer Biol. 17(4):288-298). The extracellular IgV domain is followed by a transmembrane region and an intracellular tail. The intracellular tail contains two phosphorylation sites located in an immunoreceptor tyrosine-based inhibitory motif and an immunoreceptor tyrosine-based switch motif, which suggests that PD-1 negatively regulates TCR signals (Ishida, Y. et al. (1992) "*Induced Expression Of PD-1. A Novel Member Of The Immunoglobulin Gene Superfamily. Upon Programmed Cell Death*," EMBO J. 11:3887-3895; Blank, C. et al. (2006) "*Contribution Of The PD-L1/PD-Pathway To T-Cell Exhaustion: An Update On Implications For Chronic Infections And Tumor Evasion Cancer*," Immunol. Immunother. 56(5):739-745).

PD-1 mediates its inhibition of the immune system by binding to PD-L1 and PD-L2 (Flies, D. B. et al. (2007) "*The New B7s: Playing a Pivotal Role in Tumor Immunity*," J. Immunother. 30(3):251-260; U.S. Pat. Nos. 6,803,192; 7,794,710; United States Patent Application Publication Nos. 2005/0059051; 2009/0055944; 2009/0274666; 2009/0313687; PCT Publication Nos. WO 01/39722; WO 02/086083).

PD-L1 and PD-L2 are broadly expressed on the surfaces of human and murine tissues, such as heart, placenta, muscle, fetal liver, spleen, lymph nodes, and thymus as well as murine liver, lung, kidney, islets cells of the pancreas and small intestine (Martin-Orozco, N. et al. (2007) "*Inhibitory Costimulation And Anti-Tumor Immunity*," Semin. Cancer Biol. 17(4):288-298). In humans, PD-L1 protein expression has been found in human endothelial cells (Chen, Y. et al. (2005) "*Expression of B7-H1 in Inflammatory Renal Tubular Epithelial Cells*," Nephron. Exp. Nephrol. 102:e81-e92; de Haij, S. et al. (2005) "*Renal Tubular Epithelial Cells Modulate T-Cell Responses Via ICOS-L And B7-H1*" Kidney Int. 68:2091-2102; Mazanet, M. M. et al. (2002) "*B7-H1 Is Expressed By Human Endothelial Cells And Suppresses T-Cell Cytokine Synthesis*," J. Immunol. 169:3581-3588), myocardium (Brown, J. A. et al. (2003) "*Blockade Of Programmed Death-1 Ligands On Dendritic Cells Enhances T-Cell Activation And Cytokine Production*," J. Immunol. 170:1257-1266), syncyciotrophoblasts (Petroff, M. G. et al. (2002) "*B7 Family Molecules: Novel Immunomodulators At The Maternal-Fetal Interface*," Placenta 23:S95-S101). The molecules are also expressed by resident macrophages of some tissues, by macrophages that have been activated with interferon (IFN)-γ or tumor necrosis factor (TNF)-α (Latchman, Y. et al. (2001) "*PD-L2 Is A Second Ligand For PD-1 And Inhibits T-Cell Activation*," Nat. Immunol 2:261-268), and in tumors (Dong, H. (2003) "*B7-H1 Pathway And Its Role In The Evasion Of Tumor Immunity*." J. Mol. Med. 81:281-287).

The interaction between PD-L1 and PD-1 has been found to provide a crucial negative costimulatory signal to T- and B-cells (Martin-Orozco, N. et al. (2007) "*Inhibitory Costimulation And Anti-Tumor Immunity*," Semin. Cancer Biol. 17(4):288-298) and functions as a cell death inducer (Ishida, Y. et al. (1992) "*Induced Expression OfPD-1. A Novel Member Of The Immunoglobulin Gene Superfamily. Upon Programmed Cell Death*," EMBO J. 1:3887-3895; Subudhi, S. K. et al. (2005) "*The Balance Of Immune Responses: Costimulation Verse Coinhibition*," J. Molec. Med. 83:193-202). More specifically, interaction between low concentrations of the PD-1 receptor and the PD-L1 ligand has been found to result in the transmission of an inhibitory signal that strongly inhibits the proliferation of antigen-specific CD8+ T-cells; at higher concentrations the interactions with PD-1 do not inhibit T-cell proliferation but markedly reduce the production of multiple cytokines (Sharpe, A. H. et al. (2002) "*The B7-CD28 Superfamily*," Nature Rev. Immunol. 2:116-126). T-cell proliferation and cytokine production by both resting and previously activated CD4 and CD8 T-cells, and even naive T-cells from umbilical-cord blood, have been found to be inhibited by soluble PD-L1-Fc fusion proteins (Freeman, G. J. et al. (2000) "*Engagement Of The PD-1Immunoinhibitory Receptor By A Novel B7 Family Member Leads To Negative Regulation Of Lymphocyte Activation*," J. Exp. Med. 192:1-9; Latchman, Y. et al. (2001) "*PD-L2 Is A Second Ligand For PD-1 And Inhibits T-Cell Activation*," Nature Immunol. 2:261-268; Carter, L. et al. (2002) "*PD-1:PD-L Inhibitory Pathway Affects Both CD4(+) and CD8(+) T-cells And Is Overcome By IL-2*," Eur. J. Immunol. 32(3):634-643; Sharpe, A. H. et al. (2002) "*The B7-CD28 Superfamily*," Nature Rev. Immunol. 2:116-126).

The role of PD-L1 and PD-1 in inhibiting T-cell activation and proliferation has suggested that these biomolecules might serve as therapeutic targets for treatments of inflammation and cancer. Thus, the use of anti-PD-1 antibodies to treat infections and tumors and up-modulate an adaptive immune response has been proposed (see, United States Patent Application Publication Nos. 2010/0040614; 2010/0028330; 2004/0241745; 2008/0311117; 2009/0217401; U.S. Pat. Nos. 7,521,051; 7,563,869; 7,595,048; PCT Publications Nos. WO 2004/056875; WO 2008/083174). Antibodies capable of specifically binding to PD-1 have been reported by Agata, T. et al. (1996) "Expression Of The PD-1 *Antigen On The Surface Of Stimulated Mouse T And B Lymphocytes*," Int. Immunol. 8(5):765-772; and Berger, R. et al. (2008) "*Phase I Safety And Pharmacokinetic Study Of CT-011. A Humanized Antibody Interacting With PD-1. In Patients With Advanced Hematologic Malignancies*," Clin. Cancer Res. 14(10):3044-3051 (see, also, U.S. Pat. Nos. 8,008,449 and 8,552,154; US Patent Publication Nos. 2007/0166281; 2012/0114648; 2012/0114649; 2013/0017199; 2013/0230514 and 2014/0044738; and PCT Patent Publication Nos. WO 2003/099196; WO 2004/004771; WO 2004/056875; WO 2004/072286; WO 2006/121168; WO 2007/005874; WO 2008/083174; WO 2009/014708; WO 2009/073533; WO 2012/135408, WO 2012/145549; and WO 2013/014668).

C. B7-H3-Expressing Cancers

Overexpression of B7-H3 occurs in a wide range of cancers and cultured cancer stem-like cells. As stated above, the overexpression of B7-H3 is strongly associated with increased disease recurrence and a poor prognosis. However, B7-H3 is a potential target for anti-B7-H3 drugs, including monoclonal antibodies that target the extracellular domain of the receptor. Antibodies and other molecules that specifically bind to B7-H3 have been described (see, U.S. Pat. Nos. 8,802,091, 7,527,969; 7,368,554; 7,358,354; and 7,279,567; United States Patent Application Publications Nos. US 20090087416; US 20090022747; US 20090018315; US2008116219; US20080081346; US 20050202536; US20030103963; US20020168762; PCT Publications Nos. WO 2011/109400; WO 2008/116219; WO 2006/016276; WO 2004/093894; WO 04/001381; WO 2002/32375; WO 2002/10187 and WO 2001/094413; EP 1292619B; Modak, S. et al. (March 1999) "*Disialoganglioside GD2 And Antigen 8H9: Potential Targets For Antibody-Based Immunotherapy Against Desmoplastic Small Round Cell Tumor (DSRCT) And Rhabdomyosarcoma (RMS)*," Proceedings Of The American Association For Cancer Research Annual Meeting, Vol. 40:474 ($9^{0th}$ Annual Meeting Of The American Association For Cancer Research; Philadelphia, Pa., US; Apr. 10-14, 1999; Modak, S. et al. (March 2000) "*Radioimmunotargeting To Human Rhabdomyosarcoma Using Monoclonal Antibody 8H9*," Proc. Am. Assoc. Cancer Res. 41:724; Modak, S. et al. (2001) "*Monoclonal Antibody 8H9 Targets A Novel Cell Surface Antigen Expressed By A Wide Spectrum Of Human Solid Tumors*," Cancer Res. 61(10):4048-4054; Steinberger, P. et al. (2004) "*Molecular Characterization of Human 4Ig-B7-H3, a Member of the B7 Family with Four Ig-Like Domains*," J. Immunol. 172(4):2352-2359; Xu, H. et al. (2009) "*MicroRNA miR-29 Modulates Expression of Immunoinhibitory Molecule B7-H3: Potential Implications for Immune Based Therapy of Human Solid Tumors*," Cancer Res. 69(15):5275-6281).

Despite these advances, a need remains for improved therapies for treating cancers expressing B7-H3 and of facilitating or mediating an immune response against such cancers. Although the adaptive immune system can be a potent defense mechanism against cancer and disease, it is often hampered by immune suppressive mechanisms in the tumor microenvironment, such as the expression of co-inhibitory molecules. Furthermore, co-inhibitory molecules expressed by tumor cells, immune cells, and stromal cells in the tumor milieu can dominantly attenuate T-cell responses against cancer cells. Thus, there exists a further need for novel combinations and treatment regimens that specifically recognize targets on the surface of cancer cells, and which can thereby mediate T-cell activation, simulation of an immune response and killing of cancer cells that express B7-H3. It is an object of this invention to identify such compositions and treatment regimens.

SUMMARY OF THE INVENTION

The present invention is directed to combination therapy involving the administration of a first molecule that specifically binds to human B7-H3 (i.e., a B7-H3-binding molecule) and a second molecule that that specifically binds to human PD-1 (i.e., a PD-1-binding molecule) to a subject for the treatment of cancer and inflammation. The invention also concerns pharmaceutical compositions that comprise a first molecule that specifically binds to human B7-H3 and a second molecule that specifically binds to human PD-1 that are capable of mediating, and more preferably enhancing, the activation of the immune system against cancer cells that are associated with a variety of human cancers. The invention also relates to the use of such pharmaceutical compositions to treat cancer and other diseases.

In detail, the invention provides a method of treating a cancer comprising administering to a subject in need thereof, a molecule that specifically binds to B7-H3, and a molecule that specifically binds to PD-1.

The invention particularly concerns embodiments of such methods, wherein the molecule that specifically binds to B7-H3 is an anti-B7-H3 antibody or antigen-binding fragment thereof, and the molecule that specifically binds to PD-1 is an anti-PD-1 antibody, or an antigen-binding fragment thereof.

The invention particularly concerns the embodiment of such methods wherein the anti-B7-H3 antibody, or antigen-binding fragment thereof:

(a) competes for B7-H3 binding with BRCA84D, BRCA69D, PRCA157, or with an anti-B7-H3 antibody selected from Table 5; or (b) has the three heavy chain CDRs and the three light chain CDRs of BRCA84D, hBRCA84D (1.1), hBRCA84D (2.2), hBRCA84D-2, hBRCA69D (1.1), hBRCA (2.2), or the three heavy chain CDRs and the three light chain CDRs of an anti-B7-H3 selected from Table 5; or (c) has the heavy chain variable domain and the light chain variable domain of BRCA84D, hBRCA84D (1.1), hBRCA84D (2.2), hBRCA84D-2, hBRCA69D (1.1), hBRCA (2.2), or the heavy chain variable domain and the light chain variable domain of an anti-B7-H3 selected from Table 5.

The invention particularly concerns the embodiment of such methods wherein the anti-PD-1 antibody, or antigen-binding fragment thereof:

(a) competes for PD-1 binding with nivolumab, pembrolizumab, pidilizumab, PD-1 mAb 3, PD-1 mAb 5, PD-1 mAb 6, PD-1 mAb7, PD-1 mAb 8, or with an anti-PD-1 antibody selected from Table 6; or (b) has the three heavy chain CDRs and the three light chain CDRs of nivolumab, pembrolizumab, pidilizumab, PD-1 mAb 3, PD-1 mAb 5, PD-1 mAb 6, PD-1 mAb7, PD-1 mAb 8, or the three heavy chain CDRs and the three light chain CDRs of an anti-PD-1 antibody selected from Table 6; or (c) has the heavy chain variable domain and the light chain variable domain of nivolumab, pembrolizumab, pidilizumab, PD-1 mAb 3, PD-1 mAb 5, PD-1 mAb 6, PD-1 mAb7, PD-1 mAb 8, or the heavy chain variable domain and the light chain variable domain of an anti-PD-1 antibody selected from Table 6.

The invention further concerns embodiments of such methods wherein the anti-B7-H3 antibody, or antigen-binding fragment thereof, comprises an Fc Domain, and/or the anti-PD-1 antibody, or antigen-binding fragment thereof, comprises an Fc Domain. The invention further concerns the embodiments of such methods wherein the anti-B7-H3 antibody or antigen-binding fragment thereof, comprises a variant Fc Domain having one, two, three, four, five or more modifications in the Fc Domain that enhances ADCC. The invention further concerns the embodiments of such methods wherein the Fc Domain modifications that enhance(s) ADCC comprise any one, any two, any three, any four, or all five of the substitutions L235V, F243L, R292P, Y300L and P396L. The invention further concerns the embodiments of such methods wherein the anti-PD-1 antibody or antigen-binding fragment thereof, comprises: (a) a variant Fc Domain having at least one modification in the Fc Domain that reduces or abolishes ADCC activity; or (b) an IgG4 Fc Domain. The invention further concerns the embodiments of such methods wherein the Fc Domain modifications that reduce or abolish ADCC comprise the substitution of L234A; L235A; or L234A and L235A, preferably of an IgG1 Fc Domain.

The invention further concerns embodiments of such methods, wherein the anti-B7-H3 antibody is hBRCA84D-2 and the anti-PD-1 antibody is nivolumab, pembrolizumab, pidilizumab, or PD-1 mAb 6-ISQ. The invention further concerns embodiments of such methods, wherein the anti-B7-H3 antibody is hBRCA84D-2 and the anti-PD-1 antibody, or antigen-binding fragment thereof comprises the VH and VL of nivolumab, pembrolizumab, pidilizumab, PD-1 mAb 3, PD-1 mAb 5, PD-1 mAb 6, PD-1 mAb 7, PD-1 mAb 8, or an anti-PD-1 antibody selected from Table 6.

The invention additionally concerns embodiments of such methods wherein the molecule that specifically binds to B7-H3 (particularly an anti-B7-H3 antibody) is administered at a dosage of 1-15 mg/kg body weight every week and the molecule that specifically binds to PD-1 (particularly an anti-PD-1 antibody) is administered at a fixed dosage of 200 mg every three weeks. The invention also concerns embodiments of such methods wherein the molecule that specifically binds to B7-H3 (particularly an anti-B7-H3 antibody) is administered at a dosage of 1-15 mg/kg body weight every week and the molecule that specifically binds to PD-1 (particularly an anti-PD-1 antibody) is administered at a dosage of 1-10 mg/kg body weight every two or three weeks. The invention further concerns embodiments of such methods wherein the molecule that specifically binds to B7-H3 (particularly an anti-B7-H3 antibody) is administered at a dosage of selected from 1 mg/kg, 3 mg/kg, 10 mg/kg and 15 mg/kg body weight every week and the molecule that specifically binds to PD-1 (particularly an anti-PD-1 antibody) is administered at a fixed dosage of 200 mg every three weeks. The invention further concerns embodiments of such methods wherein the molecule that specifically binds to B7-H3 (particularly an anti-B7-H3 antibody) is administered at a dosage of selected from 1 mg/kg, 3 mg/kg, 10 mg/kg and 15 mg/kg body weight every week and the molecule that specifically binds to PD-1 (particularly an anti-PD-1 antibody) is administered at a dosage of selected from 1 mg/kg, 2 mg/kg, 3 mg/kg and 10 mg/kg body weight every two or three weeks. The invention particularly concerns embodiments of such methods wherein the molecule that specifically binds to B7-H3 (particularly an anti-B7-H3 antibody) is administered at a dosage of selected from 3 mg/kg, 10 mg/kg and 15 mg/kg body weight every week and the molecule that specifically binds to PD-1 (particularly an anti-PD-1 antibody) is administered at a dosage of 2 mg/kg body weight every three weeks. The invention particularly concerns embodiments of such methods wherein the molecule that specifically binds to B7-H3 (particularly an anti-B7-H3 antibody) is administered at a dosage of selected from 3 mg/kg, 10 mg/kg and 15 mg/kg body weight every week and the molecule that specifically binds to PD-1 (particularly an anti-PD-1 antibody) is administered at a dosage of 3 mg/kg body weight every two weeks. The invention further concerns embodiments of such methods wherein the molecule that specifically binds to B7-H3 (particularly an anti-B7-H3 antibody) and the molecule that specifically binds to PD-1 (particularly an anti-PD-1 antibody) are administered by IV infusion. The invention also concerns embodiments of such methods wherein every two or three weeks the molecule that specifically binds to B7-H3 (particularly an anti-B7-H3 antibody) and the molecule that specifically binds to PD-1 (particularly an anti-PD-1 antibody) are administered with a 48-hour period.

The invention particularly concerns embodiments of such methods wherein the cancer is a cancer in which B7-H3 is expressed. Invention further concerns embodiments of such methods wherein the cancer is a squamous cell cancer of the head and neck (SCCHN), a bladder cancer, a breast cancer, a colorectal cancer, a gastric cancer, a glioblastoma, a kidney cancer, a lung cancer, a melanoma, an ovarian cancer, a pancreatic cancer, a pharyngeal cancer, a prostate cancer, a renal cell carcinoma, a small round blue cell tumor, a neuroblastoma, or a rhabdomyosarcoma, in which B7-H3 is expressed.

The invention additionally concerns embodiments of such methods further comprising the step of administering a third therapeutic agent, particularly wherein the third therapeutic agent is an anti-angiogenic agent, an anti-neoplastic agent, a chemotherapeutic agent, or a cytotoxic agent

DETAILED DESCRIPTION OF THE INVENTION

The present invention is directed to a combination therapy involving the administration of a first molecule that specifically binds to human B7-H3 and a second molecule that that specifically binds to human PD-1 to a subject for the treatment of cancer and/or inflammation. The invention also concerns pharmaceutical compositions that comprise a first molecule that specifically binds to human B7-H3 and a second molecule that specifically binds to human PD-1 that are capable of mediating, and more preferably enhancing, the activation of the immune system against cancer cells that are associated with any of a variety of human cancers. The invention also relates to the use of such pharmaceutical compositions to treat cancer and other diseases in recipient subjects.

A. Antibodies

1. Antibodies

"Antibodies" are immunoglobulin molecules capable of immunospecific binding to a target, such as a carbohydrate, polynucleotide, lipid, polypeptide, etc., (an "antigen") through at least one epitope recognition site, located in the Variable Domain of the immunoglobulin molecule. Thus, whereas the target molecule is an "antigen", the portion of the antigen that is recognized by an antibody and to which the antibody binds is an "epitope." As used herein, the term "antibody" encompasses not only intact polyclonal or monoclonal antibodies, camelized antibodies, single-chain antibodies, and anti-idiotypic (anti-Id) antibodies (including, e.g., anti-Id and anti-anti-Id antibodies to antibodies of the invention), but also mutants thereof, naturally occurring variants, fusion proteins comprising an epitope binding site of the required immunospecificity, humanized antibodies, and chimeric antibodies, and any other modified configuration of the immunoglobulin molecule that comprises an antigen recognition site of the required immunospecificity. As used herein, an "antigen-binding fragment" of an antibody is an immunoglobulin whose amino acid sequence comprises at least one epitope-binding site of an antibody specific for such antigen. As used herein, the term encompasses fragments (e.g., Fab, Fab', $F(ab')_2$ Fv), disulfide-linked bispecific Fvs (sdFv), intrabodies, and single-chain molecules (e.g., scFv). In particular, antibodies include immunoglobulin molecules and immunologically active fragments of immunoglobulin molecules, i.e., molecules that contain an epitope-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

Natural antibodies (such as IgG antibodies) are composed of two Light Chains complexed with two Heavy Chains. Each Light Chain contains a Variable Light Chain (VL) Domain and a Constant Light Chain (CL) Domain. Each heavy chain contains a Variable Heavy Chain (VH) Domain, three Heavy Chain Constant Domains (CHI, CH2 and CH3), and a Hinge Domain, which is located between the CHI and CH2 Domains. The basic structural unit of naturally occurring immunoglobulins (e.g., IgG) is thus a tetramer having two light chains and two heavy chains, usually expressed as a glycoprotein of about 150,000 Da. The amino-terminal portion of each polypeptide chain includes its Variable ("V") Domain, which is of about 100 to 110 or more amino acids, and is primarily responsible for antigen recognition. The carboxy-terminal portion of each polypeptide chain defines the chain's Constant ("C") Domain. Thus, the structure of the light chains of an IgG molecule (in the N-terminal to C-terminal direction) is: VL-CL, and the structure of the IgG heavy chains (in the N-terminals to C-terminal direction) is: VH-CH1-Hinge-CH2-CH3.

The ability of an intact, unmodified antibody (e.g., an IgG antibody) to bind an epitope of an antigen depends upon the presence of Variable Domains on the immunoglobulin light and heavy chains (i.e., the VL Domain and VH Domain, respectively). Interaction of an antibody Light Chain and an antibody heavy chain and, in particular, interaction of its VL and VH Domains forms one of the epitope-binding sites of the antibody. The Variable Domains of an IgG molecule consist of the complementarity determining regions (CDR), which contain the residues in contact with epitope, and non-CDR segments, referred to as framework segments (FR), which in general maintain the structure and determine the positioning of the CDR loops so as to permit such contacting (although certain framework residues may also contact antigen). Thus, the VL Domains have the structure (in the N-terminal to C-terminal direction): $FR_L1$-$CDR_L1$-$FR_L2$-$CDR_L2$-$FR_L3$-$CDR_L3$-$FR_L4$, and the VH Domains have the structure (in the N-terminal to C-terminal direction): $FR_H1$-$CDR_H1$-$FR_H2$-$CDR_H2$-$FR_H3$-$CDR_H3$-$FR_H4$. Polypeptides that are (or may serve as) the first, second and third CDR of an antibody Light Chain are herein respectively designated $CDR_L1$ Domain, $CDR_L2$ Domain, and $CDR_L3$ Domain. Similarly, polypeptides that are (or may serve as) the first, second and third CDR of an antibody heavy chain are herein respectively designated $CDR_H1$ Domain, $CDR_H2$ Domain, and $CDR_H3$ Domain. Thus, the terms $CDR_L1$ Domain, $CDR_L2$ Domain, $CDR_L3$ Domain, $CDR_H1$ Domain, $CDR_H2$ Domain, and $CDR_H3$ Domain are directed to polypeptides that when incorporated into a protein cause that protein to be able to bind to a specific epitope regardless of whether such protein is an antibody having light and heavy chains or a single-chain binding molecule (e.g., an scFv, a BiTe, etc.), or is another type of protein. In contrast to such antibodies, the scFv construct comprises a VL and VH Domain of an antibody contained in a single polypeptide chain wherein the Domains are separated by a flexible linker of sufficient length to allow self-assembly of the two Domains into a functional epitope-binding site. Where self-assembly of the VL and VH Domains is rendered impossible due to a linker of insufficient length (less than about 12 amino acid residues), two of the scFv constructs may interact with one another other to form a bivalent molecule in which the VL of one chain associates with the VH of the other (reviewed in Marvin et al. (2005) "*Recombinant Approaches To IgG-Like Bispecific Antibodies*." Acta Pharmacol. Sin. 26:649-658).

In addition to their known uses in diagnostics, antibodies have been shown to be useful as therapeutic agents. The last few decades have seen a revival of interest in the therapeutic potential of antibodies, and antibodies have become one of the leading classes of biotechnology-derived drugs (Chan, C. E. et al. (2009) "*The Use Of Antibodies In The Treatment Of Infectious Diseases*," Singapore Med. J. 50(7):663-666). Nearly 200 antibody-based drugs have been approved for use or are under development.

The term "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single epitope (or antigenic site). The term "monoclonal antibody" encompasses not only an intact monoclonal antibody and a full-length monoclonal antibody, but also a fragment thereof (such as an Fab, Fab', $F(ab')_2$ Fv), single-chain (scFv), a mutant thereof, a fusion protein comprising an antibody portion, a humanized monoclonal antibody, a chimeric monoclonal antibody, and any other modified configuration of an immunoglobulin molecule that comprises an antigen recognition site of the required immunospecificity and the ability to bind to an epitope. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody." Methods of making monoclonal antibodies are known in the art. One method which may be employed is the method of Kohler, G. et al. (1975) "*Continuous Cultures Of Fused Cells Secreting Antibody Of Predefined Specificity*," Nature 256:495-497 or a modification thereof. Typically, monoclonal antibodies are developed in mice, rats or rabbits. The antibodies are produced by immunizing an animal with an immunogenic amount of cells, cell extracts, or protein preparations that contain the desired epitope. The immunogen can be, but is not limited to, primary cells, cultured cell lines, cancerous cells, proteins, peptides, nucleic acids, or tissue. Cells used for immunization may be cultured for a period of time (e.g., at least 24 hours) prior to their use as an immunogen. Cells may be used as immunogens by themselves or in combination with a non-denaturing adjuvant, such as Ribi (see, e.g., Jennings, V. M. (1995) "*Review of Selected Adjuvants Used in Antibody Production*," ILAR J. 37(3): 119-125).

In general, cells should be kept intact and preferably viable when used as immunogens. Intact cells may allow antigens to be better detected than ruptured cells by the immunized animal. Use of denaturing or harsh adjuvants, e.g., Freund's adjuvant, may rupture cells and therefore is discouraged. The immunogen may be administered multiple times at periodic intervals such as, bi weekly, or weekly, or may be administered in such a way as to maintain viability in the animal (e.g., in a tissue recombinant). Alternatively, existing monoclonal antibodies and any other equivalent antibodies that are immunospecific for a desired pathogenic epitope can be sequenced and produced recombinantly by any means known in the art. In one embodiment, such an antibody is sequenced and the polynucleotide sequence is then cloned into a vector for expression or propagation. The sequence encoding the antibody of interest may be maintained in a vector in a host cell and the host cell can then be expanded and frozen for future use. The polynucleotide sequence of such antibodies may be used for genetic manipulation to generate a chimeric antibody, a humanized antibody, or a caninized antibody, or to improve the affinity, or other characteristics of the antibody. The term "humanized" antibody refer to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The polynucleotide sequence of the variable domains of such antibodies may be used for genetic manipulation to generate such derivatives and to improve the affinity, or other characteristics of such antibodies. The general principle in humanizing an antibody involves retaining the basic sequence of the antigen-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable Domains (2) designing the humanized antibody or canonized antibody, i.e., deciding which antibody framework region to use during the humanizing or canonizing process (3) the actual humanizing or canonizing methodologies/techniques and (4) the transfection and expression of the humanized antibody. See, for example, U.S. Pat. Nos. 4,816,567; 5,807,715; 5,866,692; and 6,331,415.

The epitope-binding site of such antibodies may comprise either complete Variable Domains fused onto Constant Domains or only the complementarity determining regions (CDRs) grafted onto appropriate framework regions in the Variable Domains. Antigen-binding sites may be wild-type or modified by one or more amino acid substitutions. This eliminates the constant region as an immunogen in human individuals, but the possibility of an immune response to the foreign variable region remains (LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224). Another approach focuses not only on providing human-derived constant regions, but modifying the variable regions as well so as to reshape them as closely as possible to human form. It is known that the variable regions of both heavy and light chains contain three complementarity determining regions (CDRs) which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the variable regions can be "reshaped" or "humanized" by grafting CDRs derived from non-human antibody on the FRs present in the human antibody to be modified. Application of this approach to various antibodies has been reported by Sato, K. et al. (1993) Cancer Res 53:851-856. Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, or six) which differ in sequence relative to the original antibody.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains (see, for example, Winter et al. (1991) "*Man-made Antibodies*," Nature 349:293-299; Lobuglio et al. (1989) "*Mouse/Human Chimeric Monoclonal Antibody In Man: Kinetics And Immune Response*," Proc. Natl. Acad. Sci. (U.S.A.) 86:4220-4224 (1989), Shaw et al. (1987) "*Characterization Of A Mouse/Human Chimeric Monoclonal Antibody (17-1A) To A Colon Cancer Tumor-Associated Antigen*," J. Immunol. 138:4534-4538, and Brown et al. (1987) "*Tumor-Specific Genetically Engineered Murine/Human Chimeric Monoclonal Antibody*," Cancer Res. 47:3577-3583). Other references describe rodent CDRs grafted into a human supporting framework region (FR) prior to fusion with an appropriate human antibody constant domain (see, for example, Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; and Jones et al. (1986) "*Replacing The Complementarity-Determining Regions In A Human Antibody With Those From A Mouse*," Nature 321:522-525). Another reference describes rodent CDRs supported by recombinantly veneered rodent framework regions. See, for example, European Patent Publication No. 519,596. These "humanized" molecules are designed to minimize unwanted immunological response toward rodent anti-human antibody molecules, which limits the duration and effectiveness of therapeutic applications of those moieties in human recipients. Other methods of humanizing antibodies that may also be utilized are disclosed by Daugherty et al. (1991) "*Polymerase Chain Reaction Facilitates The Cloning. CDR-Grafting. And Rapid Expression Of A Murine Monoclonal Antibody Directed Against The CD18 Component Of Leukocyte Integrins*," Nucl. Acids Res. 19:2471-2476 and in U.S. Pat. Nos. 6,180,377; 6,054,297; 5,997,867; and 5,866,692.

2. Bi-Specific Antibodies

Natural antibodies are capable of binding to only one epitope species (i.e., they are "mono-specific"), although they may be able to bind multiple copies of that species (i.e., they may exhibit bi-valency or multi-valency). The functionality of antibodies can be enhanced by generating multispecific antibody-based molecules that can simultaneously bind two separate and distinct antigens (or different epitopes of the same antigen) and/or by generating antibody-based molecule having higher valency (i.e., more than two binding sites) for the same epitope and/or antigen.

A wide variety of recombinant bi-specific and tri-specific antibody formats have been developed (see, e.g., U.S. Pat.

Nos. 8,277,806; 6,994,853; 6,551,592 and 6,171,586; United States Patent Publication No. 2010-0291112 and 2008-0057054; and PCT Publication Nos. WO 2013/070565, WO 2012/156430, WO 2012/009544, WO 2009/132876, WO 2009/018386, WO 2008/003116, WO 2008/003103, WO 2007/146968, WO 2006/072152, WO 2002/020039, WO 2000/018806; WO 1999/042597, WO 1998/006749 and WO 1998/003670), most of which use linker peptides either to fuse the antibody core (IgA, IgD, IgE, IgG or IgM) to a further epitope-binding site (e.g., scFv, VL VH, etc.) to, or within, the antibody core, or to fuse multiple epitope-binding site (e.g. two Fab fragments or scFv) to each other. Alternative formats use linker peptides to fuse an epitope-binding site (e.g., an scFv, VL, VH, etc.) to a dimerization domain such as the CH2-CH3 Domain or alternative polypeptides (WO 2005/070966, WO 2006/107786A WO 2006/107617A, WO 2007/046893). PCT Publications Nos. WO 2013/174873, WO 2011/133886 and WO 2010/136172 teach tri-specific antibodies in which the CL and CHI Domains are switched from their respective natural positions and the VL and VH Domains have been diversified (WO 2008/027236; WO 2010/108127) to allow them to bind to more than one antigen. PCT Publications Nos. WO 2013/163427 and WO 2013/119903 disclose modifying the CH2 Domain to contain a fusion protein adduct comprising a binding domain. PCT Publications Nos. WO 2010/028797, WO2010028796 and WO 2010/028795 disclose recombinant antibodies whose Fc Domains have been replaced with additional VL and VH Domains, so as to form tri-valent binding molecules. PCT Publications No. WO 2013/006544 discloses multi-valent Fab molecules that are synthesized as a single polypeptide chain and then subjected to proteolysis to yield heterodimeric structures. PCT Publications Nos. WO 2014/022540, WO 2013/003652, WO 2012/162583, WO 2012/156430, WO 2011/086091, WO 2007/075270, WO 1998/002463, WO 1992/022583 and WO 1991/003493 disclose adding additional Binding Domains or functional groups to an antibody or an antibody portion (e.g., adding additional VL and VH Domains to the antibody's light and heavy chains, or adding a heterologous fusion protein or chaining multiple Fab Domains to one another). U.S. Pat. No. 7,695,936 and Patent Publication 2007/0196363 concern bi-specific antibodies that are formed from the heavy chains of two antibodies, one of which possess a protuberance engineered into its heavy chain and the second of which possess a complementary cavity engineered into its heavy chain. The presence of such complementary "knobs" and "holes" is taught to preferentially form bi-specific hetero-antibodies (having one heavy chain of each such antibody) relative to mono-specific homo-antibodies that contain two heavy chains of the same antibody.

3. Preferred Fc Domains

The CH2 and CH3 Domains of the two heavy chains interact to form the Fc Domain, which is a domain that is recognized by cellular Fc Receptors (FcγRs). As used herein, the term "Fc Domain" is used to define a C-terminal region of an IgG heavy chain. The amino acid sequence of the CH2-CH3 domain of an exemplary human IgG1 is (SEQ ID NO:1):

```
231    240        250        260        270
APELLGGPSV FLFPPKPKDT LMISRTPEVT CVVVDVSHED

       280        290        300        310
PEVKFNWYVD GVEVHNAKTK PREEQYNSTY RVVSVLTVLH
```

-continued

```
       320        330        340        350
QDWLNGKEYK CKVSNKALPA PIEKTISKAK GQPREPQVYT

       360        370        380        390
LPPSREEMTK NQVSLTCLVK GFYPSDIAVE WESNGQPENN

       400        410        420        430
YKTTPPVLDS DGSFFLYSKL TVDKSRWQQG NVFSCSVMHE

       440    447
ALHNHYTQKS LSLSPGX
```

as numbered by the EU index as set forth in Kabat, wherein X is a lysine (K) or is absent.

The amino acid sequence of the CH2-CH3 Domain of an exemplary human IgG2 is (SEQ ID NO:2):

```
231    240        250        260        270
APPVA-GPSV FLFPPKPKDT LMISRTPEVT CVVVDVSHED

       280        290        300        310
PEVQFNWYVD GVEVHNAKTK PREEQFNSTF RVVSVLTVVH

       320        330        340        350
QDWLNGKEYK CKVSNKGLPA PIEKTISKTK GQPREPQVYT

       360        370        380        390
LPPSREEMTK NQVSLTCLVK GFYPSDISVE WESNGQPENN

       400        410        420        430
YKTTPPMLDS DGSFFLYSKL TVDKSRWQQG NVFSCSVMHE

       440    447
ALHNHYTQKS LSLSPGX
```

as numbered by the EU index as set forth in Kabat, wherein, X is a lysine (K) or is absent.

The amino acid sequence of the CH2-CH3 Domain of an exemplary human IgG3 is (SEQ ID NO:3):

```
231    240        250        260        270
APELLGGPSV FLFPPKPKDT LMISRTPEVT CVVVDVSHED

       280        290        300        310
PEVQFKWYVD GVEVHNAKTK PREEQYNSTF RVVSVLTVLH

       320        330        340        350
QDWLNGKEYK CKVSNKALPA PIEKTISKTK GQPREPQVYT

       360        370        380        390
LPPSREEMTK NQVSLTCLVK GFYPSDIAVE WESSGQPENN

       400        410        420        430
YNTTPPMLDS DGSFFLYSKL TVDKSRWQQG NIFSCSVMHE

       440    447
ALHNRFTQKS LSLSPGX
```

as numbered by the EU index as set forth in Kabat, wherein, X is a lysine (K) or is absent.

The amino acid sequence of the CH2-CH3 Domain of an exemplary human IgG4 is (SEQ ID NO:4):

```
231    240        250        260        270
APEFLGGPSV FLFPPKPKDT LMISRTPEVT CVVVDVSQED

       280        290        300        310
PEVQFNWYVD GVEVHNAKTK PREEQFNSTY RVVSVLTVLH

       320        330        340        350
QDWLNGKEYK CKVSNKGLPS SIEKTISKAK GQPREPQVYT

       360        370        380        390
LPPSQEEMTK NQVSLTCLVK GFYPSDIAVE WESNGQPENN
```

-continued

```
      400          410          420          430
YKTTPPVLDS DGSFFLYSRL TVDKSRWQEG NVFSCSVMHE

      440     447
ALHNHYTQKS LSLSLGX
```

as numbered by the EU index as set forth in Kabat, wherein, X is a lysine (K) or is absent.

Throughout the present specification, the numbering of the residues in the constant region of an IgG heavy chain is that of the EU index as in Kabat et al., *Sequences of Proteins of Immunological Interest,* 5th Ed. Public Health Service, NH1, MD (1991), expressly incorporated herein by references. The "EU index as in Kabat" refers to the numbering of the human IgG1 EU antibody. Amino acids from the variable regions of the mature heavy and light chains of immunoglobulins are designated by the position of an amino acid in the chain. Kabat described numerous amino acid sequences for antibodies, identified an amino acid consensus sequence for each subgroup, and assigned a residue number to each amino acid. Kabat's numbering scheme is extendible to antibodies not included in his compendium by aligning the antibody in question with one of the consensus sequences in Kabat by reference to conserved amino acids. This method for assigning residue numbers has become standard in the field and readily identifies amino acids at equivalent positions in different antibodies, including chimeric or humanized variants. For example, an amino acid at position 50 of a human antibody light chain occupies the equivalent position to an amino acid at position 50 of a mouse antibody light chain.

Although boundaries may vary slightly, the CH2 domain of a human IgG Fc Domain usually extends from amino acids 231 to amino acid 341 of a human IgG according to the EU numbering system of Kabat. The CH3 domain of a human IgG usually extends from amino acids 342 to 447 according to the EU numbering system of Kabat. The "hinge region" or "hinge domain" is generally defined as stretching from Glu216 to Pro230 of human IgG1.

Polymorphisms have been observed at a number of different positions within antibody constant regions (e.g., Fc positions, including but not limited to positions 270, 272, 312, 315, 356, and 358 as numbered by the EU index as set forth in Kabat), and thus slight differences between the presented sequence and sequences in the prior art can exist. Polymorphic forms of human immunoglobulins have been well-characterized. At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m(b1, c3, b3, b0, b3, b4, s, t, g1, c5, u, v, g5) (Lefranc, et al., The human IgG subclasses: molecular analysis of structure, function and regulation. Pergamon, Oxford, pp. 43-78 (1990); Lefranc, G. et al., 1979, Hum. Genet.: 50, 199-211). It is specifically contemplated that the antibodies useful in the methods of the present invention may incorporate any allotype, isoallotype, or haplotype of any immunoglobulin gene, and are not limited to the allotype, isoallotype or haplotype of the sequences provided herein. Furthermore, in some expression systems the C-terminal amino acid residue (bolded above) of the CH3 Domain may be post-translationally removed. Accordingly, the C-terminal residue of the CH3 Domain is an optional amino acid residue in the B7-H3-binding molecules and PD-1-binding molecules provided herein. Specifically encompassed by the instant invention are such binding molecules lacking the C-terminal residue of the CH3 Domain. Also specifically encompassed by the instant invention are such binding molecules comprising the C-terminal lysine residue of the CH3 Domain.

When present, the CHI Domain and/or hinge region may be of any isotype (e.g., IgG1, IgG2, IgG3, or IgG4), but is preferably of the same isotype as the desired Fc Domain.

The amino acid sequence of an exemplary human IgG1 CHI Domain is (SEQ ID NO:8):

```
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKRV
```

The amino acid sequence of an exemplary human IgG2 CHI Domain is (SEQ ID NO:60):

```
ASTKGPSVFP LAPCSRSTSE STAALGCLVK DYFPEPVTVS

WNSGALTSGV HTFPAVLQSS GLYSLSSVVT VPSSNFGTQT

YTCNVDHKPS NTKVDKTV
```

The amino acid sequence of an exemplary human IgG4 CH1 Domain is (SEQ ID NO:61):

```
ASTKGPSVFP LAPCSRSTSE STAALGCLVK DYFPEPVTVS

WNSGALTSGV HTFPAVLQSS GLYSLSSVVT VPSSSLGTKT

YTCNVDHKPS NTKVDKRV
```

The amino acid sequence of an IgG4 CH1 Domain and Stabilized Hinge (SEQ ID NO:16) is shown below,

```
ASTKGPSVFP LAPCSRSTSE STAALGCLVK DYFPEPVTVS

WNSGALTSGV HTFPAVLQSS GLYSLSSVVT VPSSSLGTKT

YTCNVDHKPS NTKVDKRVES KYGPPCPPCP
```

The amino acid sequence of an exemplary human IgG1 hinge region is (SEQ ID NO:10):

```
EPKSCDKTHTCPPCP
```

The amino acid sequence of an exemplary human IgG2 hinge region is (SEQ ID NO:62):

```
ERKCCVECPPERKCCVECPPCP
```

The amino acid sequence of an exemplary human IgG4 hinge region is (SEQ ID NO:11)

```
ESKYGPPCPSCP
```

Activating and inhibitory signals are transduced through the Fc gamma Receptors (FcγRs) following their ligation to an Fc Domain. These diametrically opposing functions result from structural differences among the different receptor isoforms. Two distinct domains within the cytoplasmic signaling domains of the receptor called immunoreceptor tyrosine-based activation motifs (ITAMs) or immunoreceptor tyrosine-based inhibitory motifs (ITIMS) account for the different responses. The recruitment of different cytoplasmic enzymes to these structures dictates the outcome of the FcγR-mediated cellular responses. ITAM-containing FcγR complexes include FcγRI, FcγRIIA, FcγRIIIA, whereas ITIM-containing complexes only include FcγRIIB. Human neutrophils express the FcγRIIA gene. FcγRIIA clustering via immune complexes or specific antibody cross-linking serves to aggregate ITAMs along with receptor-associated kinases which facilitate ITAM phosphorylation. ITAM phosphorylation serves as a docking site for Syk kinase, activation of which results in activation of downstream substrates (e.g., $PI_3K$). Cellular activation leads to release of proinflammatory mediators. The FcγRIIB gene is expressed on B lymphocytes; its extracellular domain is 96% identical to FcγRIIA and binds IgG complexes in an indistinguishable manner. The presence of an TIM in the cytoplasmic domain of FcγRIIB defines this inhibitory subclass of FcγR. Recently the molecular basis of this inhibition was established. When co-ligated along with an activating FcγR, the ITIM in FcγRIIB becomes phosphorylated and attracts the SH2 domain of the inositol polyphosphate 5'-phosphatase (SHIP), which hydrolyzes phosphoinositol messengers released as a consequence of ITAM-containing FcγR-mediated tyrosine kinase activation, consequently preventing the influx of intracellular $Ca^{++}$. Thus cross-linking of FcγRIIB dampens the activating response to FcγR ligation and inhibits cellular responsiveness. B cell activation, B cell proliferation and antibody secretion is thus aborted. In addition, interaction with the neonatal Fc Receptor (FcRn) mediates the recycling of IgG molecules from the endosome to the cell surface and release into the blood.

Modification of the Fc Domain normally leads to an altered phenotype, for example altered serum half-life, altered stability, altered susceptibility to cellular enzymes or altered effector function. It may be desirable to modify the Fc Domain of the B7-H3-binding molecules and/or PD-1-binding molecules (e.g., anti-B7-H3 and anti-PD-1 antibodies) for use in the methods of the present invention with respect to effector function, so as to enhance the effectiveness of the antibody in treating cancer, for example. Reduction or elimination of effector function is desirable in certain cases, for example in the case of antibodies whose mechanism of action involves blocking or antagonism, but not killing of the cells bearing a target antigen. Increased effector function is generally desirable when directed to undesirable cells, such as tumor and foreign cells, where the FcγRs are expressed at low levels, for example, tumor-specific B cells with low levels of FcγRIIB (e.g., non-Hodgkin's lymphoma, CLL, and Burkitt's lymphoma).

The Fc Domain of the B7-H3-binding molecules and/or PD-1-binding molecules (e.g., anti-B7-H3 and anti-PD-1 antibodies) for use in the methods of the present invention may be either a complete Fc Domain (e.g., a complete IgG Fc Domain) or only a fragment of a complete Fc Domain. Thus, the Fc Domain of the molecules useful in the methods of the present invention that contain such a domain may include some or all of the CH2 Domain and/or some or all of the CH3 Domain of a complete Fc Domain, or may comprise a variant CH2 and/or a variant CH3 sequence (that may include, for example, one or more insertions and/or one or more deletions with respect to the CH2 or CH3 domains of a complete Fc Domain). Such Fc Domains may comprise non-Fc polypeptide portions, or may comprise portions of non-naturally complete Fc Domains, or may comprise non-naturally occurring orientations of CH2 and/or CH3 domains (such as, for example, two CH2 domains or two CH3 Domains, or in the N-terminal to C-terminal direction, a CH3 Domain linked to a CH2 Domain, etc.). Although the Fc Domain of the B7-H3-binding molecules and/or PD-1-binding molecules may possess the ability to bind to one or more Fc receptors (e.g., FcγR(s)), more preferably such Fc Domain will cause altered binding to FcγRIA (CD64), FcγRIIA (CD32A), FcγRIIB (CD32B), FcγRIIIA (CD16a) or FcγRIIIB (CD16b) (relative to the binding exhibited by a wild-type Fc Domain) or will substantially eliminate the ability of such Fc Domain to bind to one or more FcγR (e.g., inhibitory receptor(s)).

In certain embodiments the molecules for use in the methods of the present invention may comprise a variant Fc Domain having altered affinities for an activating and/or inhibitory Fcγ receptor. In one embodiment, the molecules comprise a variant Fc Domain that has increased affinity for FcγRIIB and decreased affinity for FcγRIIIA and/or FcγRIIA, relative to a comparable molecule with a wild-type Fc Domain. In another embodiment, the molecules for use in the methods of the present invention comprise a variant Fc Domain that has decreased affinity for FcγRIIB and increased affinity for FcγRIIIA and/or FcγRIIA, relative to a comparable molecule with a wild-type Fc Domain. In yet another embodiment, molecules for use in the methods of the present invention comprise a variant Fc Domain that has decreased affinity for FcγRIIB and decreased affinity for FcγRIIIA and/or FcγRIIA, relative to a comparable molecule with a wild-type Fc Domain. In still another embodiment, the molecules for use in the methods of the present invention comprise a variant Fc Domain that has unchanged affinity for FcγRIIB and decreased (or increased) affinity for FcγRIIIA and/or FcγRIIA, relative to a comparable molecule with a wild-type Fc Domain.

In certain embodiments, the molecules for use in the methods of the present invention comprise a variant Fc Domain having an altered affinity for FcγRIIIA and/or FcγRIIA such that the immunoglobulin has an enhanced effector function. Non-limiting examples of effector cell functions include antibody dependent cell mediated cytotoxicity, antibody dependent phagocytosis, phagocytosis, opsonization, opsonophagocytosis, cell binding, rosetting, C1q binding, and complement dependent cell mediated cytotoxicity.

Variant Fc Domains are well known in the art, and any known variant Fc Domain may be used in the present invention to confer or modify the effector function exhibited by a molecule comprising an Fc Domain (or portion thereof) as functionally assayed, e.g., in an NK dependent or macrophage dependent assay. For example, Fc Domain variants identified as altering effector function are disclosed in PCT Publications No. WO 04/063351; WO 06/088494; WO 07/024249; WO 06/113665; WO 07/021841; WO 07/106707; and WO 2008/140603, and any suitable variant disclosed therein may be used in the present molecules.

Table 4 lists exemplar, single, double, triple, quadruple and quintuple Fc Domain mutations.

TABLE 4

| Variations of Preferred Activating Fc Domains | | | |
|---|---|---|---|
| Single-Site Variations | | | |
| F243L | R292G | D270E | R292P |
| Y300L | P396L | | |
| Double-Site Variations | | | |
| F243L and R292P | F243L and Y300L | F243L and P396L | R292P and Y300L |
| D270E and P396L | R292P and V305I | P396L and Q419H | P247L and N421K |
| R292P and P396L | Y300L and P396L | R255L and P396L | R292P and P305I |
| K392T and P396L | | | |

TABLE 4-continued

| Variations of Preferred Activating Fc Domains | |
|---|---|
| Triple-Site Variations | |
| F243L, P247L and N421K | P247L, D270E and N421K |
| F243L, R292P and Y300L | R255L, D270E and P396L |
| F243L, R292P and V305I | D270E, G316D and R416G |
| F243L, R292P and P396L | D270E, K392T and P396L |
| F243L, Y300L and P396L | D270E, P396L and Q419H |
| V284M, R292L and K370N | R292P, Y300L and P396L |
| Quadruple-Site Variations | |
| L234F, F243L, R292P and Y300L | F243L, P247L, D270E and N421K |
| L234F, F243L, R292P and Y300L | F243L, R255L, D270E and P396L |
| L235I, F243L, R292P and Y300L | F243L, D270E, G316D and R416G |
| L235Q, F243L, R292P and Y300L | F243L, D270E, K392T and P396L |
| P247L, D270E, Y300L and N421K | F243L, R292P, Y300L, and P396L |
| R255L, D270E, R292G and P396L | F243L, R292P, V305I and P396L |
| R255L, D270E, Y300L and P396L | F243L, D270E, P396L and Q419H |
| D270E, G316D, P396L and R416G | |
| Quintuple-Site Variations | |
| L235V, F243L, R292P, Y300L and P396L | F243L, R292P, V305I, Y300L and P396L |
| L235P, F243L, R292P, Y300L and P396L | |

Particularly preferred variants include one or more modifications selected from groups A-AI:

| | |
|---|---|
| A | 228E, 228K, 228Y or 228G; |
| B | 230A, 230E, 230Y or 230G; |
| C | 231E, 231K, 231Y, 231P or 231G; |
| D | 232E, 232K, 232Y, 232G; |
| E | 233D; |
| F | 234I or 234F; |
| G | 235D, 235Q, 235P, 235I or 235V; |
| H | 239D, 239E, 239N or 239Q; |
| I | 240A, 240I, 240M or 240T; |
| J | 243R, 243, 243Y, 243L, 243Q, 243W, 243H or 243I; |
| K | 244H; |
| L | 245A; |
| M | 247G, 247V or 247L; |
| N | 262A, 262E, 262I, 262T, 262E or 262F; |
| O | 263A, 263I, 263M or 263T; |
| P | 264F, 264E, 264R, 264I, 264A, 264T or 264W; |
| Q | 265F, 265Y, 265H, 265I, 265L, 265T, 265V, 265N or 265Q; |
| R | 266A, 266I, 266M or 266T; |
| S | 271D, 271E, 271N, 271Q, 271K, 271R, 271S, 271T, 271H, 271A, 271V, 271L, 271I, 271F, 271M, 271Y, 271W or 271G; |
| T | 273I; |
| U | 275L or 275W; |
| V | 281D, 281K, 281Y or 281P; |
| W | 284E, 284N, 284T, 284L, 284Y or284M; |
| X | 291D, 291E, 291Q, 291T, 291H, 291I or 291G; |
| Y | 299A, 299D, 299E, 299F, 299G, 299H, 299I, 299K, 299L, 299M, 299N, 299P, 299Q, 299R, 299S, 299V, 299W or 299Y; |
| Z | 302I; |
| AA | 304D, 304N, 304T, 304H or 304L |
| AB | 305I; |
| AC | 313F; |
| AD | 323I; |
| AE | 325A, 325D, 325E, 325G, 325H, 325I, 325L, 325K, 325R, 325S, 325F, 325M, 325T, 325V, 325Y, 325W or 325P; |
| AF | 328D, 328Q, 328K, 328R, 328S, 328T, 328V, 328I, 328Y, 328W, 328P, 328G, 328A, 328E, 328F, 328H, 328M or 328N; |
| AG | 330L, 330Y, 330I or 330V; |
| AH | 332A, 332D, 332E, 332H, 332N, 332Q, 332T, 332K, 332R, 332S, 332V, 332L, 332F, 332M, 332W, 332P, 332G or 332Y; and |
| AI | 336E, 336K or 336Y |

Still more particularly preferred variants include one or more modifications selected from Groups 1-105:

| Group | Variant |
|---|---|
| 1 | A330L/I332E |
| 2 | D265F/N297E/I332E |
| 3 | D265Y/N297D/I332E |
| 4 | D265Y/N297D/T299L/I332E |
| 5 | F241E/F243Q/V262T/V264F |
| 6 | F241E/F243Q/V262T/V264E/I332E |
| 7 | F241E/F243R/V262E/V264R |
| 8 | F241E/F243R/V262E/V264R/I332E |
| 9 | F241E/F243Y/V262T/V264R |
| 10 | F241E/F243Y/V262T/V264R/I332E |
| 11 | F241L/F243L/V262I/V264I |
| 12 | F241L/V262I |
| 13 | F241R/F243Q/V262T/V264R |
| 14 | F241R/F243Q/V262T/V264R/I332E |
| 15 | F241W/F243W/V262A/V264A |
| 16 | F241Y/F243Y/V262T/V264T |
| 17 | F241Y/F243Y/V262T/V264T/N297D/I332E |
| 18 | F243L/V262I/V264W |
| 19 | P243L/V264I |
| 20 | L328D/I332E |
| 21 | L328E/I332E |
| 22 | L328H/I332E |
| 23 | L328I/I332E |
| 24 | L328M/I332E |
| 25 | L328N/I332E |
| 26 | L328Q/I332E |
| 27 | L328T/I332E |
| 28 | L328V/I332E |
| 29 | N297D/A330Y/I332E |
| 30 | N297D/I332E |
| 31 | N297D/I332E/S239D/A330L |
| 32 | N297D/S298A/A330Y/I332E |
| 33 | N297D/T299L/I332E |
| 34 | N297D/T299F/I332E/N297D/T299H/I332E |
| 35 | N297D/T299I/I332E |
| 36 | N297D/T299L/I332E |
| 37 | N297D/T299V/I332E |
| 38 | N297E/I332E |
| 39 | N297S/I332E |
| 40 | P230A/E233D/I332E |
| 41 | P244H/P245A/P247V |
| 42 | S239D/A330L/I332E |
| 43 | S239D/A330Y/I332E |
| 44 | S239D/A330Y/I332E/K326E |
| 45 | S239D/A330Y/I332E/K326T |
| 46 | S239D/A330Y/I332E/L234I |
| 47 | S239D/A330Y/I332E/L235D |
| 48 | S239D/A330Y/I332E/V240I |
| 49 | S239D/A330Y/I332E/V264T |
| 50 | S239D/A330Y/I332E/V266I |
| 51 | S239D/D265F/N297D/I332E |
| 52 | S239D/D265H/N297D/I332E |
| 53 | S239D/D265I/N297D/I332E |
| 54 | S239D/D265L/N297D/I332E |
| 55 | S239D/D265T/N297D/I332E |
| 56 | S239D/D265V/N297D/I332E |
| 57 | S239D/D265Y/N297D/I332E |
| 58 | S239D/I332D |
| 59 | S239D/I332E |
| 60 | S239D/I332E/A330I |
| 61 | S239D/I332N |
| 62 | S239D/I332Q |
| 63 | S239D/N297D/I332E |
| 64 | S239D/N297D/I332E/A330Y |
| 65 | S239D/N297D/I332E/A330Y/F241S/F243H/V262T/V264T |
| 66 | S239D/N297D/I332E/K326E |
| 67 | S239D/N297D/I332E/L235D |
| 68 | S239D/S298A/I332E |
| 69 | S239D/V264I/A330L/I332E |
| 70 | S239D/V264I/I332E |
| 71 | S239D/V264I/S298A/I332E |
| 72 | S239E/D265N |
| 73 | S239E/D265Q |
| 74 | S239E/I332D |
| 75 | S239E/I332E |
| 76 | S239E/I332N |
| 77 | S239E/I332Q |
| 78 | S239E/N297D/I332E |
| 79 | S239E/V264I/A330Y/I332E |
| 80 | S239E/V264I/I332E |
| 81 | S239E/V264I/S298A/A330Y/I332E |
| 82 | S239N/A330L/I332E |
| 83 | S239N/A330Y/I332E |
| 84 | S239N/I332D |
| 85 | S239N/I332E |
| 86 | S239N/I332N |
| 87 | S239N/I332Q |
| 88 | S239N1S298A/I332E |
| 89 | S239Q/I332D |
| 90 | S239Q/I332E |
| 91 | S239Q/I332N |
| 92 | S239Q/I332Q |
| 93 | S239Q/V264I/I332E |
| 94 | S298A/I332E |
| 95 | V264E/N297D/I332E |
| 96 | V264I/A330L/I332E |
| 97 | V264I/A330Y/I332E |
| 98 | V264I/I332E |
| 99 | V264I/S298A/I332E |
| 100 | Y296D/N297D/I332E |
| 101 | Y296E/N297D/I332E |
| 102 | Y296H/N297D/I332E |
| 103 | Y296N/N297D/I332E |
| 104 | Y296Q/N297I/I332E |
| 105 | Y296T/N297D/I332E |

In particularly preferred embodiments, the invention encompasses B7-H3-binding molecules that comprise a variant Fc Domain wherein the variant confers or has an increased ADCC activity and/or an increased binding to FcγRIIIA (CD16A), and may also have a reduced binding to FcγRIIB (CD32B). Exemplary variants of human IgG1 Fc Domains with increased binding to CD16A and which may additionally have reduced binding to CD32B contain L235V, F243L, R292P, Y300L, V305I or P296L substitutions. Preferred B7-H3-binding molecules include variant IgG1 Fc Domains that include any 1, 2, 3, 4, 5, or 6 of the substitutions: L235V, F243L, R292P, Y300L, V305I and P396L. These amino acid substitutions may be present in a human IgG1 Fc Domain in any combination.

In one embodiment, a B7-H3-binding molecule will comprise a variant Fc Domain having at least one modification in the Fc Domain. In certain embodiments, the variant Fc Domain comprises at least one substitution selected from the group consisting of L235V, F243L, R292P, Y300L, V305I, and P396L.

In a specific embodiment, the variant Fc Domain comprises:

(A) at least one substitution selected from the group consisting of F243L, R292P, Y300L, V305I, and P396L;

(B) at least two substitutions selected from the group consisting of:

(1) F243L and P396L;

(2) F243L and R292P; and (3) R292P and V305I;

(C) at least three substitutions selected from the group consisting of:

(1) F243L, R292P and Y300L;

(2) F243L, R292P and V305I;

(3) F243L, R292P and P396L; and (4) R292P, V305I and P396L;

(D) at least four substitutions selected from the group consisting of:

(1) F243L, R292P, Y300L and P396L; and (2) F243L, R292P, V305I and P396L; or (E) at least the five substitutions selected from the group consisting of:

(1) F243L, R292P, Y300L, V305I and P396L; and (2) L235V, F243L, R292P, Y300L and P396L.

In another specific embodiment, the variant Fc Domain comprises substitutions of:

(A) F243L, R292P, and Y300L;

(B) L235V, F243L, R292P, Y300L, and P396L; or (C) F243L, R292P, Y300L, V305I, and P396L.

In certain embodiments the PD-1-binding molecule comprises a variant Fc Domain wherein the variant confers or has decreased (or substantially no) binding to FcγRIIIA (CD16a), relative to the binding exhibited by the wild-type Fc Domain (SEQ ID NO:1)).

Exemplary variants of human IgG1 Fc Domains with reduced binding to FcγRs contain L234A, L235A, D265A, N297A or N297Q, substitutions. Preferred PD-1-binding molecules include variant IgG1 Fc Domains that include any 1, 2, 3, 4, or all 5, of the substitutions: L234A, L235A, D265A, N297A, and N297Q. These amino acid substitutions may be present in a human IgG1 Fc Domain in any combination.

In one embodiment, a PD-1-binding molecule will comprise a variant Fc Domain having at least one modification in the Fc Domain. In certain embodiments, the variant Fc Domain comprises at least one substitution selected from the group consisting of L234A, L235A, D265A, and N297Q. Since the L234A, L235A, D265A, N297A, and N297Q substitutions abolish effector function, in circumstances in which effector function is desired, these substitutions would preferably not be employed.

In a specific embodiment, the variant Fc Domain comprises substitutions of:

(A) L234A, L235A;

(B) D265A;

(D) N297A; or (C) N297Q.

A preferred IgG1 sequence for the CH2 and CH3 Domains of the PD-1 binding molecules for use in the methods of the invention will have the L234A/L235A substitutions

```
                                    (SEQ ID NO: 5)
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGX
```

wherein, X is a lysine (K) or is absent.

In particularly preferred embodiments, the CH2-CH3 Domain of an Fc Domain-containing PD-1-binding molecule for use in the methods of the present invention may be one that inherently exhibits decreased (or substantially no) binding to FcγRIIIA (CD16a) and/or reduced effector function (relative to the binding exhibited by the wild-type IgG1 Fc Domain (SEQ ID NO:1)). For example, the CH2-CH3 Domain of an Fc Domain-containing PD-1-binding molecule for use in the methods of the present invention may be an IgG2 Fc Domain or an IgG4 Fc Domain.

In a preferred embodiment, a PD-1-binding molecule for use in the methods of the present invention comprises an IgG4 Fc Domain. Where an IgG4 Fc Domain in utilized the instant invention also encompasses the introduction of a stabilizing hinge mutation such as S228P (e.g., ESKYGPPCPPCP (SEQ ID NO:12)), as numbered by the EU index as set forth in Kabat (Lu et al., (2008) "*The Effect Of A Point Mutation On The Stability Of Igg4 As Monitored By Analytical Ultracentrifugation*," J. Pharm. Sci. 97:960-969) to reduce the incidence of strand exchange. Other stabilizing mutations known in the art may be introduced into an IgG4 Fc Domain (Peters, P et al., (2012) "*Engineering an Improved IgG4 Molecule with Reduced Disulfide Bond Heterogeneity and Increased Fab Domain Thermal Stability*," J. Biol. Chem., 287:24525-24533; PCT Patent Publication No: WO 2008/145142). Additionally, as noted above, when present, the CHI Domain and/or hinge is preferably of the same isotype as the desired Fc Domain. Accordingly, in such embodiments a PD-1-binding molecule (e.g. antibody) will comprise an IgG4 CHI (see, e.g., SEQ ID NO:9), a stabilized IgG4 hinge (see, e.g., SEQ ID NO:12), and IgG4 CH2-CH3 Domains (see, e.g., SEQ ID NO:4), The serum half-life of proteins comprising Fc Domains may be increased by increasing the binding affinity of the Fc Domain for FcRn. The term "half-life" as used herein means a pharmacokinetic property of a molecule that is a measure of the mean survival time of the molecules following their administration. Half-life can be expressed as the time required to eliminate fifty percent (50%) of a known quantity of the molecule from the subject's body (e.g., human patient or other mammal) or from or a specific compartment thereof, for example, as measured in serum, i.e., circulating half-life, or in other tissues. In general, an increase in half-life for an administered molecule results in an increase in that molecule's mean residence time (MRT) in circulation.

In some embodiments, the B7-H3-binding molecules and/or PD-1-binding molecules for use in the methods of the present invention comprise a variant Fc Domain, wherein the variant Fc Domain comprises at least one amino acid modification relative to a wild-type Fc Domain, such that the molecule has an increased half-life (relative to that of a wild-type Fc Domain).

In some embodiments, the B7-H3-binding molecules and/or PD-1-binding molecules for use in the methods of the present invention comprise a variant Fc Domain, wherein the variant Fc Domain comprises a half-live extending amino acid substitution at one or more positions selected from the group consisting of 238, 250, 252, 254, 256, 257, 256, 265, 272, 286, 288, 303, 305, 307, 308, 309, 311, 312, 317, 340, 356, 360, 362, 376, 378, 380, 382, 413, 424, 428, 433, 434, 435, and 436. Numerous specific mutations capable of increasing the half-life of an Fc Domain-containing molecule are known in the art and include, for example M252Y, S254T, T256E, and combinations thereof. For example, see the mutations described in U.S. Pat. Nos. 6,277,375, 7,083,784; 7,217,797, 8,088,376; U.S. Publication Nos. 2002/0147311; 2007/0148164; and International Publication Nos. WO 98/23289; WO 2009/058492; and WO 2010/033279, which are herein incorporated by reference in their entireties. Fc Domain-containing molecules with enhanced half-life also include those with substitutions at two or more of Fc Domain residues 250, 252, 254, 256, 257, 288, 307, 308, 309, 311, 378, 428, 433, 434, 435, and 436. In particular, two or more substitutions selected from: T250Q, M252Y, S254T, T256E, K288D, T307Q, V308P, A378V, M428L, N434A, H435K, Y4361.

In a specific embodiment, the variant Fc Domain comprises substitutions of:

(A) M252Y, S254T and T256E;
(B) M252Y and S254T;
(C) M252Y and T256E;
(D) T250Q and M428L;
(E) T307Q and N434A;
(F) A378V and N434A;
(G) N434A and Y4361;
(H) V308P and N434A; or
(I) K288D and H435K.

The instant invention further encompasses variant Fc Domains comprising:

(A) one or more mutations which alter effector function and/or FcγR and
(B) one or more mutations which extend serum half-life.

The two CH2 and/or two CH3 Domains of the CH2-CH3 Domains of two interacting Fc Domain-containing polypeptide chains of an B7-H3-binding molecules and/or PD-1-binding molecule for use in the methods of the present invention need not be identical in sequence, and advantageously are modified to foster complexing between the two polypeptide chains (see, for example: WO 98/50431; WO2007/110205; WO2011/143545; WO 2012/058768; WO 2013/06867). For example, an amino acid substitution (preferably a substitution with an amino acid comprising a bulky side group forming a "knob", e.g., tryptophan) can be introduced into the CH2 or CH3 Domain such that steric interference will prevent interaction with a similarly mutated domain and will obligate the mutated domain to pair with a domain into which a complementary, or accommodating mutation has been engineered, i.e., "the hole" (e.g., a substitution with glycine). Such sets of mutations can be engineered into any of the polypeptides of the Fc Domain-containing B7-H3-binding molecules and/or PD-1-binding molecules of the present invention. Methods of protein engineering to favor heterodimerization over homodimerization are well-known in the art, in particular with respect to the engineering of immunoglobulin-like molecules, and are encompassed herein (see e.g., Ridgway et al. (1996) "*'Knobs-Into-Holes' Engineering Of Antibody CH3 Domains For Heavy Chain Heterodimerization*." Protein Engr. 9:617-621, Atwell et al. (1997) "*Stable Heterodimers From Remodeling The Domain Interface Of A Homodimer Using A Phage Display Library*." J. Mol. Biol. 270: 26-35, and Xie et al. (2005) "*A New Format OfBi-specific Antibody: Highly Efficient Heterodimerization. Expression And Tumor Cell Lysis*." J. Immunol. Methods 296:95-101; each of which is hereby incorporated herein by reference in its entirety). Preferably the "knob" is engineered into the CH2-CH3 Domains of one polypeptide chain and the "hole" is engineered into the CH2-CH3 Domains of the other CH2-CH3-containing polypeptide chain. Thus, the "knob" will help in preventing the first polypeptide chain from homodimerizing via its CH2 and/or CH3 Domains. The CH2-CH3 "hole-bearing" polypeptide chain will heterodimerize with the CH2-CH3 "knob-bearing" polypeptide chain, and will also homodimerize with itself. A preferred knob is created by modifying a native IgG Fc Domain to contain the modification T366W. A preferred hole is created by modifying a native IgG Fc Domain to contain the modification T366S, L368A and Y407V. To aid in purifying the "hole-bearing" polypeptide chain homodimer from the preferred heterodimer molecule, the protein A binding site of the CH2 and CH3 Domains of the "hole-bearing" Fc Domain is preferably mutated by amino acid substitution at position 435 (H435R). Thus, the "hole-bearing" Fc Domain homodimer will not bind to protein A, whereas an Fc Domain-containing B7-H3-binding molecule and/or PD-1-binding molecule for use in the methods of the present invention will retain its ability to bind protein A via the protein A binding site on the first polypeptide chain.

A preferred "knob-bearing" sequence for an Fc Domain-containing B7-H3-binding molecule and/or PD-1 binding molecule has the sequence (SEQ ID NO:6):

APELLGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGX wherein, X is a lysine (K) or is absent.

A preferred "hole-bearing" sequence for an Fc Domain-containing B7-H3-binding molecule and/or PD-1 binding molecule has the sequence (SEQ ID NO:7):

APELLGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSTWQQG NVFSCSVMHE

ALHNRYTQKS LSLSPGX wherein, X is a lysine (K) or is absent.

The invention also encompasses such CH2-CH3 Domains, which comprise additional substitutions which modify effector function and/or FγR binding activity of the Fc Domain as provided above. The invention also encompasses such CH2-CH3 Domains, which further comprise one or more half-live extending amino acid substitutions. In particular, the invention encompasses such hole-bearing and such knob-bearing CH2-CH3 Domains which further comprise the M252Y/S254T/T256E substitutions.

B. B7-H3-Binding Molecules

Molecules that specifically bind B7-H3 encompassed by the invention include anti-B7-H3 antibodies capable of binding to a continuous or discontinuous (e.g., conformational) portion (epitope) of human B7-H3, and molecules comprising the epitope-binding site of such antibodies. The B7-H3-binding molecules used in the methods and compositions of the present invention will preferably also exhibit the ability to bind to the B7-H3 molecules of one or more non-human species, especially, murine, rodent, canine, and primate species. Antibodies that are specific for B7-H3 are known (see, e.g., U.S. Pat. Nos. 7,527,969; 7,666,424; 7,718,774; 7,737,258; 7,740,845; 8,148,154; 8,216,570; 8,414,892; 8,501,471; 8,779,098; 8,802,091; 9,062,110; US Patent Publication Nos. 2013/0078234; 2010/0143245; and PCT Patent Publications WO 2004/001381; WO 2008/066691; WO 2008/116219; WO 2011/109400; WO 2012/147713, and Table 5). Additional desired antibodies may be made by isolating antibody-secreting hybridomas elicited using B7-H3 expressing cells; B7-H3 or a peptide fragment thereof.

Human B7-H3 exists as a "2Ig" form and as a "418g" form. The amino acid sequence of the "2Ig" form of human B7-H3 (including a 29 amino acid residue signal sequence, shown underlined) is (SEQ ID NO:17):

```
MLRRRGSPGM GVHVGAALGA LWFCLTGALE VQVPEDPVVA
LVGTDATLCC SFSPEPGFSL AQLNLIWQLT DTKQLVHSFA
EGQDQGSAYA NRTALFPDLL AQGNASLRLQ RVRVADEGSF
TCFVSIRDFG SAAVSLQVAA PYSKPSMTLE PNKDLRPGDT
VTITCSSYRG YPEAEVFWQD GQGVPLTGNV TTSQMANEQG
LFDVHSVLRV VLGANGTYSC LVRNPVLQQD AHGSVTITGQ
PMTFPPEALW VTVGLSVCLI ALLVALAFVC WRKIKQSCEE
ENAGAEDQDG EGEGSKTALQ PLKHSDSKED DGQEIA
```

The amino acid sequence of the "2Ig" form of human B7-H3 (SEQ ID NO:17) is completely embraced within the "4Ig" form of human B7-H3(SEQ ID NO:18, the 29 amino acid residue signal sequence, shown underlined):

```
MLRRRGSPGM GVHVGAALGA LWFCLTGALE VQVPEDPVVA
LVGTDATLCC SFSPEPGFSL AQLNLIWQLT DTKQLVHSFA
EGQDQGSAYA NRTALFPDLL AQGNASLRLQ RVRVADEGSF
TCFVSIRDFG SAAVSLQVAA PYSKPSMTLE PNKDLRPGDT
VTITCSSYQG YPEAEVFWQD GQGVPLTGNV TTSQMANEQG
LFDVHSILRV VLGANGTYSC LVRNPVLQQD AHSSVTITPQ
RSPTGAVEVQ VPEDPVVALV GTDATLRCSF SPEPGFSLAQ
LNLIWQLTDT KQLVHSFTEG RDQGSAYANR TALFPDLLAQ
GNASLRLQRV RVADEGSFTC FVSIRDFGSA AVSLQVAAPY
SKPSMTLEPN KDLRPGDTVT ITCSSYRGYP EAEVFWQDGQ
GVPLTGNVTT SQMANEQGLF DVHSVLRVVL GANGTYSCLV
RNPVLQQDAH GSVTITGQPM TFPPEALWVT VGLSVCLIAL
LVALAFVCWR KIKQSCEEEN AGAEDQDGEG EGSKTALQPL
KHSDSKEDDG QEIA
```

Preferred anti-B7-H3-binding molecules possess the VL and/or VH Domains, of the anti-human B7-H3 monoclonal antibody "BRCA84D," "BRCA69D," "PRCA1," or any of the anti-B7-H3 antibodies provided in Table 5; and more preferably possess 1, 2 or all 3 of the $CDR_L$s of the VL Region and/or 1, 2 or all 3 of the $CDR_H$s of the VH Domain of such anti-B7-H3 monoclonal antibodies. Particularly preferred, are B7-H3-binding molecules which possess a humanized VH and/or VL Domain. Such preferred B7-H3-binding molecules include antibodies having variant Fc Domains, bispecific (or multispecific) antibodies, chimeric or humanized antibodies, etc.

1. BRCA84D

The amino acid sequence of the VL Domain of BRCA84D (SEQ ID NO:19) is shown below ($CDR_L$ residues are shown underlined).

```
DIAMTQSQKF MSTSVGDRVS VTCKASQNVD TNVAWYQQKP
GQSPKALIYS ASYRYSGVPD RFTGSGSGTD FTLTINNVQS
EDLAEYFCQQ YNNYPFTFGS GTKLEIK
```

The amino acid sequence of the VH Domain of BRCA84D (SEQ ID NO:20) is shown below ($CDR_H$ residues are shown underlined).

```
DVQLVESGGG LVQPGGSRKL SCAASGFTFS SFGMHWVRQA
PEKGLEWVAY ISSDSSAIYY ADTVKGRFTI SRDNPKNTLF
LQMTSLRSED TAMYYCGRGR ENIYYGSRLD YWGQGTTLTV
SS
```

a. hBRCA84D

Six exemplary humanized VL Domains of BRCA84D designated herein as "hBRCA84D VL1," "BRCA84D VL2," "hBRCA84D VL3," "hBRCA84D VL4," "hBRCA84D VL5," "hBRCA84D VL6," and four exemplary humanized VH Domains of BRCA84D designated herein as "hBRCA84D VH1," "hBRCA84D VH2," "hBRCA84D VH3," and "hBRCA84D VH4," are provided below. Any of the humanized VL Domains may be paired with any of the humanized VH Domains to generate a B7-H3 binding domain. Accordingly, any antibody comprising one of the humanized VL Domains paired with the humanized VH Domain is referred to generically as "hBRCA84D," and particular combinations of humanized VH/VL Domains are referred to by reference to the specific VH/VL Domains, for example a humanized antibody comprising hBRCA84D VH1 and hBRCA84D VL2 is specifically referred to as "hBRCA84D (1.2)."

The amino acid sequence of the VL Domain of hBRCA84D VL1 (SEQ ID NO:21) is shown below ($CDR_L$ residues are shown underlined).

```
DIQLTQSPSF LSASVGDRVT ITCKASQNVD TNVAWYQQKP
GKAPKLLIYS ASYRYSGVPS RFSGSGSGTD FTLTISSLQP
EDFATYYCQQ YNNYPFTFGQ GTKLEIK
```

The amino acid sequence of the VL Domain of hBRCA84D VL2 (SEQ ID NO:22) is shown below ($CDR_L$ residues are shown underlined).

```
DIQLTQSPSF LSASVGDRVT ITCKASQNVD TNVAWYQQKP
GKAPKALIYS ASYRYSGVPS RFSGSGSGTD FTLTISSLQP
EDFATYYCQQ YNNYPFTFGQ GTKLEIK
```

The amino acid sequence of the VL Domain of hBRCA84D VL3 (SEQ ID NO:23) is shown below (CDR$_L$ residues are shown underlined).

DIQLTQSPSF LSASVGDRVS VTCKASQNVD TNVAWYQQKP
GKAPKLLIYS ASYRYSGVPS RFSGSGSGTD FTLTISSLQP
EDFATYYCQQ YNNYPFTFGQ GTKLEIK

The amino acid sequence of the VL Domain of hBRCA84D VL4 (SEQ ID NO:24) is shown below (CDR$_L$ residues are shown underlined).

DIQLTQSPSF LSASVGDRVT ITCKASQNVD TNVAWYQQKP
GQAPKLLIYS ASYRYSGVPS RFSGSGSGTD FTLTISSLQP
EDFATYYCQQ YNNYPFTFGQ GTKLEIK

The amino acid sequence of the VL Domain of hBRCA84D VL5 (SEQ ID NO:25) is shown below (CDR$_L$ residues are shown underlined).

DIQLTQSPSF LSASVGDRVT ITCKASQNVD TNVAWYQQKP
GQAPKALIYS ASYRYSGVPS RFSGSGSGTD FTLTISSLQP
EDFATYYCQQ YNNYPFTFGQ GTKLEIK

The amino acid sequence of the VL Domain of hBRCA84D VL6 (SEQ ID NO:26) is shown below (CDR$_L$ residues are shown underlined).

DIQLTQSPSF LSASVGDRVT ITCKASQNVD TNVAWYQQKP
GKAPKLLIYS ASYRYSGVPS RFSGSGSGTD FTLTISSLQP
EDFAEYYCQQ YNNYPFTFGQ GTKLEIK

The amino acid sequence of the VH Domain of hBRCA84D VH1 (SEQ ID NO:27) is shown below (CDR$_H$ residues are shown underlined).

EVQLVESGGG LVQPGGSLRL SCAASGFTFS SFGMHWVRQA
PGKGLEWVAY ISSDSSAIYY ADTVKGRFTI SRDNAKNSLY
LQMNSLRDED TAVYYCARGR ENIYYGSRLD YWGQGTTVTV
SS

The amino acid sequence of the VH Domain of hBRCA84D VH2 (SEQ ID NO:28) is shown below (CDR$_H$ residues are shown underlined).

EVQLVESGGG LVQPGGSLRL SCAASGFTFS SFGMHWVRQA
PGKGLEWVAY ISSDSSAIYY ADTVKGRFTI SRDNAKNSLY
LQMNSLRDED TAVYYCGRGR ENIYYGSRLD YWGQGTTVTV
SS

The amino acid sequence of the VH Domain of hBRCA84D VH3 (SEQ ID NO:29) is shown below (CDR$_H$ residues are shown underlined).

EVQLVESGGG LVQPGGSLRL SCAASGFTFS SFGMHWVRQA
PGKGLEWVAY ISSDSSAIYY ADTVKGRFTI SRDNAKNSLY
LQMNSLRDED TAMYYCGRGR ENIYYGSRLD YWGQGTTVTV
SS

The amino acid sequence of the VH Domain of hBRCA84D VH4 (SEQ ID NO:30) is shown below (CDR$_H$ residues are shown underlined).

EVQLVESGGG LVQPGGSLRL SCAASGFTFS SFGMHWVRQA
PGKGLEWVAY ISSDSSAIYY ADTVKGRFTI SRDNAKNSLY
LQMNSLRSED TAVYYCARGR ENIYYGSRLD YWGQGTTVTV
SS

2. BRCA69D

The amino acid sequence of the VL Domain of BRCA69D (SEQ ID NO:31) is shown below (CDR$_L$ residues are shown underlined).

DIQMTQTTSS LSASLGDRVT ISCRASQDIS NYLNWYQQKP
DGTVKLLIYY TSRLHSGVPS RFSGSGSGTD YSLTIDNLEQ
EDIATYFCQQ GNTLPPTFGG GTKLEIK

The amino acid sequence of the VH Domain of BRCA69D (SEQ ID NO:32) is shown below (CDR$_H$ residues are shown underlined).

QVQLQQSGAE LARPGASVKL SCKASGYTFT SYWMQWVKQR
PGQGLEWIGT IYPGDGDTRY TQKFKGKATL TADKSSSTAY
MQLSSLASED SAVYYCARRG IPRLWYFDVW GAGTTVTVSS a. hBRCA69D

Two exemplary humanized VL Domains of BRCA69D designated herein as "hBRCA69D VL1," and "hBRCA69D VL2," and two exemplary humanized VH Domains of BRCA69D designated herein as "hBRCA69D VH1," and "hBRCA69D VH2," are provided below. It will be noted that hBRCA69D VL2 includes amino acid substitutions in CDR$_L$1 and CDR$_L$2, and that hBRCA69D VH2 includes amino acid substitutions in CDR$_L$2. Any of the humanized VL Domains may be paired with any of the humanized VH Domains to generate a B7-H3 binding domain. Accordingly, any antibody comprising one of the humanized VL Domains paired with the humanized VH Domain is referred to generically as "hBRCA69D," and particular combinations of humanized VH/VL Domains are referred to by reference to the specific VH/VL Domains, for example a humanized antibody comprising hBRCA69D VH1 and hBRCA69D VL2 is specifically referred to as "hBRCA69D (1.2)."

The amino acid sequence of the VL Domain of hBRCA69D VL1 (SEQ ID NO:33) is shown below ($CDR_L$ residues are shown underlined).

```
DIQMTQSPSS LSASVGDRVT ITCRASQDIS NYLNWYQQKP
GKAPKLLIYY TSRLHSGVPS RFSGSGSGTD FTLTISSLQP
EDIATYYCQQ GNTLPPTFGG GTKLEIK
```

The amino acid sequence of the VL Domain of hBRCA69D VL2 (SEQ ID NO:34) is shown below ($CDR_L$ residues are shown underlined).

```
DIQMTQSPSS LSASVGDRVT ITCRASQSIS SYLNWYQQKP
GKAPKLLIYY TSRLQSGVPS RFSGSGSGTD FTLTISSLQP
EDIATYYCQQ GNTLPPTFGG GTKLEIK
```

The amino acid sequence of the VH Domain of hBRCA69D VH1 is (SEQ ID NO:35) ($CDR_H$ residues are shown underlined):

```
QVQLVQSGAE VKKPGASVKV SCKASGYTFT SYWMQWVRQA
PGQGLEWMGT IYPGDGDTRY TQKFKGRVTI TADKSTSTAY
MELSSLRSED TAVYYCARRG IPRLWYFDVW GQGTTVTVSS
```

The amino acid sequence of the VH Domain of hBRCA69D VH2 is (SEQ ID NO:36) ($CDR_H$ residues are shown underlined):

```
QVQLVQSGAE VKKPGASVKV SCKASGYTFT SYWMQWVRQA
PGQGLEWMGT IYPGGGDTRY TQKFQGRVTI TADKSTSTAY
MELSSLRSED TAVYYCARRG IPRLWYFDVW GQGTTVTVSS
```

3. PRCA157

The amino acid sequence of the VL Domain of PRCA157 (SEQ ID NO:37) is shown below ($CDR_H$ residues are shown underlined).

```
DIQMTQSPAS LSVSVGETVT ITCRASESIY SYLAWYQQKQ
GKSPQLLVYN TKTLPEGVPS RFSGSGSGTQ FSLKINSLQP
EDFGRYYCQH HYGTPPWTFG GGTNLEIK
```

The amino acid sequence of the VH Domain of PRCA157 (SEQ ID NO:38) is shown below ($CDR_H$ residues are shown underlined).

```
EVQQVESGGD LVKPGGSLKL SCAASGFTFS SYGMSWVRQT
PDKRLEWVAT INSGGSNTYY PDSLKGRFTI SRDNAKNTLY
LQMRSLKSED TAMYYCARHD GGAMDYWGQG TSVTVSS
```

4. Additional Anti-B7-H3 Antibodies

Additional anti-B7-H3 antibodies which may be utilized in the methods and compositions of the instant invention are provided in Table 5.

TABLE 5

Anti-B7-H3 Antibodies

| B7-H3 Antibodies | Reference |
|---|---|
| LUCA1; BLA8; PA20; and SKIN2 | U.S. Pat. No. 7,527,969; 8,779,098; and PCT Patent Publication WO 2004/001381 |
| M30; cM30; M30-H1-L1; M30-H1-L2; M30-H1-L3; M30-H1-L4; M30-H1-L5; M30-H1-L6; M30-H1-L7; M30-H4-L1; M30-H4-L2; M30-H4-L3; and M30-H4-L4 | U.S. Patent Publication 2013/0078234; and PCT Patent Publication WO 2012/147713 |
| 8H9 | U.S. Pat. No. 7,666,424; 7,737,258; 7,740,845; 8,148,154; 8,414,892; 8,501,471; 9,062,110; U.S. Patent Publication 2010/0143245; and PCT Patent Publication WO 2008/116219 |

5. Exemplary Anti-B7-H3 Antibodies

In certain embodiments B7-H3 antibodies useful in the methods and compositions of the instant inventions comprise the VL and VH Domains of any of the antibodies provided above (e.g., hBRCA84D, hBRCA69D, PRCA157, or the VL and VH Domains of any of the anti-B7-H3 antibodies in Table 5), a kappa CL Domain, and a variant IgG1 Fc Domain having enhanced ADCC (relative to a wild-type Fc Domain). In one embodiment, the CH2-CH3 Domains comprise the L235V, F243L, R292P, Y300L and P396L substitutions (wherein the numbering is according to the EU index as in Kabat). Such antibodies will preferably comprise an IgG1 CHI Domain and Hinge Domain.

The amino acid sequence of a kappa CL Domain (SEQ ID NO:13) is shown below.

```
RTVAAPSVFI FPPSDEQLKS GTASVVCLLN NFYPREAKVQ
WKVDNALQSG NSQESVTEQD SKDSTYSLSS TLTLSKADYE
KHKVYACEVT HQGLSSPVTK SFNRGEC
```

The amino acid sequence of an IgGI CH1 Domain and Hinge (SEQ ID NO:14) is shown below.

```
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKRVEP KSCDKTHTCP PCP
```

The amino acid sequence of IgGI CH2-CH3 Domains comprising L235V, F243L, R292P, Y300L and P396L substitutions (SEQ ID NO:15) is shown below.

APELVGGPSV FLLPPKPKDT LMISRTPEVT CVVVDVSHED

PEVKFNWYVD GVEVHNAKTK PPEEQYNSTL RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPLVLDS DGSFFLYSKL TVDKSRWQQG NVFSCSVMHE

ALHNHYTQKS LSLSPGK

An exemplary anti-B7-H3 antibody designated "hBRCA84D-2" comprises: a light chain having the VL Domain of BRCA84D VL2 (SEQ ID NO:22) and a kappa CL (SEQ ID NO:13); and a heavy chain having the VH Domain of BRCA84D VH2 (SEQ ID NO:28), an IgGI CHI Domain and Hinge (SEQ ID NO:14), and variant IgG CH2-CH3 Domains comprising L235V, F243L, R292P, Y300L and P396L substitutions (SEQ ID NO:15).

The amino acid sequence of the complete light chain of hBRCA84D-2 (SEQ ID NO:39) is shown below.

DIQLTQSPSF LSASVGDRVT ITCKASQNVD TNVAWYQQKP

GKAPKALIYS ASYRYSGVPS RFSGSGSGTD FTLTISSLQP

EDFATYYCQQ YNNYPFTFGQ GTKLEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC

The amino acid sequence of the complete heavy chain of hBRCA84D-2 (SEQ ID NO:40) is shown below.

EVQLVESGGG LVQPGGSLRL SCAASGFTFS SFGMHWVRQA

PGKGLEWVAY ISSDSSAIYY ADTVKGRFTI SRDNAKNSLY

LQMNSLRDED TAVYYCGRGR ENIYYGSRLD YWGQGTTVTV

SSASTKGPSV FPLAPSSKST SGGTAALGCL VKDYFPEPVT

VSWNSGALTS GVHTFPAVLQ SSGLYSLSSV VTVPSSSLGT

QTYICNVNHK PSNTKVDKRV EPKSCDKTHT CPPCPAPELV

GGPSVFLLPP KPKDTLMISR TPEVTCVVVD VSHEDPEVKF

NWYVDGVEVH NAKTKPPEEQ YNSTLRVVSV LTVLHQDWLN

GKEYKCKVSN KALPAPIEKT ISKAKGQPRE PQVYTLPPSR

EEMTKNQVSL TCLVKGFYPS DIAVEWESNG QPENNYKTTP

LVLDSDGSFF LYSKLTVDKS RWQQGNVFSC SVMHEALHNH

YTQKSLSLSP GK

C. PD-1-Binding Molecules

Molecules that specifically bind PD-1 encompassed by the invention include anti-PD-1 antibodies capable of binding to a continuous or discontinuous (e.g., conformational) portion (epitope) of human PD-1, and molecules comprising the epitope-binding site of such antibodies. The PD-1-binding molecules (e.g., antibodies) used in the methods and compositions of the present invention will preferably also exhibit the ability to bind to the PD-1 molecules of one or more non-human species, especially, murine, rodent, canine, and primate species. Antibodies that are specific for PD-1 are known (see, e.g., U.S. Patent Application No. 62/198,867; U.S. Pat. Nos. 5,952,136; 7,488,802; 7,521,051; 8,008,449; 8,088,905; 8,354,509; 8,552,154; 8,779,105; 8,900,587; 9,084,776; PCT Patent Publications WO 2004/056875; WO 2006/121168; WO 2008/156712; WO 2012/135408; WO 2012/145493; WO 2013/014668; WO 2014/179664; WO 2014/194302; and WO 2015/112800, and Table 6). Additional desired antibodies may be made by isolating antibody-secreting hybridomas elicited using PD-1 or a peptide fragment thereof.

Human PD-1 (including a 20 amino acid residue signal sequence (shown underlined) and the 268 amino acid residue mature protein) has the amino acid sequence (SEQ ID NO:41):

<u>MQIPQAPWPV VWAVLQLGWR</u> PGWFLDSPDR PWNPPTFSPA

LLVVTEGDNA TFTCSFSNTS ESFVLNWYRM SPSNQTDKLA

AFPEDRSQPG QDCRFRVTQL PNGRDFHMSV VRARRNDSGT

YLCGAISLAP KAQIKESLRA ELRVTERRAE VPTAHPSPSP

RPAGQFQTLV VGVVGGLLGS LVLLVWVLAV ICSRAARGTI

GARRTGQPLK EDPSAVPVFS VDYGELDFQW REKTPEPPVP

CVPEQTEYAT IVFPSGMGTS SPARRGSADG PRSAQPLRPE

DGHCSWPL

Preferred anti-PD-1-binding molecules (e.g., antibodies) useful in the methods and compositions of the instant invention possess the VL and/or VH Domains of the anti-human PD-1 monoclonal antibody "PD-1 mAb 1" (nivolumab, CAS Reg. No.: 946414-94-4, also known as 5C4, BMS-936558, ONO-4538, MDX-1106, and marketed as OPDIVO® by Bristol-Myers Squibb); "PD-1 mAb 2" (pembrolizumab, (formerly known as lambrolizumab), CAS Reg. No.: 1374853-91-4, also known as MK-3475, SCH-900475, and marketed as KEYTRUDA® by Merck); "PD-1 mAb 3" (EH12.2H7; Dana Farber), "PD-1 mAb 4" (pidilizumab, CAS Reg. No.: 1036730-42-3 also known as CT-011, CureTech), or any of the anti-PD-1 antibodies in Table 6; and more preferably possess 1, 2 or all 3 of the $CDR_L$s of the VL Region and/or 1, 2 or all 3 of the $CDR_H$s of the VH Domain of such anti-PD-1 monoclonal antibodies. Additional anti-PD-1 antibodies possessing unique binding characteristics useful in the methods and compositions of the instant inventions have recently been identified (see, U.S. Patent Application No. 62/198,867). Particularly, preferred are PD-1-binding molecules which possess a humanized VH and/or VL Domain of the anti-PD-1 antibody "PD-1 mAb 5" (hPD-1 mAb 2, MacroGenics); "PD-1 mAb 6" (hPD-1 mAb 7, MacroGenics); "PD-1 mAb 7" (hPD-1 mAb 9, MacroGenics); or "PD-1 mAb 8" (hPD-1 mAb 15, MacroGenics); and more preferably possess 1, 2 or all 3 of the $CDR_L$s of the VL Region and/or 1, 2 or all 3 of the $CDR_H$s of the VH Domain of such humanized anti-PD-1 monoclonal antibodies. Such preferred anti-PD-1-binding molecules include antibodies having variant Fc Domains, bispecific (or multi-specific) antibodies, chimeric or humanized antibodies, etc.

1. PD-1 mAb 1

The amino acid sequence of the VH Domain of PD-1 mAb 1 (SEQ ID NO:42) is shown below ($CDR_H$ residues are shown underlined).

QVQLVESGGG VVQPGRSLRL DCKASGITFS NSGMHWVRQA

PGKGLEWVAV IWYDGSKRYY ADSVKGRFTI SRDNSKNTLF

LQMNSLRAED TAVYYCATND DYWGQGTLVT VSS

The amino acid sequence of the VL Domain of PD-1 mAb 1 (SEQ ID NO:43) is shown below ($CDR_L$ residues are shown underlined).

EIVLTQSPAT LSLSPGERAT LSCRASQSVS SYLAWYQQKP

GQAPRLLIYD ASNRATGIPA RFSGSGSGTD FTLTISSLEP

EDFAVYYCQQ SSNWPRTFGQ GTKVEIK

2. PD-1 mAb 2

The amino acid sequence of the VH Domain of PD-1 mAb 2 (SEQ ID NO:44) is shown below ($CDR_H$ residues are shown underlined).

QVQLVQSGVE VKKPGASVKV SCKASGYTFT NYYMYWVRQA

PGQGLEWMGG INPSNGGTNF NEKFKNRVTL TTDSSTTTAY

MELKSLQFDD TAVYYCARRD YRFDMGFDYW GQGTTVTVSS

The amino acid sequence of the VL Domain of PD-1 mAb 2 (SEQ ID NO:45) is shown below ($CDR_L$ residues are shown underlined).

EIVLTQSPAT LSLSPGERAT LSCRASKGVS TSGYSYLHWY

QQKPGQAPRL LIYLASYLES GVPARFSGSG SGTDFTLTIS

SLEPEDFAVY YCQHSRDLPL TFGGGTKVEI K

3. PD-1 mAb 3

The amino acid sequence of the VH Domain of PD-1 mAb 3 (SEQ ID NO:46) is shown below ($CDR_H$ residues are shown underlined).

QVQLQQSGAE LAKPGASVQM SCKASGYSFT SSWIHWVKQR

PGQGLEWIGY IYPSTGFTEY NQKFKDKATL TADKSSSTAY

MQLSSLTSED SAVYYCARWR DSSGYHAMDY WGQGTSVTVSS

The amino acid sequence of the VL Domain of PD-1 mAb 3 (SEQ ID NO:47) is shown below ($CDR_L$ residues are shown underlined).

DIVLTQSPAS LTVSLGQRAT ISCRASQSVS TSGYSYMHWY

QQKPGQPPKL LIKFGSNLES GIPARFSGSG SGTDFTLNIH

PVEEEDTATY YCQHSWEIPY TFGGGTKLEI K

4. PD-1 mAb 4

The amino acid sequence of the VH Domain of PD-1 mAb 4 (SEQ ID NO:48) is shown below ($CDR_H$ residues are shown underlined).

QVQLVQSGSE LKKPGASVKI SCKASGYTFT NYGMNWVRQA

PGQGLQWMGW INTDSGESTY AEEFKGRFVF SLDTSVNTAY

LQITSLTAED TGMYFCVRVG YDALDYWGQG TLVTVSS

The amino acid sequence of the VL Domain of PD-1 mAb 4 (SEQ ID NO:49) is shown below ($CDR_L$ residues are shown underlined).

EIVLTQSPSS LSASVGDRVT ITCSARSSVS YMHWFQQKPG

KAPKLWIYRT SNLASGVPSR FSGSGSGTSY CLTINSLQPE

DFATYYCQQR SSFPLTFGGG TKLEIK

5. PD-1 mAb

The amino acid sequence of the VH Domain of PD-1 mAb 5 (SEQ ID NO:50) is shown below ($CDR_H$ residues are shown underlined).

EVQLVESGGG LVQPGGSLRL SCAASGFVFS SFGMHWVRQA

PGKGLEWVAY ISSGSMSISY ADTVKGRFTI SRDNAKNTLY

LQMNSLRTED TALYYCASLS DYFDYWGQGT TVTVSS

The amino acid sequence of the VL Domain of PD-1 mAb 5 (SEQ ID NO:51) is shown below ($CDR_L$ residues are shown underlined).

DVVMTQSPLS LPVTLGQPAS ISCRSSQSLV HSTGNTYLHW

YLQKPGQSPQ LLIYRVSNRF SGVPDRFSGS GSGTDFTLKI

SRVEAEDVGV YYCSQTTHVP WTFGQGTKLE IK

6. PD-1 mAb 6

The amino acid sequence of the VH Domain of PD-1 mAb 6 (SEQ ID NO:52) is shown below ($CDR_H$ residues are shown underlined).

QVQLVQSGAE VKKPGASVKV SCKASGYSFT SYWMNWVRQA

PGQGLEWXGV IHPSDSETWL DQKFKDRVTI TVDKSTSTAY

MELSSLRSED TAVYYCAREH YGTSPFAYWG QGTLVTVSS wherein X is I or A

The amino acid sequence of the VL Domain of PD-1 mAb 6 (SEQ ID NO:53) is shown below ($CDR_L$ residues are shown underlined).

EIVLTQSPAT LSLSPGERAT LSCRAX$_1$ESVD NYGMSFMNWF

QQKPGQPPKL LIHAASNX$_2$GS GVPSRFSGSG SGTDFTLTIS

SLEPEDFAVY FCQQSKEVPY TFGGGTKVEI K wherein: $X_1$ is N or S and $X_2$ is Q or R or $X_1$ is N and $X_2$ is Q; or $X_1$ is S and $X_2$ is Q; or $X_1$ is S and $X_2$ is R In particular embodiments PD-1 mAb 6 comprises:

(a) SEQ ID NO:52, wherein X is I; and SEQ ID NO:53, wherein $X_1$ is N and $X_2$ is Q; or (b) SEQ ID NO:52, wherein X is I; and SEQ ID NO:53, wherein $X_1$ is S and $X_2$ is Q.

7. PD-1 mAb 7

The amino acid sequence of the VH Domain of PD-1 mAb 7 (SEQ ID NO:54) is shown below ($CDR_H$ residues are shown underlined).

EVQLVESGGG LX$_1$RPGGSLKL SCAASGFTFS SYLVX$_2$WVRQA

PGKGLEWX$_3$AT ISGGGGNTYY SDSVKGRFTI SRDNAKNSLY

LQMNSX$_4$RAED TATYYCARYG FDGAWFAYWG QGTLVTVSS wherein $X_1$ is V or A; $X_2$ is S or G; $X_3$ is V or T; $X_4$ is L or A; $X_1$ is V, $X_2$ is S, $X_3$ is V, and $X_4$ is L; or $X_1$ is A, $X_2$ is G, $X_3$ is T, and $X_4$ is A The amino acid sequence of the VL Domain of PD-1 mAb 7 (SEQ ID NO:55) is shown below ($CDR_L$ residues are shown underlined).

DIQMTQSPSS LSASVGDRVT ITCRASENIY X$_1$YLAWYQQKP

GKAPKLLIYX$_2$ AKTLAAGVPS RFSGSGSGTD FTLTISSLQP

EDFATYYCQH HYAVPWTFGQ GTKLEIK wherein: $X_1$ is S or N and $X_2$ is N or D; or $X_1$ is S and $X_2$ is N; or $X_1$ is N and $X_2$ is D In particular embodiments PD-1 mAb 7 comprises:

(a) SEQ ID NO:54, wherein $X_1$ is V, $X_2$ is S, $X_3$ is V, and $X_4$ is L; and SEQ ID NO:55, wherein $X_1$ is S and $X_2$ is N; or (b) SEQ ID NO:54, wherein $X_1$ is A, $X_2$ is G, $X_3$ is T, and $X_4$ is A; and SEQ ID NO:55, wherein $X_1$ is N and $X_2$ is D. 8. PD-1 mAb 8

The amino acid sequence of the VH Domain of PD-1 mAb 8 (SEQ ID NO:56) is shown below ($CDR_H$ residues are shown underlined).

EVQLVESGGG LVRPGGSLRL SCAASGFTFS SYLISWVRQA

PGKGLEWVAA ISGGGADTYY ADSVKGRFTI SRDNAKNSLY

LQMNSLRAED TATYYCARRG TYAMDYWGQG TLVTVSS

The amino acid sequence of the VL Domain of PD-1 mAb 8 (SEQ ID NO:57) is shown below ($CDR_L$ residues are shown underlined).

DIQMTQSPSS LSASVGDRVT ITCRASENIY NYLAWYQQKP

GKAPKLLIYD AKTLAAGVPS RFSGSGSGTD FTLTISSLQP

EDFATYYCQH HYAVPWTFGQ GTKLEIK

9. Additional Anti-PD-1 Antibodies

Additional anti-PD-1 antibodies which may be utilized in the methods and compositions of the instant invention are provided in Table 6.

TABLE 6

Additional Anti-PD-1 Antibodies

| PD-1 Antibodies | Reference |
|---|---|
| PD1-17; PD1-28; PD1-33; PD1-35; and PD1-F2 | U.S. Pat. No. 7,488,802; 7,521,051 8,088,905; and PCT Patent Publication WO 2004/056875 |
| 17D8; 2D3; 4H1; 5C4; 4A11; 7D3; and 5F4 | U.S. Pat. No. 8,008,449; 8,779,105; 9,084,776; and PCT Patent Publication WO 2006/121168 |
| hPD-1.08A; hPD-1.09A; 109A; K09A; 409A; h409A11; h409A16; h409A17; Codon optimized 109A; and Codon optimized 409A | U.S. Pat. No. 8,354,509; 8,900,587; 5,952,136; and PCT Patent Publication WO 2008/156712 |
| 1E3; 1E8; and 1H3 | U.S. Patent Publication 2014/0044738; and PCT Patent Publication WO 2012/145493 |
| 9A2; 10B11; 6E9; APE1922; APE1923; APE1924; APE1950; APE1963; and APE2058 | PCT Patent Publication WO 2014/179664 |
| GA1; GA2; GB1; GB6; GH1; A2; C7; H7; SH-A4; SH-A9; RG1H10; RG1H11; RG2H7; RG2H10; RG3E12; RG4A6; RG5D9; RG1H10-H2A-22-1S; RG1H10-H2A-27-2S; RG1H10-3C; RG1H10-16C; RG1H10-17C; RG1H10-19C; RG1H10-21C; and RG1H10-23C2 | U.S. Patent Publication 2014/0356363; and PCT Patent Publication WO 2014/194302 |
| H1M7789N; H1M7799N; H1M7800N; H2M7780N; H2M7788N; H2M7790N; H2M7791N; H2M7794N; H2M7795N; H2M7796N; H2M7798N; H4H9019P; H4xH9034P2; H4xH9035P2; H4xH9037P2; H4xH9045P2; H4xH9048P2; H4H9057P2; H4H9068P2; H4xH9119P2; H4xH9120P2; H4Xh9128p2; H4Xh9135p2; H4Xh9145p2; H4Xh8992p; H4Xh8999p; and H4Xh9008p; | U.S. Patent Publication 2015/0203579; and PCT Patent Publication WO 2015/112800 |
| PD-1 mAb 1; PD-1 mAb 2; hPD-1 mAb 2; PD-1 mAb 3; PD-1 mAb 4; PD-1 mAb 5; PD-1 mAb 6; PD-1 mAb 7; hPD-1 mAb 7; PD-1 mAb 8; PD-1 mAb 9; hPD-1 mAb 9; PD-1 mAb 10; PD-1 mAb 11; PD-1 mAb 12; PD-1 mAb 13; PD-1 mAb 14; PD-1 mAb 15; and hPD-1 mAb 15 | U.S. patent application No. 62/198,867 |

10. Exemplary PD-1 Antibodies

In certain embodiments PD-1 antibodies useful in the methods and compositions of the instant inventions comprise the VL and VH Domains of any of the antibodies provided above (e.g., PD-1 mAb 1, PD-1 mAb 2, PD-1 mAb 3, PD-1 mAb 4, PD-1 mAb 5, PD-1 mAb 6, PD-1 mAb 7, PD-1 mAb 8, or any of the anti-PD-1 antibodies in Table 6), a kappa CL Domain, and an IgG4 Fc Domain, optionally lacking the C-terminal lysine residue. Such antibodies will preferably comprise an IgG4 CHI Domain and a Hinge Domain, and more preferably comprise a stabilized IgG4 Hinge comprising an S228P substitution (wherein the numbering is according to the EU index as in Kabat).

The amino acid sequence of a kappa CL Domain (SEQ ID NO:13) has been presented above.

The amino acid sequence of an IgG4 CHI Domain and Stabilized Hinge (SEQ ID NO:16) has been presented above.

The amino acid sequence of IgG4 CH2-CH3 Domains (SEQ ID NO:4) has been presented above.

An exemplary anti-PD-1 antibody designated "PD-1 mAb 6-ISQ" comprises: a light chain having the VL Domain of PD-1 mAb 6 (SEQ ID NO:53) wherein $X_1$ is S and $X_2$ is Q and a kappa CL (SEQ ID NO:13); and a heavy chain having the VH Domain of PD-1 mAb 6 (SEQ ID NO:52) wherein $X_1$ is I, an IgG4 CHI Domain, a stabilized IgG 4 Hinge (SEQ ID NO:16), and IgG4 CH2-CH3 Domains (SEQ ID NO:4).

The amino acid sequence of the complete light chain of PD-1 mAb 6-ISQ (SEQ ID NO:58) is shown below.

```
EIVLTQSPAT LSLSPGERAT LSCRASESVD NYGMSFMNWF
QQKPGQPPKL LIHAASNQGS GVPSRFSGSG SGTDFTLTIS
SLEPEDFAVY FCQQSKEVPY TFGGGTKVEI KRTVAAPSVF
IFPPSDEQLK SGTASVVCLL NNFYPREAKV QWKVDNALQS
GNSQESVTEQ DSKDSTYSLS STLTLSKADY EKHKVYACEV
THQGLSSPVT KSFNRGEC
```

The amino acid sequence of the complete heavy chain of PD-1 mAb 6-ISQ (SEQ ID NO:59) is shown below.

```
QVQLVQSGAE VKKPGASVKV SCKASGYSFT SYWMNWVRQA
PGQGLEWIGV IHPSDSETWL DQKFKDRVTI TVDKSTSTAY
MELSSLRSED TAVYYCAREH YGTSPFAYWG QGTLVTVSSA
STKGPSVFPL APCSRSTSES TAALGCLVKD YFPEPVTVSW
NSGALTSGVH TFPAVLQSSG LYSLSSVVTV PSSSLGTKTY
TCNVDHKPSN TKVDKRVESK YGPPCPPCPA PEFLGGPSVF
LFPPKPKDTL MISRTPEVTC VVVDVSQEDP EVQFNWYVDG
VEVHNAKTKP REEQFNSTYR VVSVLTVLHQ DWLNGKEYKC
KVSNKGLPSS IEKTISKAKG QPREPQVYTL PPSQEEMTKN
QVSLTCLVKG FYPSDIAVEW ESNGQPENNY KTTPPVLDSD
GSFFLYSRLT VDKSRWQEGN VFSCSVMHEA LHNHYTQKSL
SLSLG
```

Another exemplary anti-PD-1 antibody is PD-1 mAb 1 (nivolumab), which is a human antibody comprising a light chain having a VL Domain (SEQ ID NO:43) and a kappa CL Domain (see for example, SEQ ID NO:13); and a heavy chain having a VH Domain (SEQ ID NO:42), an IgG4 CHI Domain (see for example, SEQ ID NO:9), a stabilized IgG4 Hinge (see for example, SEQ ID NO:12), and IgG4 CH2-CH3 Domains (see for example, SEQ ID NO:4).

Another exemplary anti-PD-1 antibody is PD-1 mAb 2 (pembrolizumab), which is a humanized antibody comprising a light chain having a VL Domain (SEQ ID NO:45) and a kappa CL Domain (see for example, SEQ ID NO:13); and a heavy chain having a VH Domain (SEQ ID NO:44), an IgG4 CHI Domain (see for example, SEQ ID NO:9), a stabilized IgG4 Hinge (see for example, SEQ ID NO:12), and IgG4 CH2-CH3 Domains (see for example, SEQ ID NO:4).

D. Methods of Production

B7-H3-binding molecules and PD-1-binding molecules encompassed by the present invention can be produced by methods known in the art, for example, synthetically or recombinantly (see, e.g., Kelley, R. F. et al. (1990) In: Genetic Engineering Principles and Methods, Setlow, J. K. Ed., Plenum Press, N.Y., vol. 12, pp 1-19; Stewart, J. M et al. (1984) Solid Phase Peptide Synthesis, Pierce Chemical Co., Rockford, Ill.; see also U.S. Pat. Nos. 4,105,603; 3,972,859; 3,842,067; and 3,862,925; Merrifield, B. (1986) "*Solid Phase Synthesis*," Science 232(4748):341-347; Houghten, R. A. (1985) "*General Method For The Rapid Solid-Phase Synthesis Of Large Numbers Of Peptides: Specificity Of Antigen-Antibody Interaction At The Level Of Individual Amino Acids*," Proc. Natl. Acad. Sci. (U.S.A.) 82(15):5131-5135; Ganesan, A. (2006) "*Solid-Phase Synthesis In The Twenty-First Century*," Mini Rev. Med. Chem. 6(1):3-10).

Alternatively, suitable B7-H3-binding molecules and/or PD-1-binding molecules having one or more of the CDRs of a desired anti-B7-H3 antibody and/or anti-PD-1 antibody may be obtained through the use of commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ (Abgenix, Inc., Fremont, Calif.) and HuMAb-Mouse® and TC Mouse™ (both from Medarex, Inc., Princeton, N.J.).

In a further alternative method, such binding molecules may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants (e.g., tobacco) or transgenic milk. Suitable methods for expressing antibodies recombinantly in plants or milk have been disclosed (see, for example, Peeters et al. (2001) "*Production Of Antibodies And Antibody Fragments In Plants*," Vaccine 19:2756; Lonberg, N. et al. (1995) "*Human Antibodies From Transgenic Mice*," Int. Rev. Immunol 13:65-93; and Pollock et al. (1999) "*Transgenic Milk As A Method For The Production Of Recombinant Antibodies*," J. Immunol Methods 231:147-157). Suitable methods for making derivatives of antibodies, e.g., humanized antibodies, bispecific antibodies, single-chain, etc. are known in the art. In another alternative, antibodies may be made recombinantly by phage display technology (see, for example, U.S. Pat. Nos. 5,565,332; 5,580,717; 5,733,743; 6,265,150; and Winter, G. et al. (1994) "*Making Antibodies By Phage Display Technology*," Annu. Rev. Immunol. 12.433-455).

Vectors containing polynucleotides encoding polypeptides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cell capable of overexpressing heterologous DNAs can be used for the purpose of isolating the genes encoding the antibody, polypeptide or protein of interest. Non-limiting examples of suitable mammalian host cells include but are not limited to COS, HeLa, and CHO cells. Preferably, the host cells express the cDNAs at a level of about 5-fold higher, more preferably 10-fold higher, even more preferably 20-fold higher than that of the corresponding endogenous antibody or protein of interest, if present, in the host cells. Screening the host cells for immunospecific binding to a cDNA expressed target (e.g., B7-H3 or PD-1) may be accomplished using an immunoassay or FACS. A cell overexpressing the antibody or protein of interest can be identified.

The invention includes polypeptides comprising an amino acid sequence (preferably the epitope binding domain) of an anti-B7-H3 antibody and/or anti-PD-1-antibody provided herein. The polypeptides of this invention can be made by procedures known in the art. The polypeptides can be produced by proteolytic or other degradation of antibodies, by recombinant methods (i.e., single or fusion polypeptides) as described above or by chemical synthesis. Polypeptides, especially shorter polypeptides up to about 50 amino acids, are conveniently made by chemical synthesis.

The invention includes modifications of the polypeptides of any such B7-H3-binding molecules and/or PD-1-binding molecules that do not significantly affect the properties of such molecules as well as variants that have enhanced or decreased activity. The modification of polypeptides is a routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; serine/threonine; valine/isoleucine/leucine; asparagine/glutamine; aspartic acid/glutamic acid; lysine/arginine; and phenylalanine/tyrosine. These polypeptides also include glycosylated and non-glycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the Variable Domain. Changes in the Variable Domain can alter binding affinity and/or immunospecificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

The invention encompasses fusion proteins comprising one or more of the antibodies of this invention. In one embodiment, a fusion polypeptide is provided that comprises a light chain, a heavy chain or both a light and heavy chain. In another embodiment, the fusion polypeptide contains a heterologous immunoglobulin constant region. In another embodiment, the fusion polypeptide contains a VL Domain and a VH Domain of an antibody provided herein or produced from a publicly-deposited hybridoma. For purposes of this invention, an antibody fusion protein contains one or more epitope-binding sites that immunospecifically bind to B7-H3 and/or PD-1, and one or more polypeptide domains that immunospecifically bind to another amino acid sequence to which it is not attached in the native molecule, for example, a heterologous sequence or a homologous sequence from another region.

E. Pharmaceutical Compositions

The present invention encompasses compositions comprising a B7-H3-binding molecule, a PD-1-binding molecule, or a combination of such molecules. The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a B7-H3-binding molecule, a PD-1-binding molecule, or a combination of such molecules and a pharmaceutically acceptable carrier. Preferably, compositions of the invention comprise a B7-H3-binding molecule, a PD-1-binding molecule, or a combination of such molecules, and a pharmaceutically acceptable carrier. In a preferred aspect, such compositions are substantially purified (i.e., substantially free from substances that limit its effect or produce undesired side effects).

Where more than one therapeutic agent is to be administered the agents may be formulated together in the same formulation or may be formulated into separate compositions. Accordingly, in some embodiments, the B7-H3-binding molecule and the PD-1-binding molecule are formulated together in the same pharmaceutical composition. In alternative embodiments, the molecules are formulated in separate pharmaceutical compositions.

Various formulations of a B7-H3-binding molecule, a PD-1-binding molecule, or a combination of such molecules, may be used for administration. In addition to the pharmacologically active agent(s), the compositions of the present invention may contain suitable pharmaceutically acceptable carriers comprising excipients and auxiliaries that are well known in the art and are relatively inert substances that facilitate administration of a pharmacologically effective substance or which facilitate processing of the active compounds into preparations that can be used pharmaceutically for delivery to the site of action. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Aqueous carriers, such as saline solutions, aqueous dextrose and glycerol solutions are preferred when the pharmaceutical composition is administered intravenously. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain a minor amount of a wetting or emulsifying agent, or a pH buffering agent. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed using an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Preferably, the therapeutic agent (i.e., a B7-H3-binding molecule, a PD-1-binding molecule, or a combination of such molecules) is supplied as a dry sterile lyophilized powder in a hermetically sealed container such as an ampoule or sachette indicating the quantity of the molecule(s). In one embodiment, the therapeutic agent is supplied as a dry sterilized lyophilized powder or water free concentrate in a hermetically sealed container and can be reconstituted, e.g., with water or saline to the appropriate concentration for administration to a subject. In an alternative embodiment, the therapeutic agent is supplied in liquid form in a hermetically sealed container indicating the quantity and concentration of the therapeutic agent.

The lyophilized therapeutic agent (i.e., a B7-H3-binding molecule, a PD-1-binding molecule, or a combination of such molecules) should be stored at between 2° C. and 8° C. in the original container and the agent should be administered within 12 hours, preferably within 6 hours, within 5 hours, within 3 hours, or within 1 hour after being reconstituted. In an alternative embodiment, the therapeutic agent is supplied in liquid form in a hermetically sealed container indicating the quantity and concentration of the molecule(s), fusion protein, or conjugated molecule. Preferably, such therapeutic agent when provided in liquid form is supplied in a hermetically sealed container.

The invention also provides a pharmaceutical pack or kit comprising one or more containers containing a B7-H3-binding molecule, a PD-1-binding molecule, or a combination of such molecules alone or with other agents, preferably with a pharmaceutically acceptable carrier. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

A kit can comprise a B7-H3-binding molecule, a PD-1-binding molecule, or a combination of such molecules. The kit can further comprise one or more other prophylactic and/or therapeutic agents useful for the treatment of cancer, in one or more containers; and/or the kit can further comprise one or more cytotoxic antibodies that bind one or more cancer antigens. In certain embodiments, the other prophylactic or therapeutic agent is a chemotherapeutic agent. In other embodiments, the prophylactic or therapeutic agent is a biological or hormonal therapeutic agent.

F. Methods of Use

As discussed above, molecules that specifically bind to B7-H3 and molecules that specifically bind to PD-1 may be used for therapeutic purposes in subjects with cancer or other diseases. Accordingly the present invention provides methods of treating cancer, comprising administering to a subject in need thereof a B7-H3-binding molecule and a PD-1-binding molecule. In particular, the present invention encompasses such methods wherein, the B7-H3-binding molecule comprises the epitope-binding site of an anti-B7-H3 antibody provided herein, and wherein the PD-1-binding molecule comprises the epitope-binding site of an anti-PD-1 antibody provided herein. In one embodiment the B7-H3-binding molecule is an antibody. In one embodiment, the PD-1-binding molecule is an antibody. In a further embodiment, both the B7-H3-binding molecule and PD-1-binding molecule are antibodies.

In one embodiment, a B7-H3-binding molecule and a PD-1-binding molecule are administered concurrently. As used herein, such "concurrent" administration is intended to denote:

(A) the administration of a single pharmaceutical composition that contains both a B7-H3-binding molecule and a PD-1-binding molecule. Such molecules may be the same molecule (e.g., a bispecific antibody), or may be distinct (e.g., an anti-B7-H3 antibody, or antigen-binding fragment thereof, and an anti-PD-1-antibody, or antigen-binding fragment thereof); or (B) the separate administration of two or more pharmaceutical compositions, one composition of which contains a molecule that specifically binds to B7-H3 and another composition of which contains a molecule that specifically binds to PD-1, wherein the compositions are administered within a 48-hour period.

In a second embodiment, two distinct molecules are employed, and the molecules are administered "sequentially" (e.g., an anti-B7-H3 antibody is administered and, at a later time, an anti-PD-1 antibody is provided, or vice versa). In such sequential administration, the second administered composition is administered at least 48 hours, or more after the administration of the first administered composition.

Providing a therapy or "treating" refers to any indicia of beneficial or desired results including, without limitation, clinical results such as shrinking the size of a tumor (in the cancer context, for example, a tumor of breast, gastric or prostate cancer), retardation of cancer cell growth, delaying the development of metastasis, decreasing a symptom resulting from the disease, increasing the quality of life of those suffering from the disease, decreasing the dose of other medications required to treat the disease, enhancing the effect of another medication such as via targeting and/or internalization, delaying the progression of the disease, and/or prolonging survival of an individual.

Subjects for treatment include animals, most preferably mammalian species such as non-primate (e.g., bovine, equine, feline, canine, rodent, etc.) or a primate (e.g., monkey, such as, cynomolgus monkey, human, etc.). In a preferred embodiment, the subject is a human.

Exemplary disorders that may be treated by various embodiments of the present invention include, but are not limited to, proliferative disorders, cell proliferative disorders, and cancer (especially a B7-H3-expressing cancer). In various embodiments, the invention encompasses methods and compositions for treatment, prevention or management of a disease or disorder in a subject, comprising administering to the subject a therapeutically effective amount a molecule that specifically binds to B7-H3 and a molecule that specifically binds to PD-1. For example, the B7-H3-binding molecule and the PD-1-binding molecule are particularly useful for the prevention, inhibition, reduction of growth or regression of primary tumors, and metastasis of cancer cells. Although not intending to be bound by a particular mechanism of action, such binding molecules may mediate effector function against cancer cells, promote the activation of the immune system against cancer cells, cross-link cell-surface antigens and/or receptors on cancer cells and enhance apoptosis or negative growth regulatory signaling, or a combination thereof, resulting in tumor clearance and/or tumor reduction.

As used herein, an "effective amount" of a pharmaceutical composition, in one embodiment, is an amount sufficient to effect beneficial or desired results including, without limitation, clinical results such as decreasing symptoms resulting from the disease attenuating a symptom of infection (e.g., viral load, fever, pain, sepsis, etc.) or a symptom of cancer (e.g., the proliferation, of cancer cells, tumor presence, tumor metastases, etc.), thereby increasing the quality of life of those suffering from the disease, decreasing the dose of other medications required to treat the disease, enhancing the effect of another medication such as via targeting and/or internalization, delaying the progression of the disease, and/or prolonging survival of individuals. When applied to an individual active ingredient, administered alone, the term refers to that ingredient alone. When applied to a combination, the term refers to combined amounts of the active ingredients that result in the therapeutic effect, whether administered in combination, serially, or simultaneously. Particular dosages are discussed below.

In one embodiment, a B7-H3-binding molecule (e.g., an antibody) and a PD-1-binding molecule (e.g., an antibody) can be used to treat any disease or condition associated with or characterized by the expression of B7-H3. Thus, without limitation, the methods and compositions of the instant invention may be used for immunotherapy directed at cancer including cancers characterized by the presence of a cancer cell, including but not limited to a cell of an acute myeloid leukemia, an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, a glioblastoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a malignant mesothelioma, a multiple endocrine neoplasia, a multiple myeloma, a myelodysplastic syndrome, a neuroblastoma, a neuroendocrine tumors, a non-small cell lung cancer, an ovarian cancer, a pancreatic cancer, a pharyngeal cancer, a papillary thyroid carcinoma, a parathyroid tumor, a pediatric cancer, a peripheral nerve sheath tumor, a phaeochromocytoma, a pituitary tumor, a prostate cancer, a posterious uveal melanoma, a rare hematologic disorder, a renal cell carcinoma, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer. Such immunotherapy may, for example, be sufficient to reduce cell division in the cancer cell, delay the development (e.g., onset and extent) of metastasis, and/or to promote the activity of the immune system on the cancer cells.

In particular, the combination of a B7-H3-binding molecule and a PD-1-binding molecule is particularly useful for the treatment of squamous cell cancers of the head and neck (SCCHN), bladder cancers, breast cancers, colorectal cancers, gastric cancers, glioblastomas, kidney cancers, lung cancers including non-small cell lung cancers (NSCLC), melanomas, ovarian cancers, pancreatic cancers, pharyngeal cancers, prostate cancers, renal cell carcinomas, and small round blue cell tumors of childhood including neuroblastomas and rhabdomyosarcomas, each of which highly express B7-H3.

It is understood that the B7-H3-binding molecules and PD-1-binding molecules are administered at a concentration that promotes binding at physiological (e.g., in vivo) conditions. The B7-H3-binding molecules and PD-1-binding molecules (e.g., anti-B7-H3 and anti-PD-1 antibodies) may be administered with additional agents that enhance or direct an individual's own immune response, such as an agent that strengthens ADCC or stimulated T-cells.

In yet another embodiment, the B7-H3-binding molecule and/or the PD-1-binding molecule may be conjugated to or associated with a radioactive molecule, toxin (e.g., calicheamicin), chemotherapeutic molecule, liposomes or other vesicles containing chemotherapeutic compounds and administered to an individual in need of such treatment to target these compounds to the cancer cell containing the antigen recognized by the B7-H3-binding molecule and thus eliminate cancer or diseased cells. Without being limited to any particular theory, the B7-H3-binding molecule (e.g., an anti-B7-H3 antibody) is internalized by the cell bearing B7-H3 at its surface, thus delivering the conjugated moiety to the cell to induce the therapeutic effect and the PD-1-binding molecule promotes the activation of the immune system.

In yet another embodiment, the B7-H3-binding molecule and PD-1-binding molecule (e.g., anti-B7-H3 and anti-PD-1 antibodies) can be employed as an adjuvant therapy at the time of the surgical removal of a tumor in order to delay, suppress or prevent the development of metastasis. The molecules can also be administered before surgery (neoadjuvant therapy) in order to decrease the size of the tumor and thus enable or simplify surgery, spare tissue during surgery, and/or decrease any resulting disfigurement.

Molecules having an Fc Domain with an increased affinity for FcγRIIIA and/or FcγRIIA, and optionally a decreased affinity for FcγRIIB, may lead to an enhanced activating response upon FcγR binding and thus have enhanced therapeutic efficacy for treating and/or preventing cancer. Accordingly, B7-H3-binding molecules comprising a variant Fc Domain are particularly useful for the treatment and/or prevention of a disease, or disorder where an effector cell function (e.g., ADCC) mediated by FcγR is desired (e.g., cancer). For example, a B7-H3-binding molecule having enhanced FcγRIIIA binding may bind a cell-surface antigen and FcγRIIIA on an immune effector cell (e.g., NK cell), stimulating an effector function (e.g., ADCC, CDC, phagocytosis, opsonization, etc.) against the cell. In some embodiments, the B7-H3-binding molecules provided herein are especially suited for the treatment of cancers. The efficacy of standard monoclonal antibody therapy depends on the FcγR polymorphism of the subject. Cartron, G. et al. (2002) "*Therapeutic Activity Of Humanized Anti CD20 Monoclonal Antibody And Polymorphism In IgG Fc Receptor FcgammaRIIIa Gene*," Blood 99:754-758; Weng, W. K. et al. (2003) "*Two Immunoglobulin G Fragment C Receptor Polymorphisms Independently Predict Response To Rituximab In Patients With Follicular Lymphoma*," J Clin Oncol. 21(21): 3940-3947. These receptors are expressed on the surface of the effector cells and mediate ADCC. High affinity alleles improve the effector cells' ability to mediate ADCC. In particular the B7-H3-binding molecules provided herein comprising a variant Fc Domain that exhibits enhanced affinity to FcγRIIIA (relative to a wild-type Fc Domain) on effector cells are better immunotherapy reagents for patients regardless of their FcγR polymorphism.

G. Administration and Dosage

A combination of a B7-H3-binding molecule and a PD-1-binding molecule, may be provided for the treatment, prophylaxis, and amelioration of one or more symptoms associated with cancer or other disease, or disorder by administering to a subject an effective amount of such a combination, or pharmaceutical composition(s) comprising the same. In any of the embodiments below, the cancer is preferably a B7-H3 expressing cancer.

As used herein, the term "combination" refers to the use of more than one therapeutic agent (e.g., a B7-H3-binding molecule and a PD-1-binding molecule). The use of the term "combination" does not restrict the order in which therapeutic agents are administered to a subject with a disorder, nor does it mean that the agents are administered at exactly the same time, but rather it is meant that the agents are administered to a subject in a sequence and within a time interval such that the agents can act to provide an increased benefit than if they were administered otherwise. For example, each therapeutic agent (e.g., (i.e., a B7-H3-binding molecule and a PD-1-binding molecule) may be administered at the same time or sequentially in any order and/or at different points in time so as to provide the desired therapeutic or prophylactic effect. Furthermore, each agent need not be administered for the entire course of treatment. For example, both agents may be administered for a period of time, after which one agent is discontinued. Each therapeutic agent can be administered separately, in any appropriate form and by any suitable route, e.g., one by the oral route and one parenterally.

A variety of delivery systems and administration routes for providing a combination of a B7-H3-binding molecule and a PD-1-binding molecule are available. Delivery systems that can be used to administer a B7-H3-binding molecule and a PD-1-binding molecule, include, but are not limited to, encapsulation in liposomes, microparticles, microcapsules, recombinant cells capable of expressing the antibody or fusion protein, receptor-mediated endocytosis (See, e.g., Wu et al. (1987) "*Receptor-Mediated In Vitro Gene Transformation By A Soluble DNA Carrier System*." J. Biol. Chem. 262:4429-4432), construction of a nucleic acid as part of a retroviral or other vector, etc. Methods of administering a B7-H3-binding molecule and a PD-1-binding molecule, include, but are not limited to, parenteral administration (e.g., intradermal, intramuscular, intraperitoneal, intravenous and subcutaneous), epidural, and mucosal (e.g., intranasal and oral routes). In a specific embodiment, molecules are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

Treatment of a subject with a therapeutically or prophylactically effective amount of a B7-H3-binding molecule and/or a PD-1-binding molecule can include a single treatment or, preferably, can include a series of treatments. For example, a subject may be treated with a B7-H3-binding molecule and/or a PD-1-binding molecule once a week, twice a week, once every two weeks, once every three weeks, once every four weeks, once every six weeks, once every two months for between about 2 to about 52 weeks. It will be appreciated that the effective dosage of the molecules used for treatment may increase or decrease over the course of a particular treatment. As provided herein, the B7-H3-binding molecule and the PD-1-binding molecule need not be administered at the same time or at the same intervals or for the same number of treatments.

Preferably the B7-H3-binding molecule and the PD-1-binding molecule are administered using a treatment regimen comprising one or more doses, wherein the treatment regimen is administered over 1 week, 2 weeks, 3 weeks, 4 week, 6 weeks, 8 or more than 8 weeks. In certain embodiments, the treatment regimen comprises intermittently administering doses of the effective amount of such molecules (for example, administering a dose on week one and week four and not administering doses of the molecule on week two or week three). Typically, there are 1, 2, 3, 4, 5 or more than 5 courses of treatment. Each course may be the same regimen or a different regimen.

The dosage of a B7-H3-binding molecule, a PD-1-binding molecule, or a combination of such molecules, administered to a patient is typically at least about at least about 1.0 mg/kg body weight, at least about 3 mg/kg body weight, at least about 5 mg/kg body weight, at least about 10 mg/kg body weight, at least about 15 mg/kg body weight, or at least about 20 mg/kg. For antibodies encompassed by the invention, the dosage administered to a patient is typically 1.0 mg/kg to 20 mg/kg of the patient's body weight. Preferably, the dosage administered to a patient is between 1.0 mg/kg and 20 mg/kg, 1.0 mg/kg and 10 mg/kg, 1.0 mg/kg and 5 mg/kg, 2.0 mg/kg and 20 mg/kg, or 5 mg/kg and 20 mg/kg of the patient's body weight. In one embodiment, the dosage administered to a patient is between 1 mg/kg and 15 mg/kg body weight. In another embodiment, the dosage administered to a patient is 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, or 15 mg/kg, 16 mg/kg, 17 mg/kg, 18 mg/kg, 19 mg/kg, or 20 mg/kg body weight. The calculated dose will be administered based on the patient's body weight at baseline. Significant (>10%) change in body weight from baseline or established plateau weight should prompt recalculation of dose.

Alternatively, a fixed dosage of a B7-H3-binding molecule, a PD-1-binding molecule, or a combination of such molecules is administered to a patient regardless of body weight. For antibodies encompassed by the invention, the fixed dosage administered to a patient is typically between 50 mg to 500 mg. Preferably, the fixed dosage administered to a patient is between 50 mg and 300 mg, 100 mg and 300 mg, or 100 mg and 200 mg. In one embodiment, the fixed dosage administered to a patient is 100 mg, 200 mg or 300 mg.

In various embodiments, a first therapeutic agent (e.g., anti-B7-H3 antibody or anti-PD-1 antibody) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second (or subsequent) therapeutic agent (e.g., anti-B7-H3 antibody or anti-PD-1 antibody) to a subject with a disorder. In preferred embodiments, two or more agents are administered within the same patient visit.

As provided herein, the B7-H3-binding molecule and the PD-1-binding molecule may be administered at different dosages, different concentrations, different times and/or on different schedules.

Although, as discussed above, various dosing regimens and administration routes may be employed in order to provide a combination of a molecule that specifically binds to B7-H3 and a molecule that specifically binds to PD-1 to recipient subjects in need thereof in accordance with the present invention, certain combinations, dosing regimens and administrative routes are particularly preferred for use in such treatment. The use of an anti-B7-H3 antibody (e.g., hBRCA84D-2) alone and in combination with an anti-PD-1 antibody (e.g., pembrolizumab) in such dosing and administrative is particularly preferred.

In certain embodiments, a dose of an anti-B7-H3 antibody is administered weekly in combination with a dose of an anti-PD-1 antibody administered every two or three weeks (wherein each administration of such a combination treatment regimen is herein referred to as a "cycle"). In one embodiment, 1 to 15 mg/kg patient body weight, preferably 1, 2, 3, 4, 5, 6, 7, 8, 9, 10, 11, 12, 13, 14, or 15 mg/kg body weight, of an anti-B7-H3 antibody is administered weekly. In one embodiment, either 1 to 10 mg/kg patient body weight, preferably 1, 2, 3, 4, 5, 6, 7, 8, 9, or 10 mg/kg body weight, of an anti-PD-1 antibody or a fixed 100, 200, or 300 mg dose of an anti-PD-1 antibody is administered once every two or three weeks until remission of disease or unmanageable toxicity is observed.

In particularly preferred embodiments, an anti-B7-H3 antibody is administered to the subject by IV infusion weekly and an anti-PD-1 antibody is administered to the subject by IV infusion every two or three weeks for a duration of at least 1 month or more, at least 3 months or more, or at least 6 months or more, or at least 12 months or more. A treatment duration of at least 6 months or more, or for at least 12 months or more, or until remission of disease or unmanageable toxicity is observed, is particularly preferred. In such IV administration once every two or three weeks, an anti-B7-H3 antibody and an anti PD-1 antibody may be administered together or sequentially. In particularly preferred embodiments, an anti-B7-H3 antibody and an anti-PD-1 antibody are administered to the subject sequentially by IV infusion no more than 48 hours apart. In such sequential administration an anti-B7-H3 antibody may be administered prior to, or subsequent to, the administration of an anti-PD-1 antibody.

It is particularly preferred to provide a subject with multiple doses of a combination treatment of an anti-B7-H3 antibody and an anti-PD-1 antibody. A treatment regimen may thus comprise 1 cycle, at least 2 cycles or more than 2 cycles, at least 3 cycles or more than 3 cycles, at least 4 cycles or more than 4 cycles, at least 5 cycles or more than 5 cycles, or at least 6 cycles or more than 6 cycles. The dosage of each antibody in each such cycle may be the same or may vary from the prior administered dosage.

It is preferred that the antibodies not be administered as an IV push or bolus, but rather that such administration be accomplished by IV infusion. The antibodies are thus preferably diluted into an infusion bag comprising a suitable diluent, e.g., 0.9% sodium chloride. Since infusion or allergic reactions may occur, premedication for the prevention of such infusion reactions is recommended and precautions for anaphylaxis should be observed during the antibody administration. It is particularly preferable for the IV infusion to be administered to the subject over a period of between 30 minutes and 24 hours. In certain embodiments, the IV infusion is preferably delivered over a period of 30-180 minutes, or 30-120 minutes, or 30-90 minutes, or over a period of 60 minutes, or over a lesser period, if the subject does not exhibit signs or symptoms of an adverse infusion reaction.

Accordingly, a preferred method of treating cancer is provided, the method comprising administering to a subject in need thereof a combination of an anti-B7-H3 antibody and an anti-PD-1 antibody, wherein the anti-B7-H3 antibody is administered at a dosage of 1 to 15 mg/kg body weight weekly and the anti-PD-1 antibody is administered at a fixed dosage of 200 mg every three weeks. In one embodiment, the anti-B7-H3 antibody is administered at a dosage of 1, 3, 10, or 15 mg/kg body weight. In a further embodiment, the anti-B7-H3 antibody is administered at a dosage of 1 mg/kg weekly and the anti-PD-1 antibody is administered at a fixed dosage of 200 mg every three weeks. In a further embodiment, the anti-B7-H3 antibody is administered at a dosage of 3 mg/kg body weight weekly and the anti-PD-1 antibody is administered at a fixed dosage of 200 mg every three weeks. In a further embodiment, the anti-B7-H3 antibody is administered at a dosage of 10 mg/kg body weight weekly and the anti-PD-1 antibody is administered at a fixed dosage of 200 mg every three weeks. In a further embodiment, the anti-B7-H3 antibody is administered at a dosage of 15 mg/kg body weight weekly and the anti-PD-1 antibody is administered at a fixed dosage of 200 mg every three weeks. In any of the above embodiments, the anti-B7-H3 antibody and the anti-PD-1 antibody are administered by IV infusion, and when administered in the same week, both may be administered within a 48 hour, preferably 24 hour period.

Another preferred method of treating cancer is provided, the method comprising administering to a subject in need thereof a combination of an anti-B7-H3 antibody and an anti-PD-1 antibody, wherein the dosage of the anti-B7-H3 antibody is 1 to 15 mg/kg body weight weekly, and the dosage of the anti-PD-1 antibody is 1 to 10 mg/kg body weight every two or three weeks. In one embodiment, the dosage of the anti-B7-H3 antibody is 1, 3, 10, or 15 mg/kg body weight. In a further embodiment, the dosage of the anti-PD-1 antibody is 1, 2, 3 or 10 mg/kg body weight. In a further embodiment, the dosage of the anti-B7-H3 antibody is 1 mg/kg body weight and the dosage of the anti-PD-1 antibody is 1 mg/kg body weight. In a further embodiment, the dosage of the anti-B7-H3 antibody is 1 mg/kg and the dosage of the anti-PD-1 antibody is 2 mg/kg body weight. In a further embodiment, the dosage of the anti-B7-H3 antibody is 1 mg/kg body weight and the dosage of the anti-PD-1 antibody is 3 mg/kg body weight. In a further embodiment, the dosage of the anti-B7-H3 antibody is 1 mg/kg and the dosage of the anti-PD-1 antibody is 10 mg/kg body weight. In a further embodiment, the dosage of the anti-B7-H3 antibody is 3 mg/kg body weight and the dosage of the anti-PD-1 antibody is 1 mg/kg body weight. In a further embodiment, the dosage of the anti-B7-H3 antibody is 3 mg/kg body weight and the dosage of the anti-PD-1 antibody is 2 mg/kg body weight. In a further embodiment, the dosage of the anti-B7-H3 antibody is 3 mg/kg body weight and the dosage of the anti-PD-1 antibody is 3 mg/kg body weight. In a further embodiment, the dosage of the anti-B7-H3 antibody is 3 mg/kg body weight and the dosage of the anti-PD-1 antibody is 10 mg/kg body weight. In a further embodiment, the dosage of the anti-B7-H3 antibody is 10 mg/kg body weight and the dosage of the anti-PD-1 antibody is 1 mg/kg body weight. In a further embodiment, the dosage of the anti-B7-H3 antibody is 10 mg/kg body weight and the dosage of the anti-PD-1 antibody is 2 mg/kg body weight. In a further embodiment, the dosage of the anti-B7-H3 antibody is 10 mg/kg body weight and the dosage of the anti-PD-1 antibody is 3 mg/kg body weight. In a further embodiment, the dosage of the anti-B7-H3 antibody is 10 mg/kg body weight and the dosage of the anti-PD-1 antibody is 10 mg/kg body weight. In a further embodiment, the dosage of the anti-B7-H3 antibody is 15 mg/kg body weight and the dosage of the anti-PD-1 antibody is 1 mg/kg body weight. In a further embodiment, the dosage of the anti-B7-H3 antibody is 15 mg/kg body weight and the dosage of the anti-PD-1 antibody is 2 mg/kg body weight. In a further embodiment, the dosage of the anti-B7-H3 antibody is 15 mg/kg body weight and the dosage of the anti-PD-1 antibody is 3 mg/kg body weight. In a further embodiment, the dosage of the anti-B7-H3 antibody is 15 mg/kg body weight and the dosage of the anti-PD-1 antibody is 10 mg/kg body weight. In any of the above embodiments, the anti-B7-H3 antibody and the anti-PD-1 antibody are administered by IV infusion, and once every two or three weeks may both be administered within a 48 hour, preferably 24 hour period.

In any of the above embodiments, the anti-B7-H3 antibody comprises the $CDR_L1$ $CDR_L2$, $CDR_L3$, $CDR_HI$, $CDR_H2$, and $CDR_H3$ Domains of hBRCA84D, hBRCA69D, PRCA157, or the $CDR_L1$ $CDR_L2$, $CDR_L3$, $CDR_HI$, $CDR_H2$, and $CDR_H3$ Domains of any of the anti-B7-H3 antibody provided in Table 5, and the anti-PD-1 antibody comprises the $CDR_L1$ $CDR_L2$, $CDR_L3$, $CDR_HI$, $CDR_H2$, and $CDR_H3$ Domains of PD-1 mAb 1, PD-1 mAb 2, PD-1 mAb 3, PD-1 mAb 4, PD-1 mAb 5, PD-1 mAb 6, PD-1 mAb 7, PD-1 mAb 8, or the $CDR_L1$ $CDR_L2$, $CDR_L3$, $CDR_HI$, $CDR_H2$, and $CDR_H3$ Domains of any of the anti-PD-1 antibodies provided in Table 6. In any of the above embodiments, the anti-B7-H3 antibody is hBRCA84D-2 and the anti-PD-1 antibody is selected from the antibodies provided in Table 6. In a preferred embodiment, the anti-B7-H3 antibody is hBRCA84D-2 and the anti-PD-1 antibody is pembrolizumab. In another preferred embodiment, the anti-B7-H3 antibody is hBRCA84D-2 and the anti-PD-1 antibody is nivolumab. In another preferred embodiment, the anti-B7-H3 antibody is hBRCA84D-2 and the anti-PD-1 antibody is pidilizumab. In another preferred embodiment, the anti-B7-H3 antibody is hBRCA84D-2 and the anti-PD-1 antibody is PD-1 mAb 6-ISQ.

In any of the above embodiments, the therapeutic agents are preferably cyclically administered to a subject. Cycling therapy can reduce the development of resistance to one or more of the therapies, avoid or reduce the side effects of one of the therapies, and/or improves the efficacy of the treatment. Exemplary cycles are about once every week, about once every 10 days, about once every two weeks, and about once every three weeks. Each cycle can comprise at least 1 week of rest, at least 2 weeks of rest, at least 3 weeks of rest, etc. The number of cycles administered is from about 1 to about 12 cycles, more typically from about 2 to about 10 cycles, and more typically from about 2 to about 8 cycles.

A preferred dosage regimen for the therapeutic administration as provided in any of the embodiments above, comprises administering such combination of an anti-B7-H3 antibody and an anti-PD-1 antibody to a recipient subject in an initial cycle, and one or more subsequent cycles. In any of the embodiments provided above, the anti-B7-H3 antibody and the anti-PD-1 antibody are administered on the same cycle schedule. In such embodiments, each cycle comprises two or three weeks, with the anti-B7-H3 antibody being provided to the subject in a weekly administration and the anti-PD-1 antibody being provided to the subject on the first week of each 2- or 3-week period. Alternatively, the anti-B7-H3 antibody and the anti-PD-1 antibody are administered on different cycle schedules. In such embodiments, each cycle for the anti-PD-1 antibody comprises two or three weeks, with the anti-PD-1 antibody being provided to the subject on the first week of each 2 or 3 week period. In such an embodiment, the initial cycle for the anti-B7-H3 antibody will preferably comprise 8 weeks, with the anti-B7-H3 antibody being provided to the subject in a weekly administration for the first four weeks of such 8 week initial period, followed by no administration to the subject for the period of weeks 5-8 of such 8 week initial period. Each subsequent cycle will preferably comprise a 4-week period, with the anti-B7-H3 antibody being provided to the subject in a weekly administration for the first three weeks of such 4-week subsequent period, followed by no administration to the subject for the period of week 4 of such 4 week subsequent period. Thus, for example, a subject would receive the B7-H3 antibody weekly in week 1, 2, 3, 4, 9, 10, 11, 13, 14, 15, etc., wherein weeks 1-8 are the initial dosage regimen cycle, weeks 9-12 are the first subsequent cycle, weeks 13-16 are a second subsequent cycle, etc.

I. Combination Therapies

The invention further encompasses administering to a subject, a combination of a molecule that specifically binds to B7-H3 and a molecule that specifically binds to PD-1 in further combination with other therapies known to those skilled in the art for the treatment or prevention of cancer, autoimmune disease, inflammation, or infectious disease, including but not limited to, current standard and experimental chemotherapies, hormonal therapies, biological therapies, immunotherapies, radiation therapies, or surgery.

In some embodiments, the combination of a B7-H3-binding molecule and a PD-1-binding molecule (e.g., an anti-B7-H3 antibody and an anti-PD-1 antibody) are administered in combination with a therapeutically or prophylactically effective amount of one or more additional therapeutic agents known to those skilled in the art for the treatment and/or prevention of cancer, in particular a B7-H3-expressing cancer.

In an embodiment for the treatment of a cell proliferative disorder, a B7-H3-binding molecule and/or a PD-1-binding molecule (e.g., anti-B7-H3 antibody, anti-PD-1 antibody) is conjugated to, or administered in further combination with, another therapeutic agent, such as, but not limited to, an alkylating agent (e.g., mechlorethamine or cisplatin), angiogenesis inhibitor, anthracycline (e.g., daunorubicin/daunomycin or doxorubicin), antibiotic (e.g., dactinomycin, bleomycin, or anthramycin), antibody (e.g., an anti-VEGF antibody such as bevacizumab (sold as AVASTIN® by Genentech, Inc.), an anti-EGFR antibody such as panitumumab (sold as VECTIBIX™ by Amgen, Inc.), or an anti-integrin antibody such as natalizumab (sold as TYSABRI® by Biogen Idec and Elan Pharmaceuticals, Inc.)), an antimetabolite (e.g., methotrexate or 5-fluorouracil), an anti-mitotic agent (e.g., vincristine or paclitaxel), a cytotoxin (e.g., a cytostatic or cytocidal agent), a hormone therapy agent (e.g., a selective estrogen receptor modulator (e.g., tamoxifen or raloxifene), aromatase inhibitor, luteinizing hormone-releasing hormone analog, progestational agent, adrenocorticosteroid, estrogen, androgen, anti-estrogen agent, androgen receptor blocking agent, 5-alpha reductase inhibitor, adrenal production inhibitor, etc.), a matrix metalloprotease inhibitor, a radioactive element (e.g., alpha-emitters, gamma-emitters, etc.), or any other chemotherapeutic agent.

Non-limiting examples of suitable angiogenesis inhibitors include ABT-627; angiostatin (plasminogen fragment); angiozyme; antiangiogenic antithrombin III; Bay 12-9566; benefin; bevacizumab; BMS-275291; bisphosphonates; cartilage-derived inhibitor (CDI); CAI; CD59 complement fragment; CEP-7055; Col 3; combretastatin A-4; endostatin (collagen XVIII fragment); famesyl transferase inhibitors (FTI); fibronectin fragment; gro-beta; halofuginone; heparinases; heparin hexasaccharide fragment; HMV833; human chorionic gonadotropin (hCG); IM-862; interferon alpha/beta/gamma; interferon inducible protein (IP-10); interleukin-12; kringle 5 (plasminogen fragment); marimastat; metalloproteinase inhibitors (TIMPs); 2-methoxyestradiol; MMI 270 (CGS 27023A); MoAb IMC-1C11; neovastat; NM-3; panzem; PI-88; placental ribonuclease inhibitor; plasminogen activator inhibitor; platelet factor-4 (PF4); prinomastat; prolactin 16 kDa fragment; proliferin-related protein (PRP); PTK 787/ZK 222594; retinoids; solimastat; squalamine; SS 3304; SU 5416; SU6668; SU11248; tetrahydrocortisol-S; tetrathiomolybdate; thalidomide; thrombospondin-1 (TSP-1); TNP-470; transforming growth factor-beta (TGF-b); vasculostatin; vasostatin (calreticulin fragment); ZD6126; and ZD 6474.

Non-limiting examples of additional antibodies for the treatment of a cell proliferative disorder include antibodies to 17-1A, avS3, AFP, CD3, CD18, CD20, CD22, CD33, CD44, CD52, CEA, CTLA-4, DNA-associated proteins, EGF receptor, Ep-CAM, GD2-ganglioside, gp IIIb/IIIa, gp72, HLA-DR 10 beta, HLA-DR antigen, IgE, ganglioside GD3, MUC-1, nuC242, PEM antigen, SK-1 antigen, tumor antigen CA125, tumor antigen MUC1, VEGF, and VEGF-receptor.

EXAMPLES

Having now generally described the invention, the same will be more readily understood through reference to the following examples, which are provided by way of illustration and are not intended to be limiting of the present invention unless specified.

Example 1

Dose-Escalation Study of a Combination of an Anti-B7-H3 Antibody and an Anti-PD-1 Antibody While following dose-escalation study protocol details the use of the exemplary anti-B7-H3 antibody "hBRCA84D-2" in combination with the anti-PD-1 antibody "pembrolizumab," it will be understood in view of the teachings herein that similar combination protocols may be designed using any of anti-B7-H3 antibodies and anti-PD-1 antibodies provided herein.

A dose escalation study is performed to determine the Maximum Tolerated Dose (MTD) or Maximum Administered Dose (MAD) (if no MTD is defined) of escalating doses of hBRCA84D-2 administered weekly in combination with a dose of 2 mg/kg pembrolizumab administered every three weeks. This may be followed by a cohort expansion phase to further define the safety and initial efficacy of the combination with the hBRCA84D-2 dose established in the dose escalation study. hBRCA84D-2 is administered weekly and pembrolizumab is administered once every 3 weeks. Once every three weeks the agents are administered on the same day with pembrolizumab administered first, followed by hBRCA84D-2. However, where the combined dose exceeds 2,500 mg the antibodies should be administered on consecutive days. When administering the antibodies on consecutive days pembrolizumab may be administered on the first day, and hBRCA84D-2 may be administered on the next calendar day. Each cycle of therapy is defined as 3 weeks, in which hBRCA84D-2 is given on Days 1, 8 and 15, and pembrolizumab is given on Day 1. Tumor assessments may be performed during the study, preferably at the end of the first two cycles, and at the end of every subsequent three cycles of treatment (i.e., after 6 weeks [end of Cycle 2] and after 15 weeks, 24 weeks, 33 weeks, etc. [end of Cycle 5, 8, 11, etc.]).

hBRCA84D-2 may be evaluated in three sequential escalating doses, 3 mg/kg body weight, 10 mg/kg, and 15 mg/kg body weight, in combination with 2 mg/kg pembrolizumab in cohort's patients. If it is determined that the MTD is exceeded in the first dose cohort, a dose de-escalation cohort to evaluate a lower dose of hBRCA84D-2 (1 mg/kg) in combination with 2 mg/kg pembrolizumab may be utilized.

For a cohort expansion phase additional patients are enrolled and will receive hBRCA84D-2 at the MTD (or MAD) established from the dose escalation phase of the study in combination with 2 mg/kg pembrolizumab.

Patients who remain clinically stable and do not experience unacceptable toxicity that necessitates permanent discontinuation of the study drugs, at the completion of the first two 3-week cycles will be eligible to receive additional treatment with hBRCA84D-2 and pembrolizumab. Patients that remain clinically stable, maintain a response status of stable disease or better, and do not experience unacceptable toxicity that necessitates permanent discontinuation of the study drugs, patients may receive additional treatment cycles of hBRAC84D-2 and pembrolizumab. Such additional treatment may continue for approximately one year such that patients may receive 51 doses of hBRCA84D-2 and 17 doses of pembrolizumab.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of treating a B7-H3-expressing cancer, comprising administering to a subject in need thereof:

(a) an anti-B7-H3 antibody or an antigen-binding fragment thereof comprising a variable domain that specifically binds to B7-H3 and comprises:

(i) the three complementarity determining regions (CDRs) of a light chain variable domain comprising the amino acid sequence of SEQ ID NO:19; and (ii) the three CDRs of a heavy chain variable domain comprising the amino acid sequence of SEQ ID NO:20, wherein said anti-B7-H3 antibody or antigen-binding fragment thereof is administered at a dosage of about 1-15 mg/kg body weight, in combination with (b) an anti-PD-1 antibody or an antigen-binding fragment thereof comprising a variable domain that specifically binds to PD-1 and comprises:

(i) the three CDRs of a heavy chain variable domain comprising the amino acid sequence of SEQ ID NO:52; and (ii) the three CDRs of a light chain variable domain comprising the amino acid sequence of SEQ ID NO:53, wherein said anti-PD-1 antibody or antigen-binding fragment thereof is administered at:

(i) a fixed dosage of between 50 mg and 500 mg; or (ii) a dosage of about 1-10 mg/kg body weight.

2. The method of claim 1, wherein said anti-B7-H3 antibody or antigen-binding fragment thereof comprises:

a heavy chain variable domain comprising an amino acid sequence selected from the group consisting of SEQ ID NOs:20, 27, 28, 29 and 30, and a light chain variable domain comprising an amino acid sequence selected from the group consisting of SEQ ID NOs:19, 21, 22, 23, 24, 25 and 26.

3. The method of claim 1, wherein said anti-B7-H3 antibody or antigen-binding fragment thereof comprises an Fc Domain, and said anti-PD-1 antibody or antigen-binding fragment thereof comprises an Fc Domain.

4. The method of claim 3, wherein said anti-B7-H3 antibody or antigen-binding fragment thereof comprises a variant Fc Domain having at least one modification in the Fc Domain that enhances ADCC.

5. The method of claim 3, wherein said anti-PD-1 antibody or antigen-binding fragment thereof comprises:

(a) a variant Fc Domain having at least one modification in the Fc Domain that reduces or abolishes ADCC activity; or (b) an IgG4 Fc Domain.

6. The method of claim 1, wherein:

(a) said anti-B7-H3 antibody comprises a light chain comprising the amino acid sequence of SEQ ID NO:39, and a heavy chain comprising the amino acid sequence of SEQ ID NO:40; and (b) said anti-PD-1 antibody comprises a light chain comprising the amino acid sequence of SEQ ID NO:58 and a heavy chain comprising the amino acid sequence of SEQ ID NO:59.

7. The method of claim 1, wherein said anti-PD-1 antibody or antigen-binding fragment thereof is administered at a fixed dosage of between 50 mg to 500 mg.

8. The method of claim 1, wherein said anti-B7-H3 antibody or antigen-binding fragment thereof is administered at a dosage of about 1 mg/kg body weight, about 3 mg/kg body weight, about 10 mg/kg body weight or about 15 mg/kg body weight.

9. The method of claim 8, wherein said anti-PD-1 antibody or antigen-binding fragment thereof is administered at a dosage of about 1 mg/kg body weight, about 2 mg/kg body weight, about 3 mg/kg body weight, about 5 mg/kg body weight, about 6 mg/kg body weight, or about 10 mg/kg body weight.

10. The method of claim 9, wherein said anti-B7-H3 antibody or antigen-binding fragment thereof is administered at a dosage of about 3 mg/kg body weight, about 10 mg/kg body weight, or about 15 mg/kg body weight and said anti-PD-1 antibody or antigen-binding fragment thereof is administered at a dosage of about 5 mg/kg body weight.

11. The method of claim 9, wherein said anti-B7-H3 antibody or antigen-binding fragment thereof is administered at a dosage of about 3 mg/kg body weight, about 10 mg/kg body weight, or about 15 mg/kg body weight, and said anti-PD-1 antibody or antigen-binding fragment thereof is administered at a dosage of about 6 mg/kg body weight.

12. The method of claim 9, wherein said anti-B7-H3 antibody or antigen-binding fragment thereof is administered at a dosage of about 3 mg/kg body weight, about 10 mg/kg body weight, or about 15 mg/kg body weight, and said anti-PD-1 antibody or antigen-binding fragment thereof is administered at a dosage of about 10 mg/kg body weight.

13. The method of claim 1, wherein the anti-PD-1 antibody or antigen-binding fragment thereof is administered every two weeks.

14. The method of claim 1, wherein the anti-PD-1 antibody or antigen-binding fragment thereof is administered every three weeks.

15. The method of claim 1, wherein the anti-B7-H3 antibody or antigen-binding fragment thereof and the anti-PD-1 antibody or antigen-binding fragment thereof are administered by IV infusion.

16. The method of claim 1, wherein every three weeks said anti-B7-H3 antibody or antigen-binding fragment thereof and said anti-PD-1 antibody or antigen-binding fragment thereof are administered within a 48-hour period of each other.

17. The method of claim 1, wherein every two weeks said anti-B7-H3 antibody or antigen-binding fragment thereof and said anti-PD-1 antibody or antigen-binding fragment thereof are administered within a 48-hour period of each other.

18. The method of claim 1, wherein said B7-H3-expressing cancer is selected from the group consisting of: a squamous cell cancer of the head and neck (SCCHN), a bladder cancer, a breast cancer, a colorectal cancer, a gastric cancer, a glioblastoma, a kidney cancer, a lung cancer, a melanoma, an ovarian cancer, a pancreatic cancer, a pharyngeal cancer, a prostate cancer, a renal cell carcinoma, a small round blue cell tumor, a neuroblastoma, and a rhabdomyosarcoma.

19. The method of claim 1, further comprising the step of administering a third therapeutic agent to said subject in need thereof, wherein said third therapeutic agent is selected from the group consisting of an anti-angiogenic agent, an anti-neoplastic agent, a chemotherapeutic agent, and a cytotoxic agent.

20. The method of claim 1, wherein said anti-B7-H3 antibody comprises a light chain comprising the amino acid sequence of SEQ ID NO:39, and a heavy chain comprising the amino acid sequence of SEQ ID NO:40.

21. The method of claim 1, wherein said anti-PD-1 antibody or antigen-binding fragment thereof comprises a heavy chain variable domain comprising the amino acid sequence of SEQ ID NO:52 and a light chain variable domain comprising the amino acid sequence of SEQ ID NO:53.

22. The method of claim 21, wherein said anti-PD-1 antibody comprises a light chain comprising the amino acid sequence of SEQ ID NO:58 and a heavy chain comprising the amino acid sequence of SEQ ID NO:59.

23. The method of claim 10, wherein said anti-B7-H3 antibody is administered at a dosage of about 15 mg/kg body weight every three weeks and said anti-PD-1 antibody is administered at a dosage of about 5 mg/kg body weight every three weeks.

24. The method of claim 23, wherein:

(a) said anti-B7-H3 antibody comprises a light chain comprising the amino acid sequence of SEQ ID NO:39, and a heavy chain comprising the amino acid sequence of SEQ ID NO:40; and (b) said anti-PD-1 antibody comprises a light chain comprising the amino acid sequence of SEQ ID NO:58 and a heavy chain comprising the amino acid sequence of SEQ ID NO:59.

25. The method of claim 8, wherein said anti-B7-H3 antibody or antigen-binding fragment thereof is administered at a dosage of 15 mg/kg body weight every three weeks and said anti-PD-1 antibody or antigen-binding fragment thereof is administered at a fixed dosage of between 50 mg to 500 mg every three weeks.

26. The method of claim 25, wherein said anti-PD-1 antibody or antigen-binding fragment thereof is administered at a fixed dosage of 300 mg every three weeks.

27. The method of claim 26, wherein:

(a) said anti-B7-H3 antibody comprises a light chain comprising the amino acid sequence of SEQ ID NO:39, and a heavy chain comprising the amino acid sequence of SEQ ID NO:40; and (b) said anti-PD-1 antibody comprises a light chain comprising the amino acid sequence of SEQ ID NO:58 and a heavy chain comprising the amino acid sequence of SEQ ID NO:59.

28. The method of claim 1, wherein said anti-PD-1 antibody or antigen-binding fragment thereof is administered at a fixed dosage of 300 mg.

29. The method of claim 7, wherein said anti-PD-1 antibody or antigen-binding fragment thereof is administered at a fixed dosage of 200 mg.

30. The method of claim 25, wherein said anti-PD-1 antibody or antigen-binding fragment thereof is administered at a fixed dosage of 200 mg.

31. The method of claim 1, wherein said anti-PD-1 antibody or antigen-binding fragment thereof is administered at a dosage of 1-10 mg/kg body weight.

32. The method of claim 8, wherein said anti-B7-H3 antibody or antigen-binding fragment thereof is administered at a dosage of 15 mg/kg body weight.

33. The method of claim 1, wherein said anti-B7-H3 antibody or antigen-binding fragment thereof is administered every week.

34. The method of claim 1, wherein said anti-B7-H3 antibody or antigen-binding fragment thereof is administered every three weeks.

35. The method of claim 18, wherein said B7-H3-expressing cancer is a squamous cell cancer of the head and neck (SCCHN).

36. The method of claim 4, wherein said variant Fc Domain of said anti-B7-H3 antibody or antigen-binding fragment thereof comprises any one, any two, any three, any four, or all five of the substitutions L235V, F243L, R292P, Y300L, and P396L, wherein the numbering is according to the Kabat numbering scheme.

37. The method of claim 36, wherein said variant Fc Domain of said anti-B7-H3 antibody or antigen-binding fragment thereof comprises:

(A) at least one substitution selected from the group consisting of F243L, R292P, Y300L, V3051, and P396L;

(B) at least two substitutions selected from the group consisting of:

(1) F243L and P396L;

(2) F243L and R292P; and (3) R292P and V3051;

(C) at least three substitutions selected from the group consisting of:

(1) F243L, R292P and Y300L;

(2) F243L, R292P and V3051;

(3) F243L, R292P and P396L; and (4) R292P, V3051 and P396L;

(D) at least four substitutions selected from the group consisting of:

(1) F243L, R292P, Y300L and P396L; and (2) F243L, R292P, V3051 and P396L; or (E) at least the five substitutions selected from the group consisting of:

(1) F243L, R292P, Y300L, V3051 and P396L; and (2) L235V, F243L, R292P, Y300L and P396L;

wherein the numbering is according to the Kabat numbering scheme.

38. The method of claim 5, wherein said variant Fc Domain of said anti-PD-1 antibody or antigen-binding fragment thereof comprises any one, any two, any three, any four, or all five of the substitutions L234A, L235A, D265A, N297A, N297Q, wherein the numbering is according to the Kabat numbering scheme.

39. The method of claim 38, wherein said variant Fc Domain of said anti-PD-1 antibody or antigen-binding fragment thereof comprises the substitution:

(A) L234A, L235A;

(B) D265A;

(C) N297A; or (D) N297Q;

wherein the numbering is according to the Kabat numbering scheme.

* * * * *

SEQUENCE LISTING

```
<160> NUMBER OF SEQ ID NOS: 62

<210> SEQ ID NO 1
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: CH2-CH3 Domains of Exemplary Human IgG1
<220> FEATURE:
<221> NAME/KEY: MISC_FEATURE
<222> LOCATION: (217)..(217)
<223> OTHER INFORMATION: X is Lysine (K) or absent

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215


<210> SEQ ID NO 2
<211> LENGTH: 216
<212> TYPE: PRT
<213> ORGANISM: Homo sapiens
<220> FEATURE:
<221> NAME/KEY: MISC_FEATURE
<222> LOCATION: (1)..(216)
```

```
<223> OTHER INFORMATION: CH2-CH3 Domains of Exemplary Human IgG2
<220> FEATURE:
<221> NAME/KEY: MISC_FEATURE
<222> LOCATION: (216)..(216)
<223> OTHER INFORMATION: X is Lysine (K) or absent

<400> SEQUENCE: 2

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
    130                 135                 140

Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Xaa
    210                 215


<210> SEQ ID NO 3
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: CH2-CH3 Domains of Exemplary Human IgG3
<220> FEATURE:
<221> NAME/KEY: MISC_FEATURE
<222> LOCATION: (217)..(217)
<223> OTHER INFORMATION: X is Lysine (K) or Absent

<400> SEQUENCE: 3

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
```

```
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly Xaa
    210                 215


<210> SEQ ID NO 4
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: CH2-CH3 Domains of Exemplary Human IgG4
<220> FEATURE:
<221> NAME/KEY: MISC_FEATURE
<222> LOCATION: (217)..(217)
<223> OTHER INFORMATION: X is Lysine (K) or Absent

<400> SEQUENCE: 4

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
```

```
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
    210                 215


<210> SEQ ID NO 5
<211> LENGTH: 217
<212> TYPE: PRT
<213> ORGANISM: Artificial Sequence
<220> FEATURE:
<223> OTHER INFORMATION: Preferred IgG1 CH2 and CH3 Domains Having
      L234A/L235A Substitutions
<220> FEATURE:
<221> NAME/KEY: MISC_FEATURE
<222> LOCATION: (217)..(217)
<223> OTHER INFORMATION: X is Lysine (K) or Absent

<400> SEQUENCE: 5

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215


<210> SEQ ID NO 6
<211> LENGTH: 217
<212> TYPE: PRT
<213> ORGANISM: Artificial Sequence
<220> FEATURE:
<223> OTHER INFORMATION: Preferred “Knob-Bearing” CH2 and CH3 Domains
<220> FEATURE:
<221> NAME/KEY: MISC_FEATURE
<222> LOCATION: (217)..(217)
<223> OTHER INFORMATION: X is Lysine (K) or Absent

<400> SEQUENCE: 6
```

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215
```

<210> SEQ ID NO 7
<211> LENGTH: 217
<212> TYPE: PRT
<213> ORGANISM: Artificial Sequence
<220> FEATURE:
<223> OTHER INFORMATION: Preferred “Hole-Bearing” CH2 and CH3 Domains
<220> FEATURE:
<221> NAME/KEY: MISC_FEATURE
<222> LOCATION: (217)..(217)
<223> OTHER INFORMATION: X is Lysine (K) or Absent

<400> SEQUENCE: 7

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125
```

```
Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Xaa
    210                 215


<210> SEQ ID NO 8
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Exemplary Human IgG1 CH1 Domain

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val


<210> SEQ ID NO 9
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Exemplary Human IgG4 CH1 Domain

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
```

85 90 95

Arg Val

<210> SEQ ID NO 10
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)
<223> OTHER INFORMATION: Exemplary Human IgG1 Hinge Region

<400> SEQUENCE: 10

Glu Pro Lys Ser Cys Asp Lys Thr His Thr Cys Pro Pro Cys Pro
1 5 10 15

<210> SEQ ID NO 11
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Exemplary Human IgG4 Hinge Region

<400> SEQUENCE: 11

Glu Ser Lys Tyr Gly Pro Pro Cys Pro Ser Cys Pro
1 5 10

<210> SEQ ID NO 12
<211> LENGTH: 12
<212> TYPE: PRT
<213> ORGANISM: Artificial Sequence
<220> FEATURE:
<223> OTHER INFORMATION: IgG4 Fc Domain Containing S228P Stabilizing
Hinge Mutation at Position 10

<400> SEQUENCE: 12

Glu Ser Lys Tyr Gly Pro Pro Cys Pro Pro Cys Pro
1 5 10

<210> SEQ ID NO 13
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: Human Kappa CL Domain

<400> SEQUENCE: 13

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys

```
            100                 105


<210> SEQ ID NO 14
<211> LENGTH: 113
<212> TYPE: PRT
<213> ORGANISM: Homo sapiens
<220> FEATURE:
<221> NAME/KEY: MISC_FEATURE
<222> LOCATION: (1)..(113)
<223> OTHER INFORMATION: Human IgG1 CH1 Domain and Hinge

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro


<210> SEQ ID NO 15
<211> LENGTH: 217
<212> TYPE: PRT
<213> ORGANISM: Artificial Sequence
<220> FEATURE:
<223> OTHER INFORMATION: IgG1 CH2-CH3 Domains Comprising L235V, F243L,
      R292P, Y300L and P396L Substitutions

<400> SEQUENCE: 15

Ala Pro Glu Leu Val Gly Gly Pro Ser Val Phe Leu Leu Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Pro Glu Glu
    50                  55                  60

Gln Tyr Asn Ser Thr Leu Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Leu Val Leu Asp Ser Asp Gly Ser Phe Phe Leu
```

```
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215


<210> SEQ ID NO 16
<211> LENGTH: 110
<212> TYPE: PRT
<213> ORGANISM: Artificial Sequence
<220> FEATURE:
<223> OTHER INFORMATION: IgG4 CH1 Domain and Stabilized Hinge Domain

<400> SEQUENCE: 16

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro
            100                 105                 110


<210> SEQ ID NO 17
<211> LENGTH: 316
<212> TYPE: PRT
<213> ORGANISM: Homo sapiens
<220> FEATURE:
<221> NAME/KEY: MISC_FEATURE
<222> LOCATION: (1)..(316)
<223> OTHER INFORMATION: "2Ig" Form of Human B7-H3, Including 29 Amino
      Acid Residue Signal Sequence
<220> FEATURE:
<221> NAME/KEY: SIGNAL
<222> LOCATION: (1)..(29)
<223> OTHER INFORMATION: Signal Sequence

<400> SEQUENCE: 17

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110
```

```
Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Val Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Gly Ser Val Thr Ile Thr Gly Gln
225                 230                 235                 240

Pro Met Thr Phe Pro Pro Glu Ala Leu Trp Val Thr Val Gly Leu Ser
                245                 250                 255

Val Cys Leu Ile Ala Leu Leu Val Ala Leu Ala Phe Val Cys Trp Arg
            260                 265                 270

Lys Ile Lys Gln Ser Cys Glu Glu Glu Asn Ala Gly Ala Glu Asp Gln
        275                 280                 285

Asp Gly Glu Gly Glu Gly Ser Lys Thr Ala Leu Gln Pro Leu Lys His
    290                 295                 300

Ser Asp Ser Lys Glu Asp Asp Gly Gln Glu Ile Ala
305                 310                 315


<210> SEQ ID NO 18
<211> LENGTH: 534
<212> TYPE: PRT
<213> ORGANISM: Homo sapiens
<220> FEATURE:
<221> NAME/KEY: MISC_FEATURE
<222> LOCATION: (1)..(534)
<223> OTHER INFORMATION: "4Ig" Form of Human B7-H3, Including 29 Amino
      Acid Residue Signal Sequence
<220> FEATURE:
<221> NAME/KEY: SIGNAL
<222> LOCATION: (1)..(29)
<223> OTHER INFORMATION: Signal Sequence

<400> SEQUENCE: 18

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
```

```
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
        355                 360                 365

Pro Asn Lys Asp Leu Arg Pro Gly Asp Thr Val Thr Ile Thr Cys Ser
    370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
        435                 440                 445

Ala His Gly Ser Val Thr Ile Thr Gly Gln Pro Met Thr Phe Pro Pro
    450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
            500                 505                 510

Ser Lys Thr Ala Leu Gln Pro Leu Lys His Ser Asp Ser Lys Glu Asp
        515                 520                 525

Asp Gly Gln Glu Ile Ala
    530
```

<210> SEQ ID NO 19
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of Anti-Human B7-H3 Antibody BRCA84D

<400> SEQUENCE: 19

Asp Ile Ala Met Thr Gln Ser Gln Lys Phe Met Ser Thr Ser Val Gly
1 5 10 15

Asp Arg Val Ser Val Thr Cys Lys Ala Ser Gln Asn Val Asp Thr Asn
20 25 30

Val Ala Trp Tyr Gln Gln Lys Pro Gly Gln Ser Pro Lys Ala Leu Ile
35 40 45

Tyr Ser Ala Ser Tyr Arg Tyr Ser Gly Val Pro Asp Arg Phe Thr Gly
50 55 60

Ser Gly Ser Gly Thr Asp Phe Thr Leu Thr Ile Asn Asn Val Gln Ser
65 70 75 80

Glu Asp Leu Ala Glu Tyr Phe Cys Gln Gln Tyr Asn Asn Tyr Pro Phe
85 90 95

Thr Phe Gly Ser Gly Thr Lys Leu Glu Ile Lys
100 105

<210> SEQ ID NO 20
<211> LENGTH: 122
<212> TYPE: PRT
<213> ORGANISM: Mus musculus
<220> FEATURE:
<221> NAME/KEY: MISC_FEATURE
<222> LOCATION: (1)..(122)
<223> OTHER INFORMATION: VH Domain of Anti-Human B7-H3 Antibody BRCA84D

<400> SEQUENCE: 20

Asp Val Gln Leu Val Glu Ser Gly Gly Gly Leu Val Gln Pro Gly Gly
1 5 10 15

Ser Arg Lys Leu Ser Cys Ala Ala Ser Gly Phe Thr Phe Ser Ser Phe
20 25 30

Gly Met His Trp Val Arg Gln Ala Pro Glu Lys Gly Leu Glu Trp Val
35 40 45

Ala Tyr Ile Ser Ser Asp Ser Ser Ala Ile Tyr Tyr Ala Asp Thr Val
50 55 60

Lys Gly Arg Phe Thr Ile Ser Arg Asp Asn Pro Lys Asn Thr Leu Phe
65 70 75 80

Leu Gln Met Thr Ser Leu Arg Ser Glu Asp Thr Ala Met Tyr Tyr Cys
85 90 95

Gly Arg Gly Arg Glu Asn Ile Tyr Tyr Gly Ser Arg Leu Asp Tyr Trp
100 105 110

Gly Gln Gly Thr Thr Leu Thr Val Ser Ser
115 120

<210> SEQ ID NO 21
<211> LENGTH: 107
<212> TYPE: PRT
<213> ORGANISM: Artificial Sequence
<220> FEATURE:
<223> OTHER INFORMATION: VL Domain of Humanized Anti-Human B7-H3
Antibody hBRCA84D VL1

<400> SEQUENCE: 21

```
Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105
```

<210> SEQ ID NO 22
<211> LENGTH: 107
<212> TYPE: PRT
<213> ORGANISM: Artificial Sequence
<220> FEATURE:
<223> OTHER INFORMATION: VL Domain of Humanized Anti-Human B7-H3 Antibody hBRCA84D VL2

<400> SEQUENCE: 22

```
Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105
```

<210> SEQ ID NO 23
<211> LENGTH: 107
<212> TYPE: PRT
<213> ORGANISM: Artificial Sequence
<220> FEATURE:
<223> OTHER INFORMATION: VL Domain of Humanized Anti-Human B7-H3 Antibody hBRCA84D VL3

<400> SEQUENCE: 23

```
Asp Ile Gln Leu Thr Gln Ser Pro Ser Phe Leu Ser Ala Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
```

```
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105


<210> SEQ ID NO 24
<211> LENGTH: 107
<212> TYPE: PRT
<213> ORGANISM: Artificial Sequence
<220> FEATURE:
<223> OTHER INFORMATION: VL Domain of Humanized Anti-Human B7-H3
      Antibody hBRCA84D VL4

<400> SEQUENCE: 24

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Gln Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105


<210> SEQ ID NO 25
<211> LENGTH: 107
<212> TYPE: PRT
<213> ORGANISM: Artificial Sequence
<220> FEATURE:
<223> OTHER INFORMATION: VL Domain of Humanized Anti-Human B7-H3
      Antibody hBRCA84D VL5

<400> SEQUENCE: 25

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Gln Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105


<210> SEQ ID NO 26
<211> LENGTH: 107
<212> TYPE: PRT
<213> ORGANISM: Artificial Sequence
<220> FEATURE:
<223> OTHER INFORMATION: VL Domain of Humanized Anti-Human B7-H3
```

```
      Antibody hBRCA84D VL6

<400> SEQUENCE: 26

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Glu Tyr Tyr Cys Gln Gln Tyr Asn Asn Tyr Pro Phe
                85                  90                  95

Thr Phe Gly Gln Gly Thr Lys Leu Glu Ile Lys
            100                 105


<210> SEQ ID NO 27
<211> LENGTH: 122
<212> TYPE: PRT
<213> ORGANISM: Artificial Sequence
<220> FEATURE:
<223> OTHER INFORMATION: VH Domain of Humanized Anti-Human B7-H3
      Antibody hBRCA84D VH1

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Gly Arg Glu Asn Ile Tyr Tyr Gly Ser Arg Leu Asp Tyr Trp
            100                 105                 110

Gly Gln Gly Thr Thr Val Thr Val Ser Ser
        115                 120


<210> SEQ ID NO 28
<211> LENGTH: 122
<212> TYPE: PRT
<213> ORGANISM: Artificial Sequence
<220> FEATURE:
<223> OTHER INFORMATION: VH Domain of Humanized Anti-Human B7-H3
      Antibody hBRCA84D VH2

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45
```

```
Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Val Thr Val Ser Ser
        115                 120


<210> SEQ ID NO 29
<211> LENGTH: 122
<212> TYPE: PRT
<213> ORGANISM: Artificial Sequence
<220> FEATURE:
<223> OTHER INFORMATION: VH Domain of Humanized Anti-Human B7-H3
      Antibody hBRCA84D VH3

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Met Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Val Thr Val Ser Ser
        115                 120


<210> SEQ ID NO 30
<211> LENGTH: 122
<212> TYPE: PRT
<213> ORGANISM: Artificial Sequence
<220> FEATURE:
<223> OTHER INFORMATION: VH Domain of Humanized Anti-Human B7-H3
      Antibody hBRCA84D VH4

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ser Glu Asp Thr Ala Val Tyr Tyr Cys
                85                  90                  95
```

```
Ala Arg Gly Arg Glu Asn Ile Tyr Tyr Gly Ser Arg Leu Asp Tyr Trp
            100                 105                 110

Gly Gln Gly Thr Thr Val Thr Val Ser Ser
        115                 120


<210> SEQ ID NO 31
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of Anti-Human B7-H3 Antibody BRCA69D

<400> SEQUENCE: 31

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Asp Asn Leu Glu Gln
65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile Lys
            100                 105


<210> SEQ ID NO 32
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: VH Domain of Anti-Human B7-H3 Antibody BRCA69D

<400> SEQUENCE: 32

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Arg Gly Ile Pro Arg Leu Trp Tyr Phe Asp Val Trp Gly Ala
            100                 105                 110

Gly Thr Thr Val Thr Val Ser Ser
        115                 120


<210> SEQ ID NO 33
<211> LENGTH: 107
```

```
<212> TYPE: PRT
<213> ORGANISM: Artificial Sequence
<220> FEATURE:
<223> OTHER INFORMATION: VL Domain of Humanized Anti-Human B7-H3
      Antibody hBRCA69D VL1

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Pro
                85                  90                  95

Thr Phe Gly Gly Gly Thr Lys Leu Glu Ile Lys
            100                 105


<210> SEQ ID NO 34
<211> LENGTH: 107
<212> TYPE: PRT
<213> ORGANISM: Artificial Sequence
<220> FEATURE:
<223> OTHER INFORMATION: VL Domain of Humanized Anti-Human B7-H3
      Antibody hBRCA69D VL2

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Pro
                85                  90                  95

Thr Phe Gly Gly Gly Thr Lys Leu Glu Ile Lys
            100                 105


<210> SEQ ID NO 35
<211> LENGTH: 120
<212> TYPE: PRT
<213> ORGANISM: Artificial Sequence
<220> FEATURE:
<223> OTHER INFORMATION: VH Domain of Humanized Anti-Human B7-H3
      Antibody hBRCA69D VH1

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Met
```

```
        35                  40                  45

Gly Thr Ile Tyr Pro Gly Asp Gly Asp Thr Arg Tyr Thr Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Pro Arg Leu Trp Tyr Phe Asp Val Trp Gly Gln
            100                 105                 110

Gly Thr Thr Val Thr Val Ser Ser
        115                 120


<210> SEQ ID NO 36
<211> LENGTH: 120
<212> TYPE: PRT
<213> ORGANISM: Artificial Sequence
<220> FEATURE:
<223> OTHER INFORMATION: VH Domain of Humanized Anti-Human B7-H3
      Antibody hBRCA69D VH2

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Met
        35                  40                  45

Gly Thr Ile Tyr Pro Gly Gly Gly Asp Thr Arg Tyr Thr Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Pro Arg Leu Trp Tyr Phe Asp Val Trp Gly Gln
            100                 105                 110

Gly Thr Thr Val Thr Val Ser Ser
        115                 120


<210> SEQ ID NO 37
<211> LENGTH: 108
<212> TYPE: PRT
<213> ORGANISM: Mus musculus
<220> FEATURE:
<221> NAME/KEY: MISC_FEATURE
<222> LOCATION: (1)..(108)
<223> OTHER INFORMATION: VL Domain of Anti-Human B7-H3 Antibody PRCA157

<400> SEQUENCE: 37

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Ser Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Thr Lys Thr Leu Pro Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80
```

```
Glu Asp Phe Gly Arg Tyr Tyr Cys Gln His His Tyr Gly Thr Pro Pro
                85                  90                  95

Trp Thr Phe Gly Gly Gly Thr Asn Leu Glu Ile Lys
            100                 105


<210> SEQ ID NO 38
<211> LENGTH: 117
<212> TYPE: PRT
<213> ORGANISM: Mus musculus
<220> FEATURE:
<221> NAME/KEY: MISC_FEATURE
<222> LOCATION: (1)..(117)
<223> OTHER INFORMATION: VH Domain of Anti-Human B7-H3 Antibody PRCA157

<400> SEQUENCE: 38

Glu Val Gln Gln Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Asn Ser Gly Gly Ser Asn Thr Tyr Tyr Pro Asp Ser Leu
    50                  55                  60

Lys Gly Arg Phe Thr Ile Ser Arg Asp Asn Ala Lys Asn Thr Leu Tyr
65                  70                  75                  80

Leu Gln Met Arg Ser Leu Lys Ser Glu Asp Thr Ala Met Tyr Tyr Cys
                85                  90                  95

Ala Arg His Asp Gly Gly Ala Met Asp Tyr Trp Gly Gln Gly Thr Ser
            100                 105                 110

Val Thr Val Ser Ser
        115


<210> SEQ ID NO 39
<211> LENGTH: 214
<212> TYPE: PRT
<213> ORGANISM: Artificial Sequence
<220> FEATURE:
<223> OTHER INFORMATION: Amino Acid Sequence of the Complete Light Chain
      of Humanized Anti-Human B7-H3 Antibody hBRCA84D-2

<400> SEQUENCE: 39

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 40
<211> LENGTH: 452
<212> TYPE: PRT
<213> ORGANISM: Artificial Sequence
<220> FEATURE:
<223> OTHER INFORMATION: Amino Acid Sequence of the Complete Heavy Chain
      of Humanized Anti-Human B7-H3 Antibody hBRCA84D-2

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Val
225                 230                 235                 240

Gly Gly Pro Ser Val Phe Leu Leu Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
```

```
        275                 280                 285

Val His Asn Ala Lys Thr Lys Pro Pro Glu Glu Gln Tyr Asn Ser Thr
    290                 295                 300

Leu Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Leu Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 41
<211> LENGTH: 288
<212> TYPE: PRT
<213> ORGANISM: Homo sapiens
<220> FEATURE:
<221> NAME/KEY: MISC_FEATURE
<222> LOCATION: (1)..(288)
<223> OTHER INFORMATION: Human PD-1, Iincluding 20 Amino Acid Residue
      Signal Sequence
<220> FEATURE:
<221> NAME/KEY: SIGNAL
<222> LOCATION: (1)..(20)
<223> OTHER INFORMATION: Signal Sequence

<400> SEQUENCE: 41

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140
```

-continued

```
Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285


<210> SEQ ID NO 42
<211> LENGTH: 113
<212> TYPE: PRT
<213> ORGANISM: Mus musculus
<220> FEATURE:
<221> NAME/KEY: MISC_FEATURE
<222> LOCATION: (1)..(113)
<223> OTHER INFORMATION: VH Domain of Anti-Human PD-1 Antibody PD-1 mAb
      1

<400> SEQUENCE: 42

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser


<210> SEQ ID NO 43
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of Anti-Human PD-1 Antibody PD-1 mAb
      1

<400> SEQUENCE: 43

Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105


<210> SEQ ID NO 44
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: VH Domain of Anti-Human PD-1 Antibody PD-1 mAb
      2

<400> SEQUENCE: 44

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120


<210> SEQ ID NO 45
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: VL Domain of Anti-Human PD-1 Antibody PD-1 mAb
      2

<400> SEQUENCE: 45

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60
```

```
Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110


<210> SEQ ID NO 46
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: VH Domain of Anti-Human PD-1 Antibody PD-1 mAb
      3

<400> SEQUENCE: 46

Gln Val Gln Leu Gln Gln Ser Gly Ala Glu Leu Ala Lys Pro Gly Ala
1               5                   10                  15

Ser Val Gln Met Ser Cys Lys Ala Ser Gly Tyr Ser Phe Thr Ser Ser
            20                  25                  30

Trp Ile His Trp Val Lys Gln Arg Pro Gly Gln Gly Leu Glu Trp Ile
        35                  40                  45

Gly Tyr Ile Tyr Pro Ser Thr Gly Phe Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Arg Asp Ser Ser Gly Tyr His Ala Met Asp Tyr Trp Gly
            100                 105                 110

Gln Gly Thr Ser Val Thr Val Ser Ser
        115                 120


<210> SEQ ID NO 47
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: VL Domain of Anti-Human PD-1 Antibody PD-1 mAb
      3

<400> SEQUENCE: 47

Asp Ile Val Leu Thr Gln Ser Pro Ala Ser Leu Thr Val Ser Leu Gly
1               5                   10                  15

Gln Arg Ala Thr Ile Ser Cys Arg Ala Ser Gln Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Lys Phe Gly Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
```

```
            100                 105                 110


<210> SEQ ID NO 48
<211> LENGTH: 117
<212> TYPE: PRT
<213> ORGANISM: Mus musculus
<220> FEATURE:
<221> NAME/KEY: MISC_FEATURE
<222> LOCATION: (1)..(117)
<223> OTHER INFORMATION: VH Domain of Anti-Human PD-1 Antibody PD-1 mAb
      4

<400> SEQUENCE: 48

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser
        115


<210> SEQ ID NO 49
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: VL Domain of Anti-Human PD-1 Antibody PD-1 mAb
      4

<400> SEQUENCE: 49

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105


<210> SEQ ID NO 50
<211> LENGTH: 116
<212> TYPE: PRT
<213> ORGANISM: Mus musculus
<220> FEATURE:
```

```
<221> NAME/KEY: MISC_FEATURE
<222> LOCATION: (1)..(116)
<223> OTHER INFORMATION: VH Domain of Anti-Human PD-1 Antibody PD-1 mAb
      5

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Met Ser Ile Ser Tyr Ala Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Thr Glu Asp Thr Ala Leu Tyr Tyr Cys
                85                  90                  95

Ala Ser Leu Ser Asp Tyr Phe Asp Tyr Trp Gly Gln Gly Thr Thr Val
            100                 105                 110

Thr Val Ser Ser
        115


<210> SEQ ID NO 51
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: VL Domain of Anti-Human PD-1 Antibody PD-1 mAb
      5

<400> SEQUENCE: 51

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Thr Gly Asn Thr Tyr Leu His Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Val Pro Trp Thr Phe Gly Gln Gly Thr Lys Leu Glu Ile Lys
            100                 105                 110


<210> SEQ ID NO 52
<211> LENGTH: 119
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: VH Domain of Anti-Human PD-1 Antibody PD-1 mAb
      6
<220> FEATURE:
<221> NAME/KEY: MISC_FEATURE
<222> LOCATION: (48)..(48)
<223> OTHER INFORMATION: X is Isoleucine (I) or Alanine (A)
```

<400> SEQUENCE: 52

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met Asn Trp Val Arg Gln Ala Pro Gly Gln Gly Leu Glu Trp Xaa
        35                  40                  45

Gly Val Ile His Pro Ser Asp Ser Glu Thr Trp Leu Asp Gln Lys Phe
    50                  55                  60

Lys Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu His Tyr Gly Thr Ser Pro Phe Ala Tyr Trp Gly Gln Gly
            100                 105                 110

Thr Leu Val Thr Val Ser Ser
        115
```

<210> SEQ ID NO 53
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: VL Domain of Anti-Human PD-1 Antibody PD-1 mAb 6
<220> FEATURE:
<221> NAME/KEY: MISC_FEATURE
<222> LOCATION: (26)..(26)
<223> OTHER INFORMATION: X at Position 26 is Asnparagine (N) or Serine (S)
<220> FEATURE:
<221> NAME/KEY: MISC_FEATURE
<222> LOCATION: (58)..(58)
<223> OTHER INFORMATION: X at Position 58 is Glutamine (Q) or Arginine (R)

<400> SEQUENCE: 53

```
Glu Ile Val Leu Thr Gln Ser Pro Ala Thr Leu Ser Leu Ser Pro Gly
1               5                   10                  15

Glu Arg Ala Thr Leu Ser Cys Arg Ala Xaa Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Xaa Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys
            100                 105                 110
```

<210> SEQ ID NO 54
<211> LENGTH: 119
<212> TYPE: PRT
<213> ORGANISM: Mus musculus
<220> FEATURE:
<221> NAME/KEY: MISC_FEATURE
<222> LOCATION: (1)..(119)

```
<223> OTHER INFORMATION: VH Domain of Anti-Human PD-1 Antibody PD-1 mAb
      7
<220> FEATURE:
<221> NAME/KEY: MISC_FEATURE
<222> LOCATION: (12)..(12)
<223> OTHER INFORMATION: X at Position 12 is Valine (V) or Alanine (A)
<220> FEATURE:
<221> NAME/KEY: MISC_FEATURE
<222> LOCATION: (35)..(35)
<223> OTHER INFORMATION: X at Position 35 is Serine (S) or Glycine(G)
<220> FEATURE:
<221> NAME/KEY: MISC_FEATURE
<222> LOCATION: (48)..(48)
<223> OTHER INFORMATION: X at Position 48 is Valine (V) or Threonine (T)
<220> FEATURE:
<221> NAME/KEY: MISC_FEATURE
<222> LOCATION: (86)..(86)
<223> OTHER INFORMATION: X at Position 86 is Leucine (L) orAlanine (A)

<400> SEQUENCE: 54

Glu Val Gln Leu Val Glu Ser Gly Gly Gly Leu Xaa Arg Pro Gly Gly
1               5                   10                  15

Ser Leu Lys Leu Ser Cys Ala Ala Ser Gly Phe Thr Phe Ser Ser Tyr
            20                  25                  30

Leu Val Xaa Trp Val Arg Gln Ala Pro Gly Lys Gly Leu Glu Trp Xaa
        35                  40                  45

Ala Thr Ile Ser Gly Gly Gly Gly Asn Thr Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Xaa Arg Ala Glu Asp Thr Ala Thr Tyr Tyr Cys
                85                  90                  95

Ala Arg Tyr Gly Phe Asp Gly Ala Trp Phe Ala Tyr Trp Gly Gln Gly
            100                 105                 110

Thr Leu Val Thr Val Ser Ser
        115


<210> SEQ ID NO 55
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of Anti-Human PD-1 Antibody PD-1 mAb
      7
<220> FEATURE:
<221> NAME/KEY: MISC_FEATURE
<222> LOCATION: (31)..(31)
<223> OTHER INFORMATION: X at Position 31 is Serine (S) or Asparagine
      (N)
<220> FEATURE:
<221> NAME/KEY: MISC_FEATURE
<222> LOCATION: (50)..(50)
<223> OTHER INFORMATION: X at Position 50 is N or D

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Xaa Tyr
            20                  25                  30

Leu Ala Trp Tyr Gln Gln Lys Pro Gly Lys Ala Pro Lys Leu Leu Ile
        35                  40                  45

Tyr Xaa Ala Lys Thr Leu Ala Ala Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ala Val Pro Trp
                85                  90                  95

Thr Phe Gly Gln Gly Thr Lys Leu Glu Ile Lys
            100                 105


<210> SEQ ID NO 56
<211> LENGTH: 117
<212> TYPE: PRT
<213> ORGANISM: Mus musculus
<220> FEATURE:
<221> NAME/KEY: MISC_FEATURE
<222> LOCATION: (1)..(117)
<223> OTHER INFORMATION: VH Domain of Anti-Human PD-1 Antibody PD-1 mAb
      8

<400> SEQUENCE: 56

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Ser Tyr
            20                  25                  30

Leu Ile Ser Trp Val Arg Gln Ala Pro Gly Lys Gly Leu Glu Trp Val
        35                  40                  45

Ala Ala Ile Ser Gly Gly Gly Ala Asp Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Thr Tyr Tyr Cys
                85                  90                  95

Ala Arg Arg Gly Thr Tyr Ala Met Asp Tyr Trp Gly Gln Gly Thr Leu
            100                 105                 110

Val Thr Val Ser Ser
        115


<210> SEQ ID NO 57
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of Anti-Human PD-1 Antibody PD-1 mAb
      8

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Asn Tyr
            20                  25                  30

Leu Ala Trp Tyr Gln Gln Lys Pro Gly Lys Ala Pro Lys Leu Leu Ile
        35                  40                  45

Tyr Asp Ala Lys Thr Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ala Val Pro Trp
                85                  90                  95

Thr Phe Gly Gln Gly Thr Lys Leu Glu Ile Lys
            100                 105
```

<210> SEQ ID NO 58
<211> LENGTH: 218
<212> TYPE: PRT
<213> ORGANISM: Artificial Sequence
<220> FEATURE:
<223> OTHER INFORMATION: Complete Light Chain of Exemplary Anti-Human PD-1 Antibody "PD-1 mAb 6-ISQ"

<400> SEQUENCE: 58

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 59
<211> LENGTH: 445
<212> TYPE: PRT
<213> ORGANISM: Artificial Sequence
<220> FEATURE:
<223> OTHER INFORMATION: Complete Heavy Chain of Exemplary Anti-Human PD-1 Antibody "PD-1 mAb 6-ISQ"

<400> SEQUENCE: 59

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met Asn Trp Val Arg Gln Ala Pro Gly Gln Gly Leu Glu Trp Ile
        35                  40                  45

Gly Val Ile His Pro Ser Asp Ser Glu Thr Trp Leu Asp Gln Lys Phe
    50                  55                  60

Lys Asp Arg Val Thr Ile Thr Val Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Glu His Tyr Gly Thr Ser Pro Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445
```

<210> SEQ ID NO 60
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Exemplary Human IgG2 CH1 Domain

<400> SEQUENCE: 60

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val
```

<210> SEQ ID NO 61
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Exemplary Human IgG4 CH1 Domain

<400> SEQUENCE: 61

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val
```

<210> SEQ ID NO 62
<211> LENGTH: 22
<212> TYPE: PRT
<213> ORGANISM: Homo sapiens
<220> FEATURE:
<221> NAME/KEY: MISC_FEATURE
<222> LOCATION: (1)..(22)
<223> OTHER INFORMATION: Exemplary Human IgG2 Hinge Region

<400> SEQUENCE: 62

```
Glu Arg Lys Cys Cys Val Glu Cys Pro Pro Glu Arg Lys Cys Cys Val
1               5                   10                  15

Glu Cys Pro Pro Cys Pro
            20
```